US011974572B2

(12) United States Patent
Hoffman et al.

(10) Patent No.: US 11,974,572 B2
(45) Date of Patent: *May 7, 2024

(54) FUNGICIDAL COMPOSITIONS

(71) Applicant: SYNGENTA PARTICIPATIONS AG, Basel (CH)

(72) Inventors: Thomas James Hoffman, Stein (CH); Daniel Stierli, Stein (CH); Renaud Beaudegnies, Stein (CH); Martin Pouliot, Stein (CH); Ulrich Johannes Haas, Stein (CH)

(73) Assignee: SYGENTA PARTICIPATIONS AG, Basel (CH)

( * ) Notice: Subject to any disclaimer, the term of this patent is extended or adjusted under 35 U.S.C. 154(b) by 588 days.

This patent is subject to a terminal disclaimer.

(21) Appl. No.: 16/499,061

(22) PCT Filed: Mar. 22, 2018

(86) PCT No.: PCT/EP2018/057336
§ 371 (c)(1),
(2) Date: Sep. 27, 2019

(87) PCT Pub. No.: WO2018/177894
PCT Pub. Date: Oct. 4, 2018

(65) Prior Publication Data
US 2021/0007358 A1   Jan. 14, 2021

(30) Foreign Application Priority Data

Mar. 31, 2017 (EP) ..................... 17164335
Nov. 21, 2017 (EP) ..................... 17202889

(51) Int. Cl.
A01N 43/82 (2006.01)
A01N 47/28 (2006.01)
C07D 271/06 (2006.01)

(52) U.S. Cl.
CPC ............. *A01N 43/82* (2013.01); *A01N 47/28* (2013.01); *C07D 271/06* (2013.01)

(58) Field of Classification Search
None
See application file for complete search history.

(56) References Cited

U.S. PATENT DOCUMENTS 10,501,425 B2 * 12/2019 Stierli .................. C07D 271/06
10,899,724 B2 *  1/2021 Stierli .................... A01N 43/82
11,066,375 B2 *  7/2021 Stierli .................. C07D 413/04

FOREIGN PATENT DOCUMENTS

| CN | 1927860 A | 3/2007 |
|---|---|---|
| EP | 0276432 A2 | 8/1988 |
| EP | 3165093 A1 | 5/2017 |
| EP | 3165094 A1 | 5/2017 |
| EP | 3187497 A1 | 7/2017 |
| JP | 2017190296 A | 10/2017 |
| WO | 9730047 A1 | 8/1997 |
| WO | 2008037789 A1 | 4/2008 |
| WO | 2011088181 A1 | 7/2011 |
| WO | 2011088192 A1 | 7/2011 |
| WO | 2012052490 A1 | 4/2012 |
| WO | 2013006408 A1 | 1/2013 |
| WO | 2013008162 A1 | 1/2013 |
| WO | 2013009810 A1 | 1/2013 |
| WO | 2013009827 A1 | 1/2013 |
| WO | 2013009830 A1 | 1/2013 |
| WO | 2013064079 A1 | 5/2013 |
| WO | 2013066835 A2 | 5/2013 |
| WO | 2013066839 A2 | 5/2013 |
| WO | 2013080120 A1 | 6/2013 |
| WO | 2015055706 A2 | 4/2015 |
| WO | 2015141867 A1 | 9/2015 |
| WO | 2015185485 A1 | 12/2015 |
| WO | 2017033946 A1 | 3/2017 |
| WO | 2017055473 A1 | 4/2017 |
| WO | 2017076739 A1 | 5/2017 |
| WO | 2017076740 A1 | 5/2017 |
| WO | 2017076742 A1 | 5/2017 |
| WO | 2017076757 A1 | 5/2017 |
| WO | 2017076935 A1 | 5/2017 |
| WO | 2017081309 A1 | 5/2017 |
| WO | 2017081310 A1 | 5/2017 |
| WO | 2017081311 A1 | 5/2017 |
| WO | 2017081312 A1 | 5/2017 |
| WO | 2017085098 A1 | 5/2017 |
| WO | 2017085100 A1 | 5/2017 |
| WO | 2017093019 A1 | 6/2017 |
| WO | 2017110861 A1 | 6/2017 |
| WO | 2017110862 A1 | 6/2017 |
| WO | 2017110864 A1 | 6/2017 |
| WO | 2017110865 A1 | 6/2017 |
| WO | 2017111152 A1 | 6/2017 |
| WO | 2017169893 A1 | 10/2017 |
| WO | 2017178245 A1 | 10/2017 |
| WO | 2017211649 A1 | 12/2017 |
| WO | 2017211650 A1 | 12/2017 |
| WO | 2017211652 A1 | 12/2017 |
| WO | 2017213252 A1 | 12/2017 |
| WO | 2017222951 A1 | 12/2017 |
| WO | 2018030460 A1 | 2/2018 |

OTHER PUBLICATIONS

Cambridge Medchem "Bioisosteric Replacements" no pagination https://web.archive.org/web/20130113020012/https://www.cambridgemedchemconsulting.com/resources/bioisoteres/ (Year: 2013).*
Patani, G. A. et al. "Bioisosterism: A rational approach in drug design" Chem. Rev. 1996, 96, 3147-3176.*
International Search Report for International Patent Application No. PCT/EP2018/057336, dated Apr. 20, 2018.

* cited by examiner

*Primary Examiner* — Erin E Hirt
(74) *Attorney, Agent, or Firm* — BakerHostetler

(57) ABSTRACT

A fungicidal composition comprising a mixture of components (A) and (B), wherein components (A) and (B) are as defined in claim 1, and use of the compositions in agriculture or horticulture for controlling or preventing infestation of plants by phytopathogenic microorganisms, preferably fungi.

13 Claims, No Drawings

FUNGICIDAL COMPOSITIONS

CROSS-REFERENCE TO RELATED APPLICATIONS

This application is a 371 National Stage application of International Application No. PCT/EP2018/057336, filed Mar. 22, 2018, which claims priority to EP 17164335.6, filed Mar. 31, 2017, and EP 17202889.6, filed Nov. 21, 2017, the entire contents of which applications are hereby incorporated by reference.

The present invention relates to novel fungicidal compositions, to their use in agriculture or horticulture for controlling diseases caused by phytopathogens, especially phytopathogenic fungi, and to methods of controlling diseases on useful plants.

Certain oxadiazole derivatives are known as insecticidal and acaricidal agents, eg, from CN 1927860. WO 2013/064079, EP 0 276 432 and WO 2015/185485 describe the use of substituted oxadiazoles for combating phytopathogenic fungi.

Whilst many fungicidal compounds and compositions, belonging to various different chemical classes, have been/are being developed for use as fungicides in crops of useful plants, crop tolerance and activity against particular phytopathogenic fungi do not always satisfy the needs of agricultural practice in many respects. Therefore, there is a continuing need to find new compounds and compositions having superior biological properties for use in controlling or preventing infestation of plants by phytopathogenic fungi. For example, compounds possessing a greater biological activity, an advantageous spectrum of activity, an increased safety profile, improved physico-chemical properties, or increased biodegradability. Or else, compositions possessing a broader spectrum of activity, improved crop tolerance, synergistic interactions or potentiating properties, or compositions which display a more rapid onset of action or which have longer lasting residual activity or which enable a reduction in the number of applications and/or a reduction in the application rate of the compounds and compositions required for effective control of a phytopathogen, thereby enabling beneficial resistance-management practices, reduced environmental impact and reduced operator exposure.

The use of compositions comprising mixtures of different fungicidal compounds possessing different modes of action can address some of these needs (eg, by combining fungicides with differing spectrums of activity).

According to the present invention, there is provided a fungicidal composition comprising a mixture of components (A) and (B) as active ingredients, wherein component (A) is a compound of formula (I):

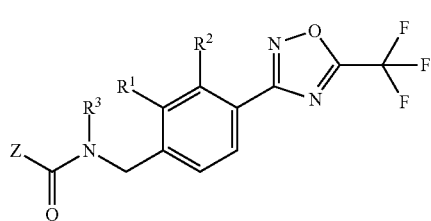

(I)

wherein
$R^1$=hydrogen or fluoro;
$R^2$=hydrogen or fluoro;
$R^3$=methyl, ethyl, iso-propyl, methoxy, ethoxy, methoxyethyl, 2,2,2-trifluoroethyl or cyclopropyl;
Z=$R^4$ or $R^5$, wherein
$R^4$=ethyl, iso-propyl, 2-propen-2-yl ($H_2C$=C($CH_3$)—), 3-butyn-1-yl (HC≡$CCH_2CH_2$—), methoxymethyl, 1-methoxyethyl, (difluoromethoxy)methyl, 2,2,2-trifluoroethyl, cyclopropyl, 2,2-difluorocyclopropyl, tetrahydrofuran-2-yl; and
$R^5$=—$NR^6R^7$, wherein
$R^6$=hydrogen or methyl; and
$R^7$=methyl, ethyl, iso-propyl, methoxy, ethoxy, allyl ($H_2C$=$CHCH_2$—), propargyl (HC≡$CCH_2$—), 2,2,2-trifluoroethyl, cyclopropyl or (cyclopropyl)methyl,
or salt or N-oxide thereof,
and
component (B) is a compound selected from the group consisting of:
benzovindiflupyr, fluxapyroxad, pydiflumetofen, isopyrazam, fluopyram, penthiopyrad, sedaxane, bixafen, difenoconazole, cyproconazole, tebuconazole, hexaconazole, prothioconazole, propiconazole, epoxiconazole, flutriafol, mefentrifluconazole, ipconazole, paclobutrazol, azoxystrobin, trifloxystrobin, picoxystrobin, pyraclostrobin, metalaxyl-M, fenpropidin, fenpropimorph, cyprodinil, spiroxamine, mancozeb, chlorothalonil, oxathiapiprolin, mandipropamid, fluazinam, fludioxinil, fosetyl-aluminium, acibenzolar-S-methyl, procymidone, carbendazim, fenhexamid, prochloraz, prohexadione-calcium, Timorex Gold™ (plant extract comprising tea tree oil), N'-[5-bromo-2-methyl-6-(1-methyl-2-propoxy-ethoxy)-3-pyridyl]-N-ethyl-N-methyl-formamidine), N'-[5-bromo-2-methyl-6-[(1S)-1-methyl-2-propoxy-ethoxy]-3-pyridyl]-N-ethyl-N-methyl-formamidine, N'-[5-bromo-2-methyl-6-[(1R)-1-methyl-2-propoxy-ethoxy]-3-pyridyl]-N-ethyl-N-methyl-formamidine, N'-[5-bromo-2-methyl-6-(1-methyl-2-propoxy-ethoxy)-3-pyridyl]-N-isopropyl-N-methyl-formamidine, N'-[5-chloro-2-methyl-6-(1-methyl-2-propoxy-ethoxy)-3-pyridyl]-N-ethyl-N-methyl-formamidine, calcium phosphonate, cis-jasmone, trinexapac-ethyl, glyphosate, 2,4-D (2,4-dichlorophenoxyacetic acid) and thiamethoxam.

In general, the weight ratio of component (A) to component (B) may preferably be from 100:1 to 1:100, from 50:1 to 1:50, from 20:1 to 1:40, from 15:1 to 1:30, from 12:1 to 1:25, from 10:1 to 1:20, from 5:1 and 1:15, from 3:1 to 1:10 or from 2:1 to 1:5.

Further according to the invention, there is provided a method of controlling or preventing phytopathogenic diseases, especially phytopathogenic fungi, on useful plants or on propagation material thereof, which comprises applying to the useful plants, the locus thereof or propagation material thereof a fungicidal composition according to the invention.

The benefits provided by certain fungicidal mixture compositions according to the invention may also include, inter alia, advantageous levels of biological activity for protecting plants against diseases that are caused by fungi or superior properties for use as agrochemical active ingredients (for example, greater biological activity, an advantageous spectrum of activity, an increased safety profile, improved physico-chemical properties, or increased biodegradability).

The presence of one or more possible asymmetric carbon atoms in a compound of formula (I) means that the compounds may occur in optically isomeric forms, i.e., enantiomeric or diastereomeric forms (eg, (R)- and (S)-enantiomers of compound X.04, (R)- and (S)-enantiomers of compound X.06, (R)- and (S)-enantiomers of compound X.12 and (R)- and (S)-enantiomers of compound X.13). Also atropisomers may occur as a result of restricted rotation about a single bond. The present invention includes all those possible isomeric forms (e.g. geometric isomers) and mixtures thereof for a compound of formula (I). The present invention includes all possible tautomeric forms for a compound of formula (I), and also a racemic compound, i.e., a mixture of at least two enantiomers in a ratio of substantially 50:50.

In each case, the compounds of formula (I) according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

Preferred groups and values for the substituents $R^1$, $R^2$, $R^3$, Z, $R^4$, $R^5$ and $R^6$ in the compounds of formula (I) are, in any combination thereof, as set out below.

Preferably $R^1$ and $R^2$ are both hydrogen;
Preferably $R^3$ is ethyl or methoxy;
Preferably, Z is $R^4$ and $R^4$ is iso-propyl, (1-methoxy)ethyl, cyclopropyl, or
Z is $R^5$ and $R^5$ is $NR^6R^7$ wherein $R^6$ is hydrogen and $R^7$ is methyl;
or a salt, enantiomer, tautomer or N-oxide of such compounds.

Most preferably, component (A) is a compound selected from compound no. X.01, X.02, X.03, X.04, X.05, X.06, X.07, X.08, X.09, X.10, X.11, X.12, X.13, X.14, X.15, X.16, X.17, X.18, X.19, X.20, X.21, X.22, X.23, X.24, or X.25 as defined in the Table X below. More preferably, component (A) is a compound selected from compound no. X.01, X.04, X.07, X.14, X.24 or X.25 as defined in the Table X below.

TABLE X

| Compound number | Compound structure | IUPAC name |
|---|---|---|
| X.01 | 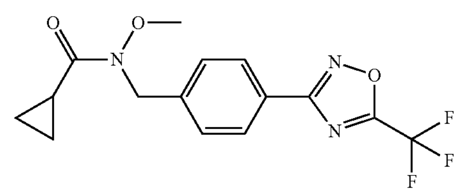 | N-methoxy-N-[[4-[5-(trifluoromethyl)-1,2,4-oxadiazol-3-yl]phenyl]methyl]cyclopropanecarboxamide |
| X.02 | 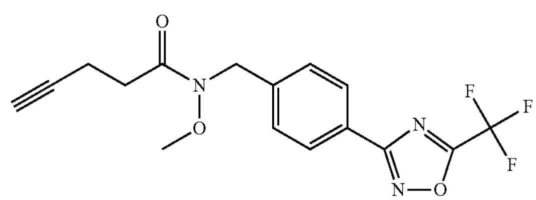 | N-methoxy-N-[[4-[5-(trifluoromethyl)-1,2,4-oxadiazol-3-yl]phenyl]methyl]pent-4-ynamide |
| X.03 | 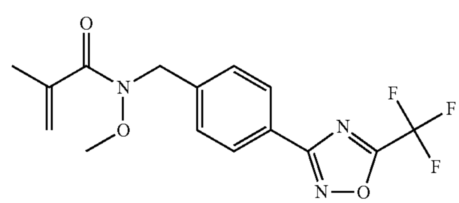 | N-methoxy-2-methyl-N-[[4-[5-(trifluoromethyl)1,2,4-oxadiazol-3-yl]phenyl]methyl]prop-2-enamide |
| X.04 | 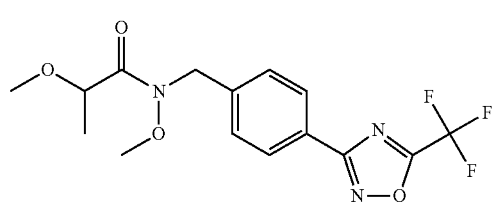 | N,2-dimethoxy-N-[[4-[5-(trifluoromethyl)-1,2,4-oxadiazol-3-yl]phenyl]methyl]propanamide |
| X.05 | 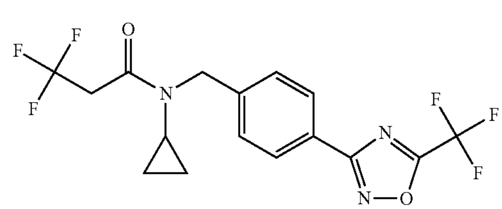 | N-cyclopropyl-3,3,3-trifluoro-N-[[4-[5-(trifluoromethyl)-1,2,4-oxadiazol-3-yl]phenyl]methyl]propanamide |

TABLE X-continued

| Compound number | Compound structure | IUPAC name |
| --- | --- | --- |
| X.06 | 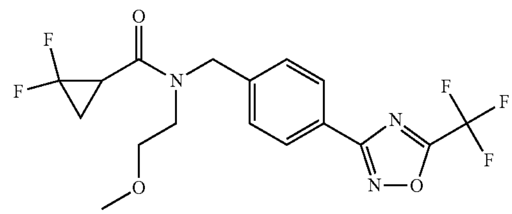 | 2,2-difluoro-N-(2-methoxyethyl)-N-[[4-[5-(trifluoromethyl)-1,2,4-oxadiazol-3-yl]phenyl]methyl]cyclopropanecarboxamide |
| X.07 | 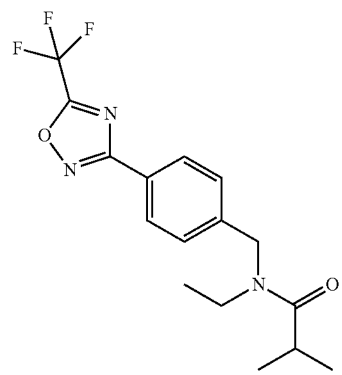 | N-ethyl-2-methyl-N-[[4-[5-(trifluoromethyl)-1,2,4-oxadiazol-3-yl]phenyl]methyl]propanamide |
| X.08 | 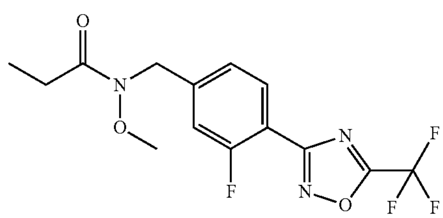 | N-[[3-fluoro-4-[5-(trifluoromethyl)-1,2,4-oxadiazol-3-yl]phenyl]methyl]-N-methoxy-propanamide |
| X.09 | 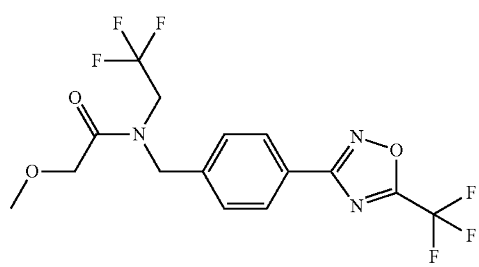 | 2-methoxy-N-(2,2,2-trifluoroethyl)-N-[[4-[5-(trifluoromethyl)-1,2,4-oxadiazol-3-yl]phenyl]methyl]acetamide |
| X.10 | 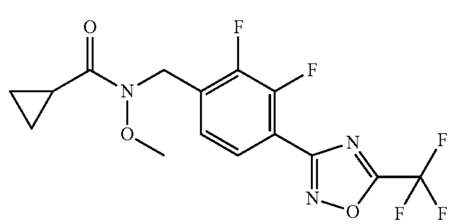 | N-[[2,3-difluoro-4-[5-(trifluoromethyl)-1,2,4-oxadiazol-3-yl]phenyl]methyl]-N-methoxy-cyclopropanecarboxamide |
| X.11 | 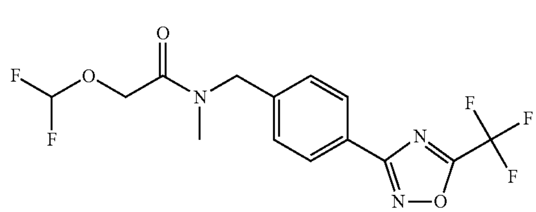 | 2-(difluoromethoxy)-N-methyl-N-[[4-[5-(trifluoromethyl)-1,2,4-oxadiazol-3-yl]phenyl]methyl]acetamide |

TABLE X-continued

| Compound number | Compound structure | IUPAC name |
| --- | --- | --- |
| X.12 | 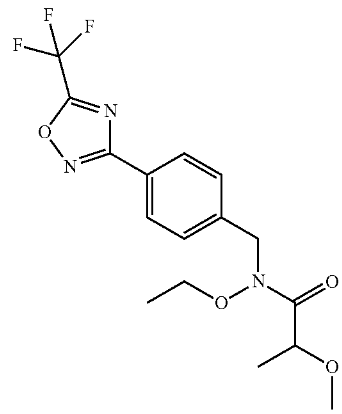 | N-ethoxy-2-methoxy-N-[[4-[5-(trifluoromethyl)-1,2,4-oxadiazol-3-yl]phenyl]methyl]propanamide |
| X.13 | 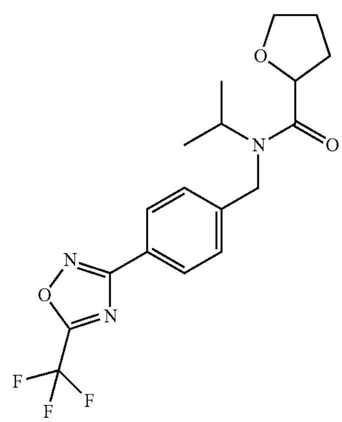 | N-isopropyl-N-[[4-[5-(trifluoromethyl)-1,2,4-oxadiazol-3-yl]phenyl]methyl]tetrahydrofuran-2-carboxamide |
| X.14 | 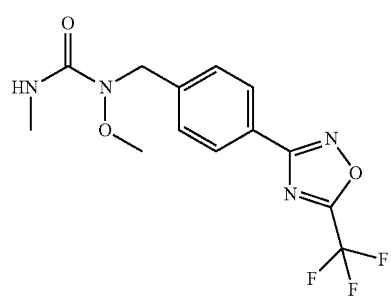 | 1-methoxy-3-methyl-1-[[4-[5-(trifluoromethyl)-1,2,4-oxadiazol-3-yl]phenyl]methyl]urea |
| X.15 | 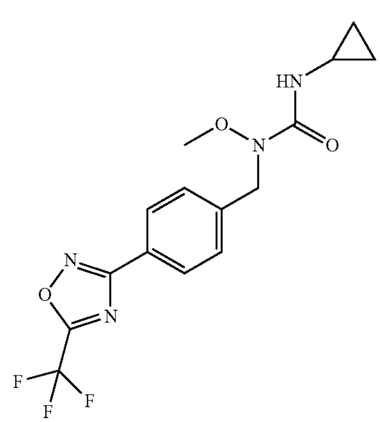 | 3-cyclopropyl-1-methoxy-1-[[4-[5-(trifluoromethyl)-1,2,4-oxadiazol-3-yl]phenyl]methyl]urea |

TABLE X-continued
| Compound number | Compound structure | IUPAC name |
| --- | --- | --- |
| X.16 | 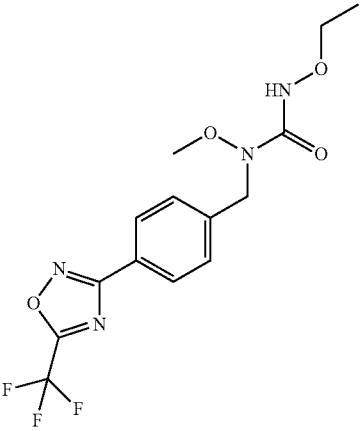 | 3-ethoxy-1-methoxy-1-[[4-[5-(trifluoromethyl)-1,2,4-oxadiazol-3-yl]phenyl]methyl]urea |
| X.17 | 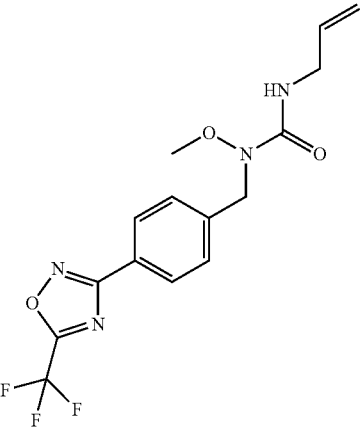 | 3-allyl-1-methoxy-1-[[4-[5-(trifluoromethyl)-1,2,4-oxadiazol-3-yl]phenyl]methyl]urea |
| X.18 | 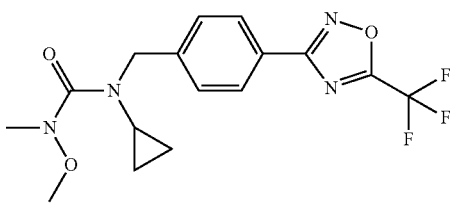 | 1-cyclopropyl-3-methoxy-3-methyl-1-[[4-[5-(trifluoromethyl)-1,2,4-oxadiazol-3-yl]phenyl]methyl]urea |
| X.19 | 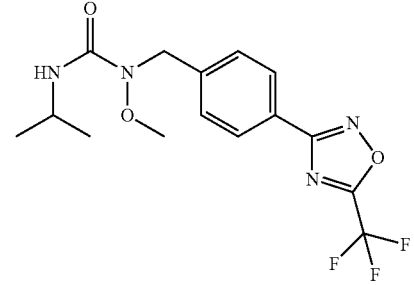 | 3-isopropyl-1-methoxy-1-[[4-[5-(trifluoromethyl)-1,2,4-oxadiazol-3-yl]phenyl]methyl]urea |

TABLE X-continued

| Compound number | Compound structure | IUPAC name |
| --- | --- | --- |
| X.20 | 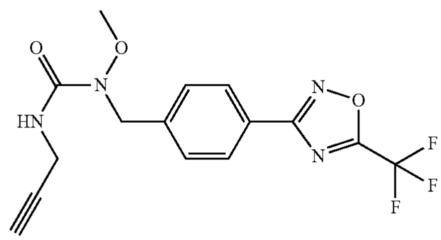 | 1-methoxy-3-prop-2-ynyl-1-[[4-[5-(trifluoromethyl)-1,2,4-oxadiazol-3-yl]phenyl]methyl]urea |
| X.21 | 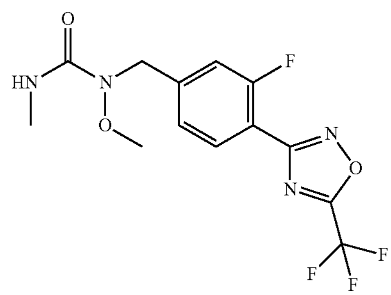 | 1-[[3-fluoro-4-[5-(trifluoromethyl)-1,2,4-oxadiazol-3-yl]phenyl]methyl]-1-methoxy-3-methyl-urea |
| X.22 | 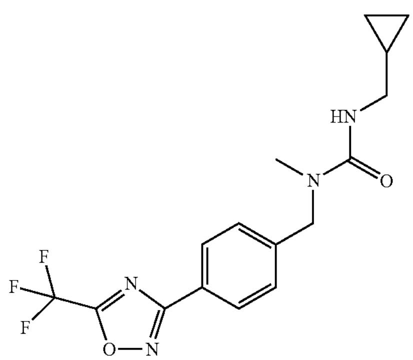 | 3-(cyclopropylmethyl)-1-methyl-1-[[4-[5-(trifluoromethyl)-1,2,4-oxadiazol-3-yl]phenyl]methyl]urea |
| X.23 | 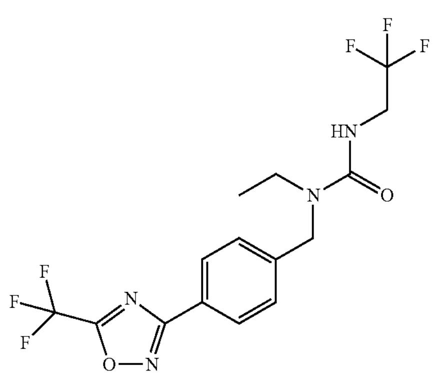 | 1-ethyl-3-(2,2,2-trifluoroethyl)-1-[[4-[5-(trifluoromethyl)-1,2,4-oxadiazol-3-yl]phenyl]methyl]urea |

TABLE X-continued

| Compound number | Compound structure | IUPAC name |
| --- | --- | --- |
| X.24 | 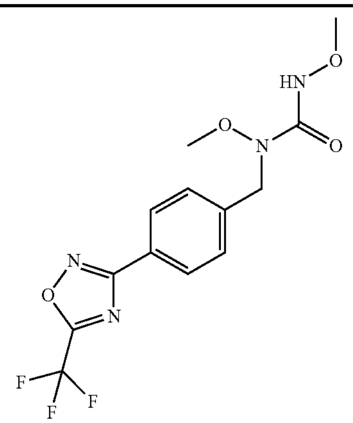 | 1,3-dimethoxy-1-[[4-[5-(trifluoromethyl)-1,2,4-oxadiazol-3-yl]phenyl]methyl]urea |
| X.25 | 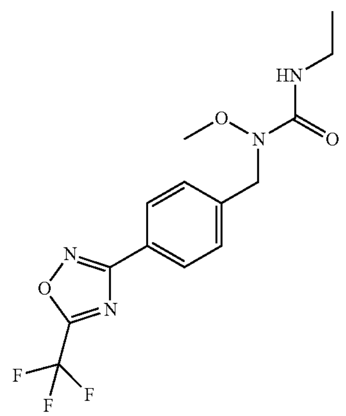 | 3-ethyl-1-methoxy-1-[[4-[5-(trifluoromethyl)-1,2,4-oxadiazol-3-yl]phenyl]methyl]urea |

The presence of an asymmetric carbon atom in compounds X.04, X.06, X.12 and X.13 means that these compounds may occur in chiral enantiomeric forms, i.e., (R)- and (S)-enantiomers as depicted below.

X.04(a)

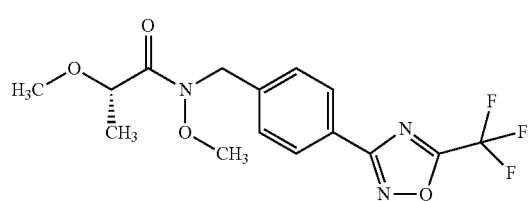

X.04(b)

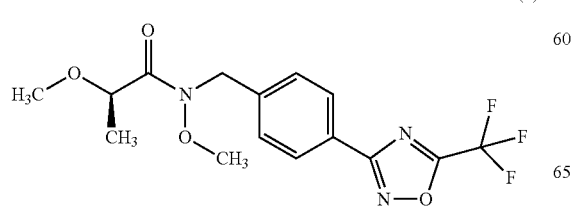

-continued

X.06(a)

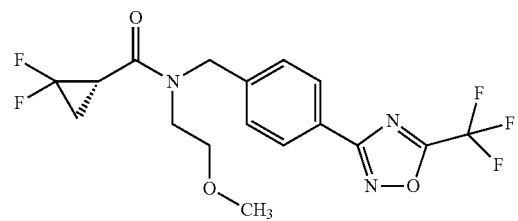

X.06(b)

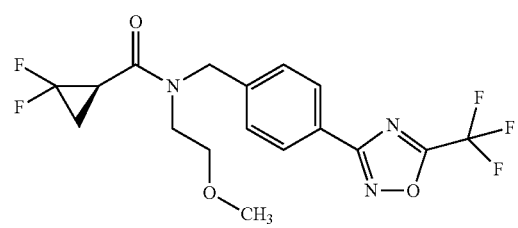

-continued

X.12(a)
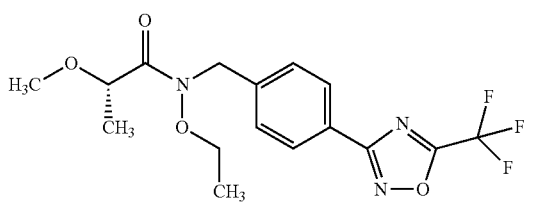

X.12(b)
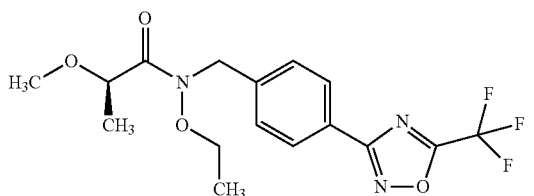

X.13(a)
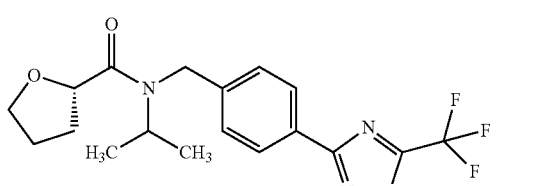

X.13(b)
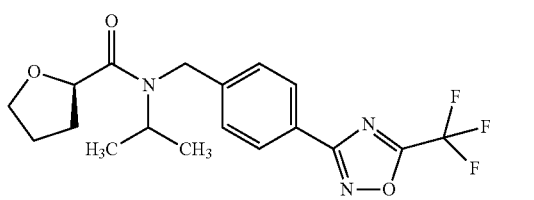

Enantiomerically pure final compounds may be obtained from racemic starting materials as appropriate via standard physical separation techniques, such as reverse phase chiral chromatography, or through stereoselective synthetic techniques, e.g., by using chiral starting materials.

Preferably, component (B) is a compound selected from the group consisting of:

benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, metalaxyl-M, fenpropidin, fenpropimorph, cyprodinil, spiroxamine, mancozeb, chlorothalonil, oxathiapiprolin, mandipropamid, fluazinam, fosetyl-aluminium, trinexapac-ethyl, acibenzolar-S-methyl, Timorex Gold™ (plant extract comprising tea tree oil), glyphosate, thiamethoxam, or

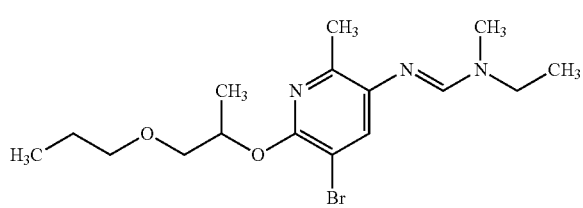

(N'-[5-bromo-2-methyl-6-(1-methyl-2-propoxy-ethoxy)-3-pyridyl]-N-ethyl-N-methyl-formamidine).

More preferably, component (B) is a compound selected from the group consisting of benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine.

Still more preferably, component (B) is a compound selected from the group consisting of benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine.

The component (B) compounds are referred to herein and above by a so-called "ISO common name" or another "common name" being used in individual cases or a trademark name. The component (B) compounds are known and are commercially available and/or can be prepared using procedures known in the art and/or procedures reported in the literature.

In a preferred composition according to the invention component (A) is compound no. X.01 [N-methoxy-N-[[4-[5-(trifluoromethyl)-1,2,4-oxadiazol-3-yl]phenyl]methyl] cyclopropanecarboxamide] or a salt, enantiomer, tautomer or N-oxide thereof, and component (B) is a compound selected from the group consisting of benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.02 [N-methoxy-N-[[4-[5-(trifluoromethyl)-1,2,4-oxadiazol-3-yl]phenyl] methyl]pent-4-ynamide] or a salt, enantiomer, tautomer or N-oxide thereof, and component (B) is a compound selected from the group consisting of benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.03 [N-methoxy-2-methyl-N-[[4-[5-(trifluoromethyl)-1,2,4-oxadiazol-3-yl] phenyl]methyl]prop-2-enamide] or a salt, enantiomer, tautomer or N-oxide thereof, and component (B) is a compound selected from the group consisting of benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.04 [N,2-dimethoxy-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from the group consisting of benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.05 [N-cyclopropyl-3,3,3-trifluoro-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from the group consisting of benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.06 [2,2-difluoro-N-(2-m ethoxyethyl)-N-[[4-[5-(trifluoromethyl)-1,2,4-oxadiazol-3-yl]phenyl]methyl]cyclopropanecarboxamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.07 [N-ethyl-2-methyl-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.08 [N-[[3-fluoro-4-[5-(trifluoromethyl)-1,2,4-oxadiazol-3-yl]phenyl]methyl]-N-methoxy-propanamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.09 [2-methoxy-N-(2,2,2-trifluoroethyl)-N-[[4-[5-(trifluoromethyl)-1,2,4-oxadiazol-3-yl]phenyl]methyl]acetamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.10 [N-[[2,3-difluoro-4-[5-(trifluoromethyl)-1,2,4-oxadiazol-3-yl]phenyl]methyl]-N-methoxy-cyclopropanecarboxamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.11 [2-(difluoromethoxy)-N-methyl-N-[[4-[5-(trifluoromethyl)-1,2,4-oxadiazol-3-yl]phenyl]methyl]acetamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.12 [N-ethoxy-2-methoxy-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.13 [N-isopropyl-N-[[4-[5-(trifluoromethyl)-1,2,4-oxadiazol-3-yl]phenyl]

methyl]tetrahydrofuran-2-carboxamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.14 [1-methoxy-3-methyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.15 [3-cyclopropyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.16 [3-ethoxy-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.17 [3-allyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from of benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.18 [1-cyclopropyl-3-methoxy-3-methyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.19 [3-isopropyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.20 [1-methoxy-3-prop-2-ynyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.21 [1-[[3-fluoro-4-[5-(trifluoromethyl)-1,2,4-oxadiazol-3-yl]phenyl]methyl]-1-methoxy-3-methyl-urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.22 [3-(cyclopropylmethyl)-1-methyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.23 [1-ethyl-3-(2,2,2-trifluoroethyl)-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.24 [1,3-dimethoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another preferred composition according to the invention, component (A) is compound no. X.25 [3-ethyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, [5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In a more preferred composition according to the invention, component (A) is compound no. X.01 [N-methoxy-N-[[4-[5-(trifluoromethyl)-1,2,4-oxadiazol-3-yl]phenyl]methyl]cyclopropanecarboxamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.02 [N-methoxy-N-[[4-[5-(trifluoromethyl)-1,2,4-oxadiazol-3-yl]phenyl]methyl]pent-4-ynamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.03 [N-methoxy-2-methyl-N-[[4-[5-(trifluoromethyl)-1,2,4-oxadiazol-3-yl]phenyl]methyl]prop-2-enamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.04 [N,2-dimethoxy-N-[[4-[5-(trifluoromethyl)-1,2,4-oxadiazol-3-yl]phenyl]methyl]propanamide] or a salt, enantiomer, tautomer or N-oxide thereof, and component (B) is a compound benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.05 [N-cyclopropyl-3,3,3-trifluoro-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.06 [2,2-difluoro-N-(2-methoxyethyl)-N-[[4-[5-(trifluoromethyl)-1,2,4-oxadiazol-3-yl]phenyl]methyl]cyclopropanecarboxamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.07 [N-ethyl-2-methyl-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.08 [N-[[3-fluoro-4-[5-(trifluoromethyl)-1,2,4-oxadiazol-3-yl]phenyl]methyl]-N-methoxy-propanamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N- methyl-formamidine, wherein the weight ratio of component (A) to component (B) is from 15:1 to 1:30.

In another more preferred composition according to the invention, component (A) is compound no. X.09 [2-methoxy-N-(2,2,2-trifluoroethyl)-N-[[4-[5-(trifluoromethyl)-1,2,4-oxadiazol-3-yl]phenyl]methyl]acetamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.10 [N-[[2,3-difluoro-4-[5-(trifluoromethyl)-1,2,4-oxadiazol-3-yl]phenyl]methyl]-N-methoxy-cyclopropanecarboxamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.11 [2-(difluoromethoxy)-N-methyl-N-[[4-[5-(trifluoromethyl)-1,2,4-oxadiazol-3-yl]phenyl]methyl]acetamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.12 [N-ethoxy-2-m ethoxy-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.13 [N-isopropyl-N-[[4-[5-(trifluoromethyl)-1,2,4-oxadiazol-3-yl]phenyl]methyl]tetrahydrofuran-2-carboxamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.14 [1-methoxy-3-methyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.15 [3-cyclopropyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.16 [3-ethoxy-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.17 [3-allyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.18 [1-cyclopropyl-3-methoxy-3-methyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.19 [3-isopropyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.20 [1-methoxy-3-prop-2-ynyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N- methyl-formamidine, wherein the weight ratio of component (A) to component (B) is from 15:1 to 1:30.

In another more preferred composition according to the invention, component (A) is compound no. X.21 [1-[[3-fluoro-4-[5-(trifluoromethyl)-1,2,4-oxadiazol-3-yl]phenyl]methyl]-1-methoxy-3-methyl-urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.22 [3-(cyclopropylmethyl)-1-methyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.23 [1-ethyl-3-(2,2,2-trifluoroethyl)-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.24 [1,3-dimethoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In another more preferred composition according to the invention, component (A) is compound no. X.25 [3-ethyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 15:1 to 1:30.

In a still more preferred composition according to the invention, component (A) is compound no. X.01 [N-methoxy-N-[[4-[5-(trifluoromethyl)-1,2,4-oxadiazol-3-yl]phenyl]methyl]cyclopropanecarboxamide] or a salt, enantiomer, tautomer or N-oxide thereof, and component (B) is a compound selected from the group consisting of benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.02 [N-methoxy-N-[[4-[5-(trifluoromethyl)-1,2,4-oxadiazol-3-yl]phenyl]methyl]pent-4-ynamide] or a salt, enantiomer, tautomer or N-oxide thereof, and component (B) is a compound selected from the group consisting of benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.03 [N-methoxy-2-methyl-N-[[4-[5-(trifluoromethyl)-1,2,4-oxadiazol-3-yl]phenyl]methyl]prop-2-enamide] or a salt, enantiomer, tautomer or N-oxide thereof, and component (B) is a compound selected from the group consisting of benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.04 [N,2-dimethoxy-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from the group consisting of benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.05 [N-cyclopropyl-3,3,3-trifluoro-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from the group consisting of benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.06 [2,2-difluoro-N-(2-methoxyethyl)-N-[[4-[5-(trifluoromethyl)-1,2,4-oxadiazol-3-yl]phenyl]methyl]cyclopropanecarboxamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.07 [N-ethyl-2-methyl-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.08 [N-[[3-fluoro-4-[5-(trifluoromethyl)-1,2,4-oxadiazol-3-yl]phenyl]methyl]-N-methoxy-propanamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.09 [2-methoxy-N-(2,2,2-trifluoroethyl)-N-[[4-[5-(trifluoromethyl)-1,2,4-oxadiazol-3-yl]phenyl]methyl]acetamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.10 [N-[[2,3-difluoro-4-[5-(trifluoromethyl)-1,2,4-oxadiazol-3-yl]phenyl]methyl]-N-methoxy-cyclopropanecarboxamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.11 [2-(difluoromethoxy)-N-methyl-N-[[4-[5-(trifluoromethyl)-1,2,4-oxadiazol-3-yl]phenyl]methyl]acetamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.12 [N-ethoxy-2-methoxy-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.13 [N-isopropyl-N-[[4-[5-(trifluoromethyl)-1,2,4-oxadiazol-3-yl]phenyl]methyl]tetrahydrofuran-2-carboxamide] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.14 [1-methoxy-3-methyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl- N-methyl-formamidine, wherein the weight ratio of component (A) to component (B) is from 10:1 to 1:10 (or even more preferably, 5:1 to 1:5).

In another still more preferred composition according to the invention, component (A) is compound no. X.15 [3-cyclopropyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.16 [3-ethoxy-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.17 [3-allyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.18 [1-cyclopropyl-3-methoxy-3-methyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.19 [3-isopropyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.20 [1-methoxy-3-prop-2-ynyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.21 [1-[[3-fluoro-4-[5-(trifluoromethyl)-1,2,4-oxadiazol-3-yl]phenyl]methyl]-1-methoxy-3-methyl-urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.22 [3-(cyclopropylmethyl)-1-methyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.23 [1-ethyl-3-(2,2,2-trifluoroethyl)-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2- methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.24 [1,3-dimethoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another still more preferred composition according to the invention, component (A) is compound no. X.25 [3-ethyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In a most preferred composition according to the invention, component (A) is compound no. X.01 [N-methoxy-N-[[4-[5-(trifluoromethyl)-1,2,4-oxadiazol-3-yl]phenyl]methyl]cyclopropanecarboxamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.02 [N-methoxy-N-[[4-[5-(trifluoromethyl)-1,2,4-oxadiazol-3-yl]phenyl]methyl]pent-4-ynamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.03 [N-methoxy-2-methyl-N-[[4-[5-(trifluoromethyl)-1,2,4-oxadiazol-3-yl]phenyl]methyl]prop-2-enamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.04 [N,2-dimethoxy-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.05 [N-cyclopropyl-3,3,3-trifluoro-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.06 [2,2-difluoro-N-(2-methoxyethyl)-N-[[4-[5-(trifluoromethyl)-1,2,4-oxadiazol-3-yl]phenyl]methyl]cyclopropanecarboxamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.07 [N-ethyl-2-methyl-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.08 [N-[[3-fluoro-4-[5-(trifluoromethyl)-1,2,4-oxadiazol-3-yl]phenyl]methyl]-N-methoxy-propanamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.09 [2-methoxy-N-(2,2,2-trifluoroethyl)-N-[[4-[5-(trifluoromethyl)-1,2,4-oxadiazol-3-yl]phenyl]methyl]acetamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.10 [N-[[2,3-difluoro-4-[5-(trifluoromethyl)-1,2,4-oxadiazol-3-yl]phenyl]methyl]-N-methoxy-cyclopropanecarboxamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.11 [2-(difluoromethoxy)-N-methyl-N-[[4-[5-(trifluoromethyl)-1,2,4-oxadiazol-3-yl]phenyl]methyl]acetamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.12 [N-ethoxy-2-methoxy-N-[[4-[5-(trifluoromethyl)-1,2,4-oxadiazol-3-yl]phenyl]methyl]propanamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.13 [N-isopropyl-N-[[4-[5-(trifluoromethyl)-1,2,4-oxadiazol-3-yl]phenyl]methyl]tetrahydrofuran-2-carboxamide] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.14 [1-methoxy-3-methyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.15 [3-cyclopropyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.16 [3-ethoxy-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.17 [3-allyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.18 [1-cyclopropyl-3-methoxy-3-methyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.19 [3-isopropyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.20 [1-methoxy-3-prop-2-ynyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.21 [1-[[3-fluoro-4-[5-(trifluoromethyl)-1,2,4-oxadiazol-3-yl]phenyl]methyl]-1-methoxy-3-methyl-urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.22 [3-(cyclopropylmethyl)-1-methyl-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.23 [1-ethyl-3-(2,2,2-trifluoroethyl)-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.24 [1,3-dimethoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In another most preferred composition according to the invention, component (A) is compound no. X.25 [3-ethyl-1-methoxy-1-[[4-[5-(trifluoromethyl)-1,2,4-oxadiazol-3-yl]phenyl]methyl]urea] or a salt, enantiomer, tautomer or N-oxide thereof, and component (B) is a compound selected from benzovindiflupyr, pydiflumetofen, difenoconazole, cyproconazole, hexaconazole, prothioconazole, azoxystrobin, fenpropidin, or N'-[5-bromo-2-methyl-6-(1-methyl-2-propoxy-ethoxy)-3-pyridyl]-N-ethyl-N-methyl-formamidine, wherein the weight ratio of component (A) to component (B) is from 10:1 to 1:10 (or even more preferably, 5:1 to 1:5).

In any of the preferred compositions according to the invention, the composition may comprise an additional active ingredient component (C), which is different to component (B), and is selected from the group consisting of:

benzovindiflupyr, fluxapyroxad, pydiflumetofen, isopyrazam, fluopyram, penthiopyrad, sedaxane, bixafen, difenoconazole, cyproconazole, tebuconazole, hexaconazole, prothioconazole, propiconazole, epoxiconazole, flutriafol, mefentrifluconazole, ipconazole, paclobutrazol, azoxystrobin, trifloxystrobin, picoxystrobin, pyraclostrobin, metalaxyl-M, fenpropidin, fenpropimorph, cyprodinil, spiroxamine, mancozeb, chlorothalonil, oxathiapiprolin, mandipropamid, fluazinam, fludioxinil, fosetyl-aluminium, acibenzolar-S-methyl, procymidone, carbendazim, fenhexamid, prochloraz, prohexadione-calcium, Timorex Gold™ (plant extract comprising tea tree oil),

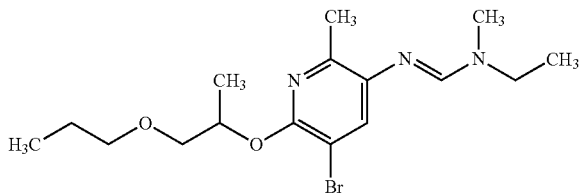

(N'-[5-bromo-2-methyl-6-(1-methyl-2-propoxy-ethoxy)-3-pyridyl]-N-ethyl-N-methyl-formamidine), calcium phosphonate, cis-jasmone, trinexapac-ethyl, glyphosate, 2,4-D (2,4-dichlorophenoxyacetic acid) and thiamethoxam.

The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

The term "plants" refers to all physical parts of a plant, including seeds, seedlings, saplings, roots, tubers, stems, stalks, foliage, and fruits.

The term "plant propagation material" denotes all generative parts of a plant, for example seeds or vegetative parts of plants such as cuttings and tubers. It includes seeds in the strict sense, as well as roots, fruits, tubers, bulbs, rhizomes, and parts of plants.

The term "locus" as used herein means fields in or on which plants are growing, or where seeds of cultivated plants are sown, or where seed will be placed into the soil. It includes soil, seeds, and seedlings, as well as established vegetation.

Throughout this document the expression "composition" stands for the various mixtures or combinations of components (A) and (B) (including the above-defined embodiments), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the components (A) and (B) is not essential for working the present invention.

The composition according to the invention is effective against harmful microorganisms, such as microorganisms, that cause phytopathogenic diseases, in particular against phytopathogenic fungi and bacteria.

The composition of the invention may be used to control plant diseases caused by a broad spectrum of fungal plant pathogens in the Basidiomycete, Ascomycete, Oomycete and/or Deuteromycete, Blasocladiomycete, Chrytidiomycete, Glomeromycete and/or Mucoromycete classes.

The composition is effective in controlling a broad spectrum of plant diseases, such as foliar pathogens of ornamental, turf, vegetable, field, cereal, and fruit crops.

These pathogens may include:

Oomycetes, including *Phytophthora* diseases such as those caused by *Phytophthora capsici, Phytophthora infestans, Phytophthora sojae, Phytophthora fragariae, Phytophthora nicotianae, Phytophthora cinnamomi, Phytophthora citricola, Phytophthora citrophthora* and *Phytophthora erythroseptica*; *Pythium* diseases such as those caused by *Pythium aphanidermatum, Pythium arrhenomanes, Pythium graminicola, Pythium irregulare* and *Pythium ultimum*; diseases caused by Peronosporales such as *Peronospora destructor, Peronospora parasitica, Plasmopara viticola, Plasmopara halstedii, Pseudoperonospora cubensis, Albugo candida, Sclerophthora macrospora* and *Bremia lactucae*; and others such as *Aphanomyces cochlioides, Labyrinthula zosterae, Peronosclerospora sorghi* and *Sclerospora graminicola*;

Ascomycetes, including blotch, spot, blast or blight diseases and/or rots for example those caused by Pleosporales such as *Stemphylium solani, Stagonospora tainanensis, Spilocaea oleaginea, Setosphaeria turcica, Pyrenochaeta lycoperisici, Pleospora herbarum, Phoma destructive, Phaeosphaeria herpotrichoides, Phaeocryptocus gaeumannii, Ophiosphaerella graminicola, Ophiobolus graminis, Leptosphaeria maculans, Hendersonia creberrima, Helminthosporium triticirepentis, Setosphaeria turcica, Drechslera glycines, Didymella bryoniae, Cycloconium oleagineum, Corynespora cassiicola, Cochliobolus sativus, Bipolaris cactivora, Venturia inaequalis, Pyrenophora teres, Pyrenophora tritici-repentis, Alternaria alternata, Alternaria brassicicola, Alternaria solani* and *Alternaria tomatophila*, Capnodiales such as *Septoria tritici, Septoria nodorum, Septoria glycines, Cercospora arachidicola, Cercospora sojina, Cercospora zeae-maydis, Cercosporella capsellae* and *Cercosporella herpotrichoides, Cladosporium carpophilum, Cladosporium effusum, Passalora fulva, Cladosporium oxysporum, Dothistroma septosporum, Isariopsis clavispora, Mycosphaerella fijiensis, Mycosphaerella graminicola, Mycovellosiella koepkeii, Phaeoisariopsis bataticola, Pseudocercospora vitis, Pseudocercosporella herpotrichoides, Ramularia beticola, Ramularia collo-cygni*, Magnaporthales such as *Gaeumannomyces graminis, Magnaporthe grisea, Pyricularia oryzae*, Diaporthales such as *Anisogramma anomala, Apiognomonia errabunda, Cytospora platani, Diaporthe phaseolorum, Discula destructiva, Gnomonia fructicola, Greeneria uvicola, Melanconium juglandinum, Phomopsis viticola, Sirococcus clavigignenti-juglandacearum, Tubakia dryina, Dicarpella* spp., *Valsa ceratosperma*, and others such as *Actinothyrium graminis, Ascochyta pisi, Aspergillus flavus, Aspergillus fumigatus, Aspergillus nidulans, Asperisporium caricae, Blumeriella jaapii, Candida* spp., *Capnodium ramosum, Cephaloascus* spp., *Cephalosporium gramineum, Ceratocystis paradoxa, Chaetomium* spp., *Hymenoscyphus pseudoalbidus, Coccidioides* spp., *Cylindrosporium padi, Diplocarpon malae, Drepanopeziza campestris, Elsinoe ampelina, Epicoccum nigrum, Epidermophyton* spp., *Eutypa lata, Geotrichum candidum, Gibellina cerealis, Gloeocercospora sorghi, Gloeodes pomigena, Gloeosporium perennans; Gloeotinia temulenta, Griphospaeria corticola, Kabatiella lini, Leptographium microsporum, Leptosphaerulinia crassiasca, Lophodermium seditiosum, Marssonina graminicola, Microdochium nivale, Monilinia fructicola, Monographella albescens, Monosporascus cannonballus, Naemacyclus* spp., *Ophiostoma novo-ulmi, Paracoccidioides brasiliensis, Penicillium expansum, Pestalotia rhododendri, Petriellidium* spp., *Pezicula* spp., *Phialophora gregata, Phyllachora pomigena, Phymatotrichum omnivora, Physalospora abdita, Plectosporium tabacinum, Polyscytalum pustulans, Pseudopeziza medicaginis, Pyrenopeziza brassicae, Ramulispora sorghi, Rhabdocline pseudotsugae, Rhynchosporium secalis, Sacrocladium oryzae, Scedosporium* spp., *Schizothyrium pomi, Sclerotinia sclerotiorum, Sclerotinia minor; Sclerotium* spp., *Typhula ishikariensis, Seimatosporium mariae, Lepteutypa cupressi, Septocyta ruborum, Sphaceloma perseae, Sporonema phacidioides, Stigmina palmivora, Tapesia yallundae, Taphrina bullata, Thielviopsis basicola, Trichoseptoria fructigena, Zygophiala jamaicensis*; powdery mildew diseases for example those caused by Erysiphales such as *Blumeria graminis, Erysiphe polygoni, Uncinula necator, Sphaerotheca fuligena, Podosphaera leucotricha, Podospaera macularis Golovinomyces cichoracearum, Leveillula taurica, Microsphaera diffusa, Oidiopsis gossypii, Phyllactinia guttata* and *Oidium arachidis*; molds for example those caused by Botryosphaeriales such as *Dothiorella aromatica, Diplodia seriata, Guignardia bidwellii, Botrytis cinerea, Botryotinia allii, Botryotinia fabae, Fusicoccum amygdali, Lasiodiplodia theobromae, Macrophoma theicola, Macrophomina phaseolina, Phyllosticta cucurbitacearum*; anthracnoses for example those caused by Glommerelales such as *Colletotrichum gloeosporioides, Colletotrichum lagenarium, Colletotrichum gossypii, Glomerella cingulata*, and *Colletotrichum graminicola*; and wilts or blights for example those caused by Hypocreales such as *Acremonium strictum, Claviceps purpurea, Fusarium culmorum, Fusarium graminearum, Fusarium virguliforme, Fusarium oxysporum, Fusarium subglutinans, Fusarium oxysporum* f.sp. *cubense, Gerlachia nivale, Gibberella fujikuroi, Gibberella zeae, Gliocladium* spp., *Myrothecium verrucaria, Nectria ramulariae, Trichoderma viride, Trichothecium roseum*, and *Verticillium theobromae*;

Basidiomycetes, including smuts for example those caused by Ustilaginales such as *Ustilaginoidea virens, Ustilago nuda, Ustilago tritici, Ustilago zeae*, rusts for example those caused by Pucciniales such as *Cerotelium fici, Chrysomyxa arctostaphyli, Coleosporium ipomoeae, Hemileia vastatrix, Puccinia arachidis, Puccinia cacabata, Puccinia graminis, Puccinia recondita, Puccinia sorghi, Puccinia hordei, Puccinia striiformis* f.sp. *Hordei, Puccinia striiformis* f.sp. *Secalis, Pucciniastrum coryli*, or Uredinales such as *Cronartium ribicola, Gymnosporangium juniperi-viginianae, Melampsora medusae, Phakopsora pachyrhizi, Phragmidium mucronatum, Physopella ampelosidis, Tranzschelia discolor* and *Uromyces viciae-fabae*; and other rots and diseases such as those caused by *Cryptococcus* spp., *Exobasidium vexans, Marasmiellus inoderma, Mycena* spp., *Sphacelotheca reiliana, Typhula ishikariensis, Urocystis agropyri, Itersonilia perplexans, Corticium invisum, Laetisaria fuciformis, Waitea circinata, Rhizoctonia solani, Thanetephorus cucurmeris, Entyloma dahliae, Entylomella microspora, Neovossia moliniae* and *Tilletia caries*;

Blastocladiomycetes, such as *Physoderma maydis*;

Mucoromycetes, such as *Choanephora cucurbitarum; Mucor* spp.; *Rhizopus arrhizus*; as well as diseases caused by other species and genera closely related to those listed above.

In addition to their fungicidal activity, the compositions may also have activity against bacteria such as *Erwinia amylovora, Erwinia caratovora, Xanthomonas campestris, Pseudomonas syringae, Strptomyces scabies* and other related species as well as certain protozoa.

The composition according to the invention is particularly effective against phytopathogenic fungi belonging to the following classes: Ascomycetes (e.g. *Venturia, Podosphaera, Erysiphe, Monilinia, Mycosphaerella, Uncinula*); Basidiomycetes (e.g. the genus *Hemileia, Rhizoctonia, Phakopsora, Puccinia, Ustilago, Tilletia*); Fungi imperfecti (also known as *Deuteromycetes*; e.g. *Botrytis, Helminthosporium, Rhynchosporium, Fusarium, Septoria, Cercospora, Alternaria, Pyricularia* and *Pseudocercosporella*); Oomycetes (e.g. *Phytophthora, Peronospora, Pseudoperonospora, Albugo, Bremia, Pythium, Pseudosclerospora, Plasmopara*).

Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgraSciences, Pioneer Hi-Bred International).

The compounds of Formula (I) (including any one of compounds X.01 to X.25) or fungicidal compositions according to the present invention comprising a compound of Formula (I) may be used in controlling or preventing phytopathogenic diseases, especially phytopathogenic fungi (such as *Phakopsora pachyrhizi*) on soy bean plants.

In particular, transgenic soybean plants expressing toxins, for example insecticidal proteins such as delta-endotoxins, e.g. Cry1Ac (Cry1Ac Bt protein). Accordingly, this may include transgenic soybean plants comprising event MON87701 (see U.S. Pat. No. 8,049,071 and related applications and patents, as well as WO 2014/170327 A1 (eg, see paragraph [008] reference to Intacta RR2 PRO™ soybean)), event MON87751 (U.S. Patent Application Publication No. 2014/0373191) or event DAS-81419 (U.S. Pat. No. 8,632, 978 and related applications and patents).

Other transgenic soybean plants may comprise event SYHT0H2—HPPD tolerance (U.S. Patent Application Publication No. 2014/0201860 and related applications and patents), event MON89788—glyphosate tolerance (U.S. Pat. No. 7,632,985 and related applications and patents), event MON87708—dicamba tolerance (U.S. Patent Application Publication No. US 2011/0067134 and related applications and patents), event DP-356043-5—glyphosate and ALS tolerance (U.S. Patent Application Publication No. US 2010/0184079 and related applications and patents), event A2704-12—glufosinate tolerance (U.S. Patent Application Publication No. US 2008/0320616 and related applications and patents), event DP-305423-1—ALS tolerance (U.S. Patent Application Publication No. US 2008/0312082 and related applications and patents), event A5547-127—glufosinate tolerance (U.S. Patent Application Publication No. US 2008/0196127 and related applications and patents), event DAS-40278-9—tolerance to 2,4-dichlorophenoxyacetic acid and aryloxyphenoxypropionate (see WO 2011/022469, WO 2011/022470, WO 2011/022471, and related applications and patents), event 127—ALS tolerance (WO 2010/080829 and related applications and patents), event GTS 40-3-2—glyphosate tolerance, event DAS-68416-4-2,4-dichlorophenoxyacetic acid and glufosinate tolerance, event FG72—glyphosate and isoxaflutole tolerance, event BPS-CV127-9—ALS tolerance and GU262—glufosinate tolerance or event SYHT04R—HPPD tolerance.

The compounds of Formula (I) (including any one of compounds X.01 to X.25) or fungicidal compositions according to the present invention comprising a compound of Formula (I) may be used in controlling or preventing phytopathogenic diseases, especially phytopathogenic fungi (such as *Phakopsora pachyrhizi*) on soy bean plants. In particular, there are known in the scientific literature certain Elite soybean plant varieties where R-gene stacks, conferring a degree of immunity or resistance to specific *Phakopsora pachyrhizi*, have been been introgressed in the plant genome, see for example: "*Fighting Asian Soybean Rust*", Langenbach C, et al, *Front Plant Science* 7(797) 2016).

An elite plant is any plant from an elite line, such that an elite plant is a representative plant from an elite variety. Non-limiting examples of elite soybean varieties that are commercially available to farmers or soybean breeders include: AG00802, A0868, AG0902, A1923, AG2403, A2824, A3704, A4324, A5404, AG5903, AG6202 AG0934; AG1435; AG2031; AG2035; AG2433; AG2733; AG2933; AG3334; AG3832; AG4135; AG4632; AG4934; AG5831; AG6534; and AG7231 (Asgrow Seeds, Des Moines, Iowa, USA); BPRO144RR, BPR 4077NRR and BPR 4390NRR (Bio Plant Research, Camp Point, Ill., USA); DKB17-51 and DKB37-51 (DeKalb Genetics, DeKalb, Ill., USA); DP 4546 RR, and DP 7870 RR (Delta & Pine Land Company, Lubbock, Tex., USA); JG 03R501, JG 32R606C ADD and JG 55R503C (JGL Inc., Greencastle, Ind., USA); NKS 13-K2 (NK Division of Syngenta Seeds, Golden Valley, Minn., USA); 90M01, 91M30, 92M33, 93M11, 94M30, 95M30, 97B52, P008T22R2; P16T17R2; P22T69R; P25T51R; P34T07R2; P35T58R; P39T67R; P47T36R; P46T21R; and P56T03R2 (Pioneer Hi-Bred International, Johnston, Iowa, USA); SG4771NRR and SG5161NRR/STS (Soygenetics, LLC, Lafayette, Ind., USA); S00-K5, S11-L2, S28-Y2, S43-131, S53-A1, S76-L9, S78-G6, S0009-M2; S007-Y4; S04-D3; S14-A6; S20-T6; S21-M7; S26-P3; S28-N6; S30-V6; S35-C3; S36-Y6; S39-C4; S47-K5; S48-D9; S52-Y2; S58-Z4; S67-R6; S73-S8; and S78-G6 (Syngenta Seeds, Henderson, Ky., USA); Richer (Northstar Seed Ltd. Alberta, CA); 14RD62 (Stine Seed Co. Ia., USA); or Armor 4744 (Armor Seed, LLC, Ar., USA).

Thus, in a further preferred embodiment, the compounds of Formula (I) (including any one of compounds X.01 to X.25), or fungicidal compositions according to the present invention comprising a compound of Formula (I), are used to control *Phakopsora pachyrhizi*, (including fungicidally-resistant strains thereof, as outlined below) on Elite soybean plant varieties where R-gene stacks, conferring a degree of immunity or resistance to specific *Phakopsora pachyrhizi*, have been been introgressed in the plant genome. Numerous benefits may be expected to ensue from said use, e.g. improved biological activity, an advantageous or broader spectrum of activity (inc. sensitive and resistant strains of *Phakopsora pachyrhizi*), an increased safety profile, improved crop tolerance, synergistic interactions or potentiating properties, improved onset of action or a longer lasting residual activity, a reduction in the number of applications and/or a reduction in the application rate of the compounds and compositions required for effective control of the phytopathogen (*Phakopsora pachyrhizi*), thereby enabling beneficial resistance-management practices, reduced environmental impact and reduced operator exposure.

Under certain circumstances, fungicidal compositions according to the present invention comprising a compound of Formula (I) when used in controlling or preventing phytopathogenic diseases, especially phytopathogenic fungi (such as *Phakopsora pachyrhizi*) on soy bean plants (in particular any of the transgenic soybean plants as described above), may display a synergistic interaction between the active ingredients.

The compounds of Formula (I) (including any one of compounds X.01 to X.25) or fungicidal compositions according to the present invention comprising a compound of Formula (I) may be used in controlling or preventing phytopathogenic diseases, especially phytopathogenic fungi (in particular, *Phakopsora pachyrhizi*) on soybean plants.

Additionally, to date, no cross-resistance has been observed between the compounds of Formula (I) (including any one of compounds X.01 to X.25) and the current fungicidal solutions used to control *Phakopsora pachyrhizi*.

Indeed, fungicidal-resistant strains of *Phakopsora pachyrhizi* have been reported in the scientific literature, with strains resistant to one or more fungicides from at least each of the following fungicidal mode of action classes being observed: sterol demethylation-inhibitors (DMI), quinone-outside-inhibitors (QoI) and succinate dehydrogenase inhibitors (SDHI). See for example: "Sensitivity of *Phakopsora pachyrhizi* towards quinone-outside-inhibitors and demethylation-inhibitors, and corresponding resistance mechanisms." Schmitz H K et al, *Pest Manag Sci* (2014) 70: 378-388; "First detection of a SDH variant with reduced SDHI sensitivity in *Phakopsora pachyrhizi*" Simões K et al, *J Plant Dis Prot* (2018) 125: 21-2; "Competitive fitness of *Phakopsora pachyrhizi* isolates with mutations in the CYP51 and CYTB genes." Klosowski A C et al, *Phytopathology* (2016) 106: 1278-1284; "Detection of the F129L mutation in the cytochrome b gene in *Phakopsora pachyrhizi*." Klosowski A C et al, *Pest Manag Sci* (2016) 72: 1211-1215.

Thus, in a preferred embodiment, the compounds of Formula (I) (including any one of compounds X.01 to X.25), or fungicidal compositions according to the present invention comprising a compound of Formula (I), are used to control *Phakopsora pachyrhizi* which are resistant to one or more fungicides from any of the following fungicidal MoA classes: sterol demethylation-inhibitors (DMI), quinone-outside-inhibitors (QoI) and succinate dehydrogenase inhibitors (SDHI).

It is understood that when in aqueous media, the compounds of formula (I) according to the invention may be present in a reversible equilibrium with the corresponding covalently hydrated forms (ie, the compounds of formula (I-Ia) and formula (I-IIa) as shown below, which may exist in tautomeric form as the compounds of formula (I-Ib) and formula (I-IIb)) at the $CF_3$-oxadiazole motif. This dynamic equilibrium may be important for the biological activity of the compounds of Formula (I). The designations $R^1$, $R^2$, $R^3$, $R^4$, $R^5$, $R^6$, and $R^7$ with reference to the compounds of formula (I) of the present invention apply generally to the compounds of Formula (I-Ia), Formula (I-IIa), Formula (I-Ib), and Formula (I-IIb), as do the specific disclosures of combinations of $R^1$, $R^2$, $R^3$, $R^4$, $R^5$, $R^6$, and $R^7$ as represented in the compounds X.01 to X.25 described in Table X (above) or Table T1 (below).

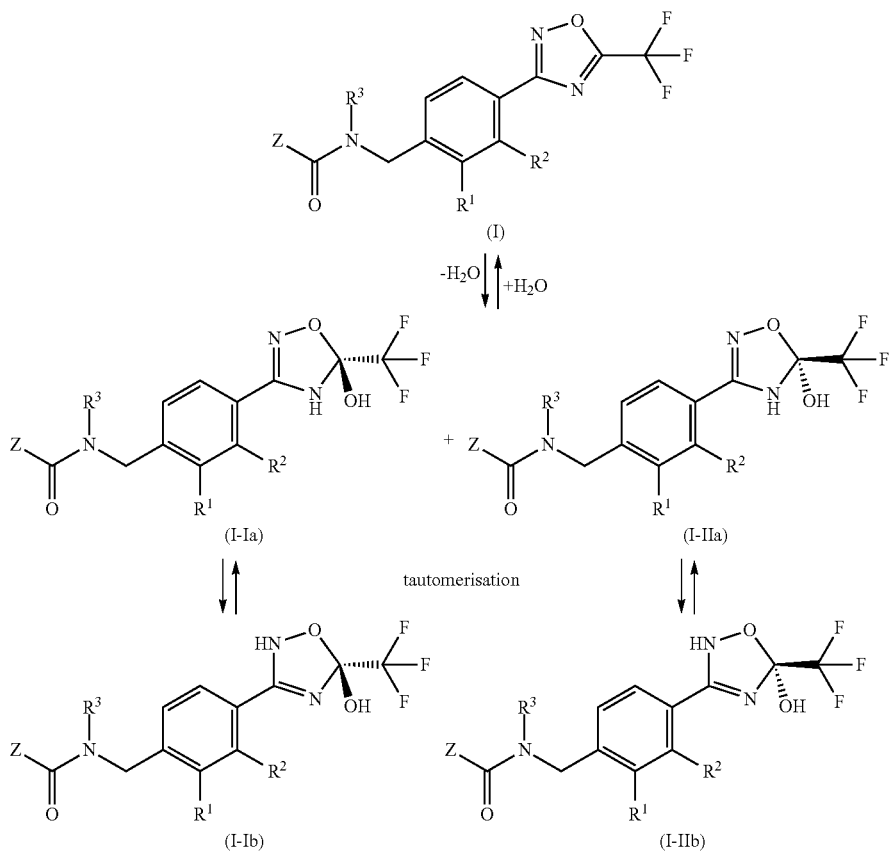

Compounds of formula (I) used in accordance with the present invention can be made as shown in the following schemes 1 to 29, in which, unless otherwise stated, the definition of each variable is as defined herein for a compound of formula (I).

The compounds of formula (I) can be obtained via coupling transformations with compounds of formula (II) and compounds of formula (III), wherein X is halogen, ester [eg, OMe or OEt)], anhydride [eg, OC(H)O, or OAc], or OH, preferably halogen, in a suitable solvent (eg, dimethylformamide, dichloromethane, or tetrahydrofuran), preferably at temperatures between 25° C. and 100° C., and optionally in the presence of a base (eg, NaHCO$_3$, Na$_2$CO$_3$, K$_2$CO$_3$, NaOH, triethylamine or N,N-diisopropylethylamine), or under conditions described in the literature for an amide or urea coupling, for example by using BOP-Cl or HATU. For examples, see WO 2003/028729, WO 2013/092943, WO 2017/055473, or WO 2014/025128. Furthermore, compounds of formula (I), wherein Z represents —R$^4$, can optionally be obtained via coupling transformations with compounds of formula (II) and compounds of formula (III), wherein X is —OH, via processes that convert the —OH into an improved halide leaving group, such as a chloride, for example by using triphosgene, diphosgene, phosgene, (COCl)$_2$, or SOCl$_2$, prior to treatment with the compounds of formula (II). Compounds of formula (III) are commercially available or prepared using known methods. For related examples, see: Nelson, T. D et al *Tetrahedron Lett.* (2004), 45, 8917; Senthil, K. et al *Pest. Res. Journal* (2009), 21, 133; and Crich, D., Zou, Y. *J. Org. Chem.* (2005), 70, 3309. This reaction is shown in Scheme 1.

Scheme 1

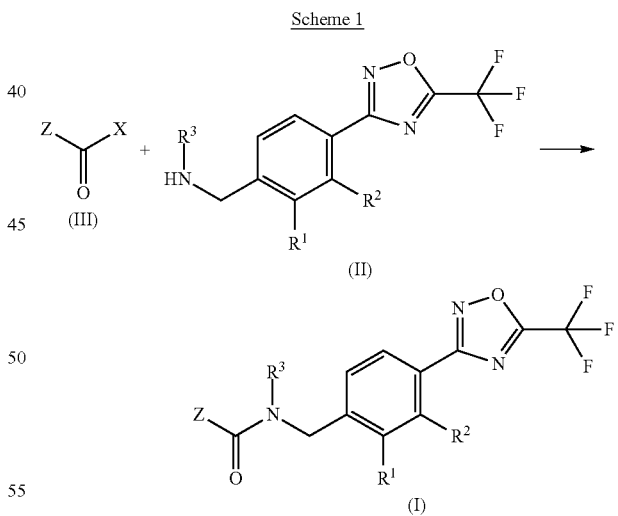

Alternatively, compounds of formula (I), wherein Z represents —R$^4$, can be prepared via reactions with compounds of formula (II) with triphosgene, diphosgene, or phosgene in a suitable solvent (eg, ethyl acetate, chloroform, acetone, or toluene), followed by a reaction with nucleophiles of formula (IV), wherein Z-Nu represents an R$^4$-Metal organometallic reagent (eg, an organomagnesium, organozinc, or organolithium), in a suitable solvent (eg, toluene, diethyl ether or tetrahydrofuran), at temperatures between −78° C. and 25° C. For related examples, see Charalambides, Y. C., Moratti, S. C. *Synth. Commun.* (2007), 37, 1037; Schaefer, G. et al *Angew. Chem., Int. Ed.* (2012) 51, 9173; Lengyel, I. et al *Heterocycles* (2007), 73, 349; and Benalil, A. et al *Synthesis* (1991), 9, 787. Furthermore, compounds of formula (I), wherein Z represents —NR[6]R[7], can be prepared via reactions with compounds of formula (II) with triphosgene, diphosgene, or phosgene in a suitable solvent (eg, 1,2-dichloroethane, acetonitrile, ethyl acetate, chloroform, or toluene) followed by the addition of nucleophiles of formula (IV), wherein Z-Nu represents HNR[6]R[7], in the presence of a suitable base, such as pyridine, $K_2CO_3$, or triethylamine. For related examples, see WO 2017/055473. This reaction is shown in Scheme 2.

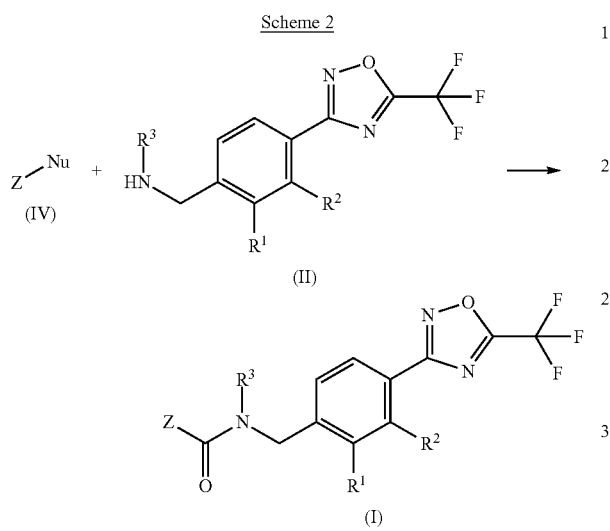

Additionally, compounds of formula (I) can be prepared from compounds of formula (V) via reactions with trifluoroacetic acid, trifluoroacetic ester, trifluoroacetic anhydride, or trifluoroacetyl halide (including trifluoroacetyl fluoride, trifluoroacetyl chloride and trifluoroacetyl bromide), optionally in the presence of a base (eg, pyridine or 4-dimethylaminopyridine) in a suitable solvent, (eg, toluene, ethyl acetate, tetrahydrofuran, 2-methyl tetrahydrofuran, or ethanol), at temperatures between 0° C. and 75° C. For related examples, see WO 2003/028729, WO 2017/055473, and WO 2010/045251. This reaction is shown in Scheme 3.

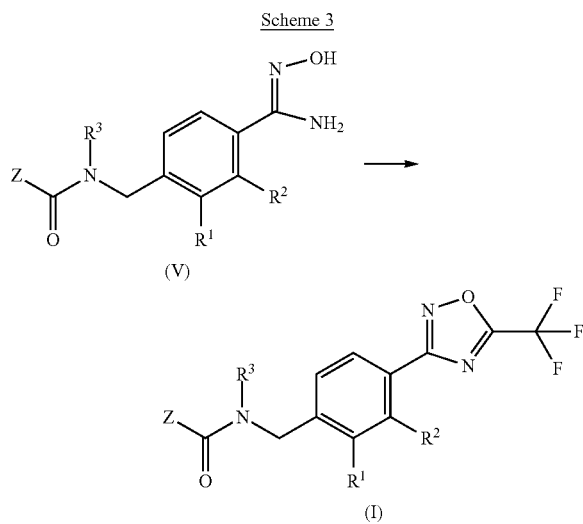

Compounds of formula (V) can be prepared from compounds of formula (VI) via reactions with a hydroxylamine hydrochloride salt or a hydroxylamine solution in water, in the presence of a base, such as triethylamine or potassium carbonate, in a suitable solvent, such as methanol or ethanol, at temperatures between 0° C. and 80° C. In some cases, a better reaction performance may be gained from the use of a catalyst (eg, 8-hydroxyquinoline). For related examples, see Kitamura, S. et al *Chem. Pharm. Bull.* (2001), 49, 268, WO 2017/055473 and WO 2013/066838. This reaction is shown in Scheme 4.

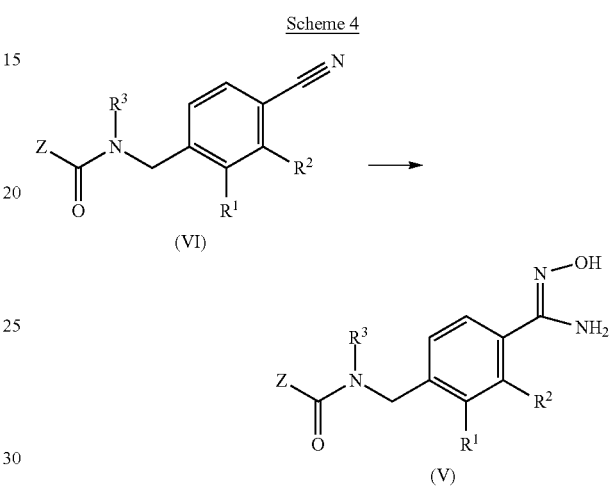

Compounds of formula (VI) are commercially available or can be prepared from compounds of formula (VII), wherein Y is formyl, Cl, Br, or I, via metal-promoted reactions with a suitable cyanide reagent, such as acetone cyanohydrin, dimethylmalononitrile, $K_4[Fe(CN)_6]$, $Zn(CN)_2$, NaCN, or CuCN, in a suitable solvent (eg, dimethylformamide or N-methylpyrrolidone) at elevated temperatures between 80° C. and 120° C., and optionally in the presence of a metal catalyst (eg, Pd or Ni) or a Grignard or organolithium reagent. For related examples, see Reeves, J. T. et al *J. Am. Chem. Soc.*, (2015), 137, 9481-9488, Ushijima, S., Togo, H. *Synlett*, (2010), 1067, US 2007/0155739, WO 2017/055473, and WO 2009/022746.

Alternatively, compounds of formula (VI) can be prepared from compounds of formula (VII), wherein Y is $NH_2$, via radical-nucleophilic aromatic substitution reactions in the presence of a nitrite source (eg, $NaNO_2$ or iso-amylnitrite), an acid (eg, hydrochloric acid or $HBF_4$), and a copper source (eg, CuCN) in an acceptable solvent system, such as aqueous acetonitrile, at suitable temperatures (eg, 0° C. to 100° C.). For related examples, see Wen, Q. et al. *Tet. Lett.* (2014), 55, 1271. This reaction is shown in Scheme 5.

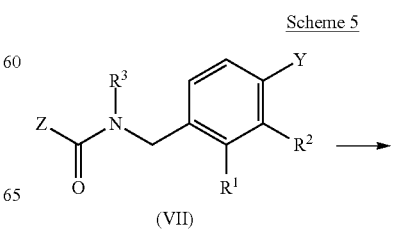

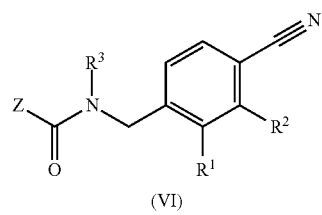

(VI)

Compounds of formula (VII), wherein Z represents $R^4$ and Y is Cl, Br, I, or CN and the N—$R^3$ bond contains a directly linked unsaturated methylene segment [eg, —$CH_2$— or —$CH(CH_3)$—], can be prepared from compounds of formula (VIII), via reactions using a suitable base (eg, sodium hydride) and a suitable alkyl halide alkylating reagent (eg, methyl iodide, ethyl iodide, 2,2,2-trifluoroethyl iodide, 2-methoxyethyl iodide, or isopropyl iodide), in a suitable solvent (eg, dimethylformamide or N-methylpyrrolidone) at elevated temperatures between 60° C. and 120° C. This reaction is shown in Scheme 6.

Scheme 6

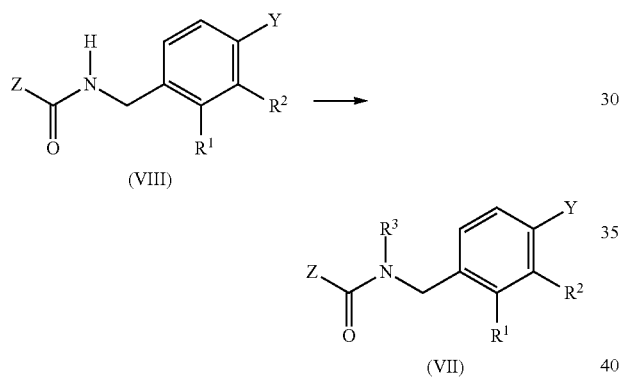

(VIII)

(VII)

Compounds of formula (II) can be prepared from aldehyde compounds of formula (X), via condensation reactions with amines of formula (IX), in a suitable solvent, (eg, tetrahydrofuran or methanol) at temperatures between 25° C. and 75° C., followed by the addition of a reducing reagent, such as $NaBH_3CN$, in a suitable solvent, (eg, tetrahydrofuran or ethanol) at temperatures between 0° C. and 25° C. For related examples, see Gazzola, C. and Kenyon, G. L. *Journal of Labeled Compounds and Radiopharmaceuticals*, (1978), 15, 181 and WO 2017/055473. This reaction is shown in Scheme 7.

Scheme 7

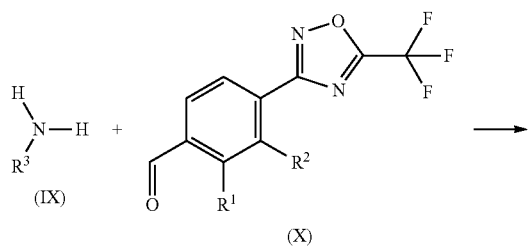

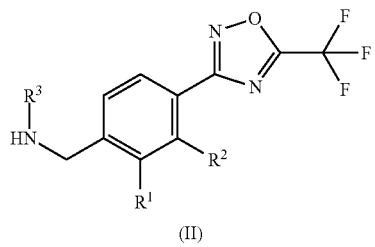

(II)

Alternatively, compounds of formula (II), can be prepared from compounds of formula (XI), wherein X is Cl, Br, I, or $OSO_2Me$, via reactions of amines of formula (IX), optionally in the presence of a base (eg, triethylamine), in a suitable solvent (eg, tetrahydrofuran) at temperatures between 25° C. and 60° C. For related examples, see Miyawaki, K. et al *Heterocycles* (2001), 54, 887; WO 2003/028729, WO 2017/055473, and WO 2013/066839. This reaction is shown in Scheme 8.

Scheme 8

(IX) + (XI) →

(II)

Compounds of formula (XI), wherein X is Cl or Br, can be prepared from compounds of formula (XII), via reactions with a halogen source (eg, N-bromosuccinimide (NBS) or N-chlorosuccinimide (NCS)) and a radical initiator (eg, $(PhCO_2)_2$ or azobisisobutyronitrile (AIBN)) in a suitable solvent, such as tetrachloromethane, at temperatures between 55° C. and 100° C., optionally in the presence of ultraviolet light. For related examples, see WO 2017/055473; Liu, S. et al *Synthesis* (2001), 14, 2078; and Kompella, A. et al *Org. Proc. Res. Dev.* (2012), 16, 1794. This reaction is shown in Scheme 9.

Scheme 9

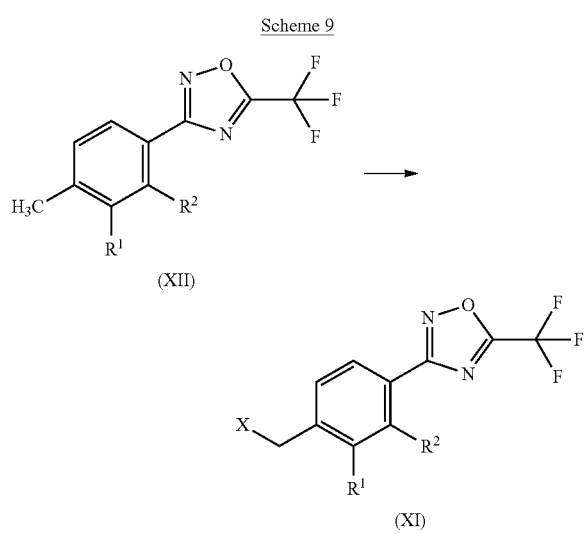

The compounds of formula (VII), wherein Y is formyl, NH₂, Cl, Br, I, or CN, can be obtained via coupling transformations with compounds of formula (XIII) and compounds of formula (III), wherein X is halogen, ester [eg, OMe or OEt)], anhydride [eg, OC(H)O, or OAc], or OH, preferably halogen in a suitable solvent (eg, dimethylformamide, dichloromethane, tetrahydrofuran, or 2-methyl tetrahydrofuran), preferably at temperatures between 0° C. and 100° C., and optionally in the presence of a base (eg, NaHCO₃, Na₂CO₃, K₂CO₃, NaOH, triethylamine or N,N-diisopropylethylamine), or under conditions described in the literature for an amide or urea coupling, for example by using BOP-Cl or HATU. Furthermore, compounds of formula (VII), wherein Z represents R⁴, can optionally be obtained via coupling transformations with compounds of formula (XIII) and compounds of formula (III), wherein X is OH, via processes that converts the —OH into an improved halide leaving group, such as a chloride, for example by using triphosgene, diphosgene, or phosgene, (COCl)₂, or SOCl₂, prior to treatment with the compounds of formula (XIII). For examples, see WO 2003/028729, WO 2013/092943, WO 2017/055473, or WO 2014/025128. Compounds of formula (III) are commercially available or prepared using known methods. For related examples, see: Nelson, T. D et al *Tetrahedron Lett.* (2004), 45, 8917; Senthil, K. et al *Pest. Res. Journal* (2009), 21, 133; and Crich, D., Zou, Y. *J. Org. Chem.* (2005), 70, 3309. This reaction is shown in Scheme 10.

Scheme 10

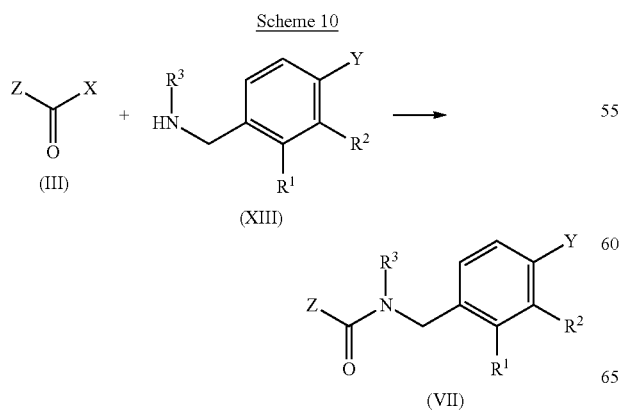

Alternatively, compounds of formula (VII), wherein Y is NH₂, Cl, Br, I, or CN and Z represents —R⁴, can be prepared via reactions with compounds of formula (XIII) with triphosgene, diphosgene, or phosgene in a suitable solvent (eg, ethyl acetate, acetone, chloroform, or toluene), followed by a reaction with nucleophiles of formula (IV), wherein Z-Nu represents an R⁴-Metal organometallic reagent (eg, an organomagnesium, organozinc, or organolithium), in a suitable solvent (eg, toluene, diethyl ether, or tetrahydrofuran), at temperatures between −78° C. and 25° C. For related examples, see Charalambides, Y. C., Moratti, S. C. *Synth. Commun.* (2007), 37, 1037; Schaefer, G. et al *Angew. Chem., Int. Ed.* (2012) 51, 9173; Lengyel, I. et al *Heterocycles* (2007), 73, 349; and Benalil, A et al *Synthesis* (1991), 9, 787. This reaction is shown in Scheme 11.

Furthermore, compounds of formula (VII), wherein Z represents —NR⁶R⁷, can be prepared via reactions with compounds of formula (XIII) with triphosgene, diphosgene, or phosgene in a suitable solvent (eg, 1,2-dichloroethane, water, acetonitrile, ethyl acetate, chloroform, or toluene), followed by the addition of suitable nucleophiles of formula (IV), wherein Z-Nu represents HNR⁶R⁷, and in the presence of a suitable base, such as pyridine, K₂CO₃, or triethylamine. This reaction is shown in Scheme 11.

Scheme 11

Compounds of formula (XIII), wherein Y is formyl, NH₂, Cl, Br, I, or CN, can be prepared from compounds of formula (XIV), wherein X is Cl, Br, I, or OSO₂Me, via reactions of amines of formula (IX), in the presence of a suitable base (eg, NaHCO₃, Na₂CO₃, K₂CO₃, or NaH) in a suitable solvent, (eg, dimethylformamide, N-methylpyrolidine, or acetonitrile) at temperatures between 0° C. and 100° C. In some cases, an improved reaction performance may be gained via use of a catalyst (eg, Bu₄NHSO₄, Bu₄NBr, Bu₄NI, NaI, or 4-dimethylaminopyridine) or optionally with microwaves irradiation. For related examples, see Miyawaki, K. et al *Heterocycles* (2001), 54, 887. This reaction is shown in Scheme 12.

Scheme 12

-continued

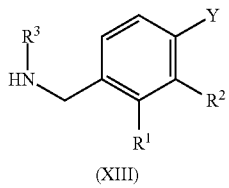

(XIII)

Compounds of formula (XIV), wherein Y is formyl, $NH_2$, Cl, Br, I, or CN and X is Cl or Br are either commercially available or can be prepared from compounds of formula (XV), via reactions with a halogen source, [eg, N-bromosuccinimide (NBS) or N-chlorosuccinimide (NCS)] and a radical initiator, such as $(PhCO_2)_2$ or azobisisobutyronitrile (AIBN), optionally in the presence of ultraviolet light, in a suitable solvent, such as tetrachloromethane, at temperatures between 55° C. and 100° C. For related examples, see Liu, S. et al *Synthesis* (2001), 14, 2078 and Kompella, A. et al *Org. Proc. Res. Dev.* (2012), 16, 1794. This reaction is shown in Scheme 13.

Scheme 13

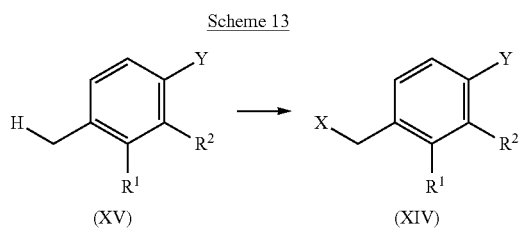

Alternatively, compounds of formula (XIV), wherein X is Cl, Br, I, or $OSO_2Me$ and Y is formyl, $NH_2$, Cl, Br, I, CN, or (5-(trifluoromethyl)-1,2,4-oxadiazole), are either commercially available or can be prepared from compounds of formula (XVI), via reactions with an acid source (eg, hydrochloric acid, hydrobromic acid, or hydroiodic acid) or a halogen source (eg, tetrabromomethane, tetrachloromethane, or iodine) in the presence of triphenylphosphine, or with methanesulfonyl chloride ($ClSO_2Me$), in a suitable solvent (eg, dichloromethane), in the presence of a base (eg, triethylamine), at temperatures between 0° C. and 100° C. For related examples, see Liu, H. et al *Bioorg. Med. Chem.* (2008), 16, 10013, WO 2014/020350 and Kompella, A. et al *Bioorg. Med. Chem. Lett.* (2001), 1, 3161. Compounds of formula (XVI) are commercially available. This reaction is shown in Scheme 14.

Scheme 14

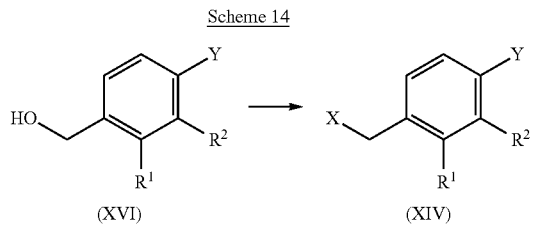

Furthermore, compounds of formula (VII), wherein Y is formyl, $NH_2$, Cl, Br, I, or CN, can be prepared from compounds of formula (XIV), wherein X is is a suitable leaving group (eg, Cl, Br, I, OH, or $OSO_2Me$) via reactions with amides or ureas of formula (XVII) in the presence of a base (eg, triethylamine, N,N-diisopropylethylamine, $K_2CO_3$, $NaHCO_3$, or $Na_2CO_3$) in a suitable solvent (eg, dimethylacetamide, tetrahydrofuran, 2-methyltetrahydrofuran, acetone, or acetonitrile) at temperatures between 0° C. and 90° C. In some cases, a better reaction performance may be gained from the use of a catalyst (eg, $Bu_4NHSO_4$, $Bu_4NBr$, $Bu_4NI$, NaI, or 4-dimethylaminopyridine) or optionally with microwaves irradiation. For related examples, see Miyawaki, K. et al *Heterocycles* (2001), 54, 887, WO 2003/028729, and WO 2013/066839. This reaction is shown in Scheme 15.

Scheme 15

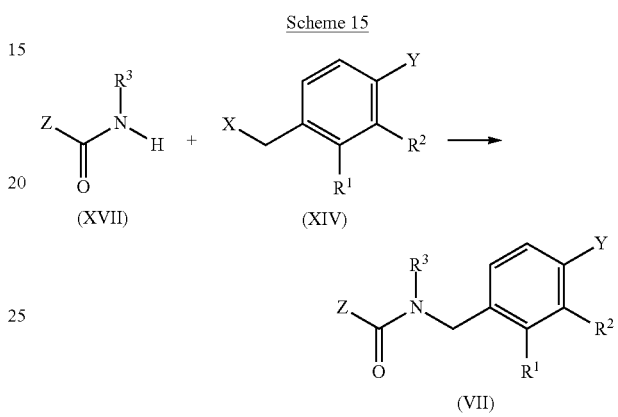

Compounds of formula (XVII), wherein Z represents $—NR^6R^7$, can be prepared from amine compounds of formula (IX) via reactions with triphosgene, diphosgene, or phosgene, optionally in a suitable solvent (eg, water, acetonitrile, ethyl acetate, tetrahydrofuran, chloroform, or toluene) followed by the addition of a nucleophile of formula (IV), wherein Z-Nu represents $HNR^6R^7$, in the presence of a base (eg, pyridine, triethylamine, $K_2CO_3$, $NaHCO_3$, or $Na_2CO_3$), and at temperatures between 0° C. and 25° C. This reaction is shown in Scheme 16.

Scheme 16

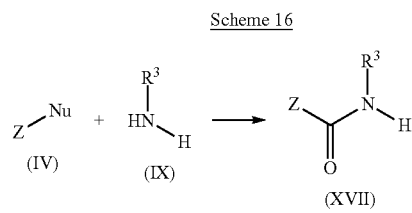

Alternatively, the compounds of formula (XVII), can be obtained through a coupling transformation with amine compounds of formula (IX) and compounds of formula (III), wherein X is halogen, ester [eg, OMe or OEt)], anhydride [eg, OC(H)O, or OAc], or OH, preferably halogen, in a suitable solvent (eg, dimethylformamide, acetonitrile, dichloromethane or tetrahydrofuran), preferably at temperatures between 25° C. and 100° C., and optionally in the presence of a base (eg, $K_2CO_3$, triethylamine, or N,N-diisopropylethylamine), or under conditions described in the literature for an amide or urea coupling, for example by using BOP-Cl or HATU. For examples, see WO 2003/028729. This reaction is shown in Scheme 17.

Furthermore, compounds of formula (XVII), wherein Z represents $R^4$, can optionally be obtained via coupling transformations with compounds of formula (IX) and compounds of formula (III), wherein X is OH, via processes that convert the —OH into an improved halide leaving group, such as a chloride, for example by using triphosgene, diphosgene, phosgene, (COCl)$_2$, or SOCl$_2$, prior to treatment with the compounds of formula (IX). Compounds of formula (III) are commercially available or prepared using known methods. For related examples, see Nelson, T. D et al *Tetrahedron Lett.* (2004), 45, 8917; Senthil, K. et al *Pest. Res. Journal* (2009), 21, 133; and Crich, D., Zou, Y. *J. Org. Chem.* (2005), 70, 3309. This reaction is shown in Scheme 17.

Scheme 17

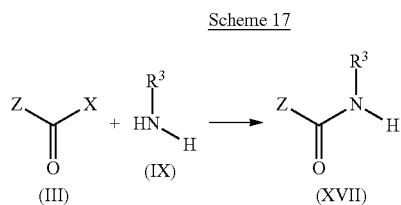

Furthermore, compounds of formula (I) can be prepared from compounds of formula (XI), wherein X is a suitable leaving group (eg, Cl, Br, I, OH, or OSO$_2$Me), via reactions with amides or ureas of formula (XVII), optionally in the presence of a base (eg, triethylamine, N,N-diisopropylethylamine, K$_2$CO$_3$, NaHCO$_3$, or Na$_2$CO$_3$) in a suitable solvent (eg, dimethylacetamide, tetrahydrofuran, 2-methyltetrahydrofuran, acetone, toluene, or acetonitrile) at temperatures between 0° C. and 90° C. In some cases, a better reaction performance may be gained by the use of a catalyst (eg, Bu$_4$NHSO$_4$, Bu$_4$NBr, Bu$_4$NI, NaI, or 4-dimethylaminopyridine) and optionally with microwaves irradiation. For related examples, see Miyawaki, K. et al *Heterocycles* (2001), 54, 887, WO 2003/028729, and WO 2013/066839. This reaction is shown in Scheme 18.

Scheme 18

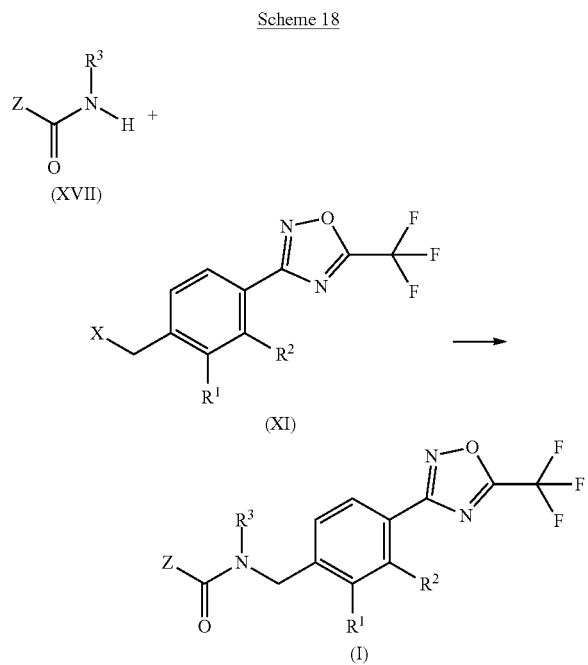

Compounds of formula (XIII), wherein Y is F, Cl, Br, CN, or 5-(trifluoromethyl)-1,2,4-oxadiazol-3-yl, can be prepared from compounds of formula (XIX), wherein X is Cl, Br, or I, and an imine of formula (XVIII), in the presence of a suitable acid (eg, BF$_3$·OEt$_2$) via introducing a suitable organometallic species (eg, i-PrMgCl.LiCl, EtZnCl, or n-BuLi) in a suitable solvent (eg, tetrahydrofuran or diethyl ether) at temperatures between −78° C. and 25° C. For related examples, see: *Tet. Lett.* (1986), 27, 1549; Kostyanovsky, R. G. et al *Tetrahedron* (1981), 37, 4245. This reaction is shown in Scheme 19.

Alternatively, compounds of formula (XIII), wherein Y is formyl, F, Cl, Br, CN, or 5-(trifluoromethyl)-1,2,4-oxadiazol-3-yl, can be prepared from compounds of formula (XIX), wherein X is NH$_2$, and an imine of formula (XVIII) via radical additions in a suitable solvent, such as aqueous methanol. For related examples, see Hart, D. J., Seely, F. L. *J. Am. Chem. Soc.* (1988), 110, 1631; Miyabe, H. *Tetrahedron* (1998), 54, 11431; Hideto, M. *J. Org. Chem.* (2000), 65, 5043. This reaction is shown in Scheme 19.

Scheme 19

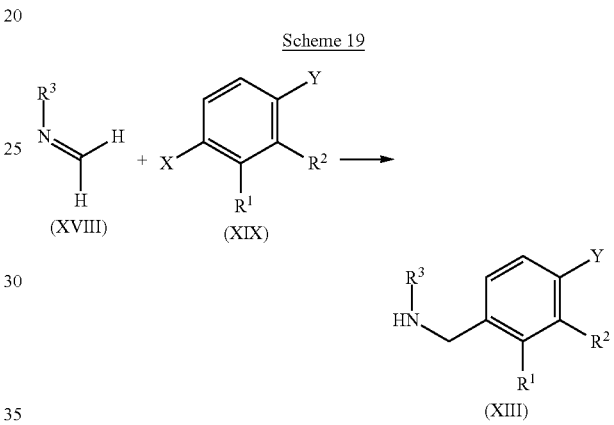

Moreover, compounds of formula (VII), wherein Y is formyl, F, Cl, Br, I, CN or 5-(trifluoromethyl)-1,2,4-oxadiazol-3-yl, can be prepared from compounds of formula (XIX), wherein X is methyl, via reactions with amides or ureas of formula (XVII) via photo-redox amination reactions using a light emitting diode (LED) visible light source, in a suitable solvent (eg, acetonitrile), in the presence of an electron acceptor catalyst (eg, 9,10-dicyanoanthracene) at temperatures between 25° C. and 75° C. For related examples, see Pandey, G., Laha, R. *Angew. Chem. Int. Ed.* (2015), 54, 14875. This reaction is shown in Scheme 20.

Scheme 20

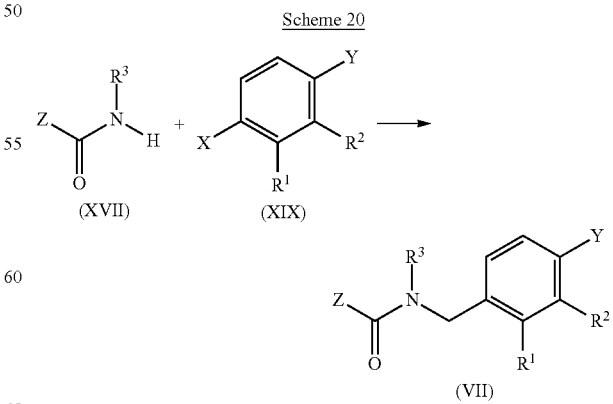

Compounds of formula (XIII), wherein Y is F, Cl, Br, CN, or 5-(trifluoromethyl)-1,2,4-oxadiazol-3-yl, can be prepared from compounds of formula (XIX), wherein X is Cl, Br, or I, a formamide of formula (XX), and an activating reagent, (eg, POCl$_3$, PCl$_3$, COCl$_2$, PhSO$_2$Cl, Me$_2$NSO$_2$Cl, (CF$_3$CO)$_2$O or (MeO)$_2$SO$_2$), via introducing a suitable organometallic species (eg, i-PrMgCl.LiCl, EtZnCl, or n-BuLi) in a suitable solvent (eg, ethanol, acetonitrile, tetrahydrofuran, or diethyl ether), at temperatures between −35° C. and 25° C. followed by the addition of a suitable reducing reagent, such as NaBH$_3$CN, in a suitable solvent (eg, tetrahydrofuran or ethanol) at temperatures between 0° C. and 25° C. This reaction is shown in Scheme 21.

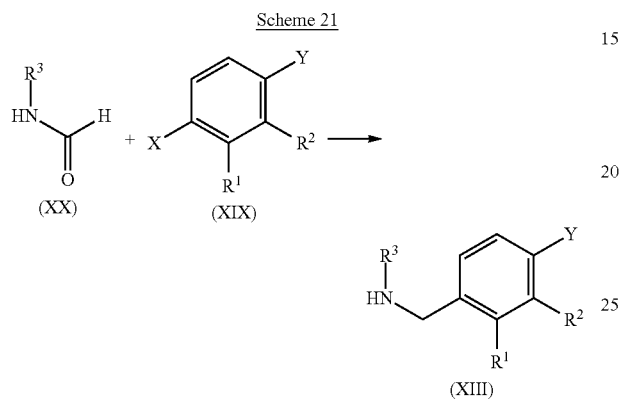

Moreover, compounds of formula (VII), wherein Y is formyl, F, Cl, Br, I, CN, or 5-(trifluoromethyl)-1,2,4-oxadiazol-3-yl, can be prepared from compounds of formula (XIX), wherein X is hydrogen, via reactions with amides or ureas of formula (XXI), wherein W is a leaving group (eg, Cl, Br, I, OH, or OSO$_2$Me) in a suitable solvent (eg, tetrahydrofuran or ethanol), in the presence of an acid (eg, hydrochloric acid, AlCl$_3$, or BF$_3$·OEt$_2$) at temperatures between 25° C. and 75° C. For related examples, see: Bohme, H. et al *Chem. Ber.* (1961), 94, 1879; Aruri, H. et al *J. Org. Chem.* (2017), 82, 1000. This reaction is shown in Scheme 22.

Alternatively, compounds of formula (VII), wherein Y is F, Cl, Br, I, CN, or 5-(trifluoromethyl)-1,2,4-oxadiazol-3-yl, can be prepared from compounds of formula (XIX), wherein X represents an organoboron, organozinc, organomagnesium, or organolithium species (eg, B(OH)$_2$, ZnCl, MgCl, or LiCl) via reactions with amides or ureas of formula (XXI), wherein W is a leaving group (eg, OSO$_2$Me, Cl, or Br), in a suitable solvent (eg, toluene), in the presence of a catalyst complex (eg, Pd(OAc)$_2$-XPhos) at temperatures between 25° C. and 75° C. For related examples, see Iwai, T. et al *Adv. Synth. & Catal.* (2014), 356, 1563. Compounds of formula (XXI) are commercially available or prepared using known methods. For related examples, see WO 2003/018552. This reaction is shown in Scheme 22.

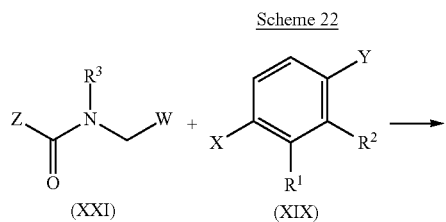

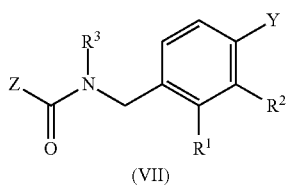

Moreover, compounds of formula (VII), wherein Y is Cl, Br, I, CN, or 5-(trifluoromethyl)-1,2,4-oxadiazol-3-yl, can be prepared from compounds of formula (XIX), wherein X is Cl, Br, or I, via reactions with amides or ureas of formula (XXI), wherein W is an organometallic group [eg, B(OH)$_2$, BF$_3$K, B(C$_{1-3}$alkoxy)$_2$, boronic pinacol ester], in a suitable solvent (eg, toluene) in the presence of a catalyst complex (eg, Pd(OAc)$_2$-XPhos) at temperatures between 25° C. and 75° C. For related examples, see Iwai, T. et al *Adv. Synth. & Catal.* (2014), 356, 1563; Kawamorita, S. et al *J. Am. Chem. Soc.* (2012), 134, 12924. Compounds of formula (XXI) are commercial available or prepared using known conditions. This reaction is shown in Scheme 23.

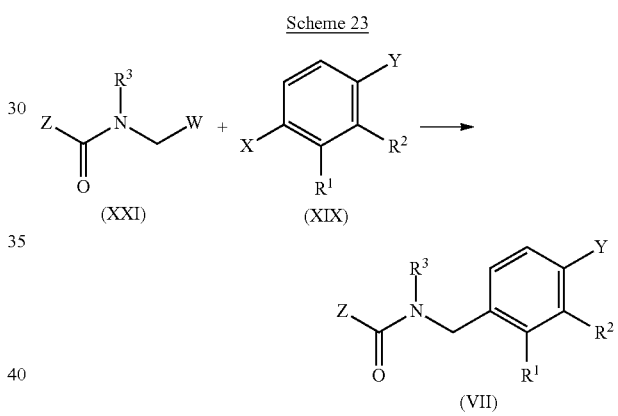

Furthermore, compounds of formula (VII), wherein Y is Cl, Br, I, CN, or 5-(trifluoromethyl)-1,2,4-oxadiazol-3-yl, can be prepared from compounds of formula (XIX), wherein X is halogen, via reactions with amides or ureas of formula (XXI), wherein W is CO$_2$H, CO$_2$CH$_3$, or CO$_2$C$_2$H$_5$, via couplings in a suitable solvent (eg, acetonitrile, DMSO, or DMF), in the presence of a base (eg, potassium tert-butoxide, sodium hydride, or lithium di-isopropylamine) at temperatures between −78° C. and 25° C. followed by heating at elevated temperatures (eg, 120° C.) in the presence of aqueous acid (eg, hydrochloric acid). For related examples, see WO 2012/039717 or Laufer, R. et al *Bioorg. & Med. Chem.* (2014), 22, 4968. Moreover, compounds of formula (VII), wherein Y is Cl, Br, I, CN, or 5-(trifluoromethyl)-1,2,4-oxadiazol-3-yl, can be prepared from compounds of formula (XIX), wherein X is halogen or CN, via photoredox catalysis using a suitable catalytic system (eg, Ru(bpy)$_3$Cl$_2$ and NiCl$_2$) in the presence of a blue light emitting diode (LED) at temperatures between 25° C. and 75° C.; optionally, an improvement in performance may be gained via flow reactor processes. For related examples, see Shaw, M. H. et al *Science* (2016), 352, 1304 and Prier, C. K. *Chem. Sci.* (2014), 5, 4173. This reaction is shown in Scheme 24.

Scheme 24

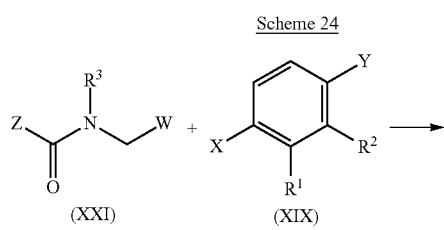

Compounds of formula (XXII) are commercially available or can be prepared from compounds of formula (XIII), wherein Y is formyl, Cl, Br, or I, via metal-promoted reactions with a cyanide reagent, such as acetone cyanohydrin, dimethylmalononitrile, $K_4[Fe(CN)_6]$, $Zn(CN)_2$, NaCN, or CuCN, in a suitable solvent (eg, dimethylformamide or N-methylpyrrolidone) at elevated temperatures between 80° C. and 120° C., and optionally in the presence of a metal catalyst (eg, Pd or Ni), an organomagnesium, or organolithium reagent. For related examples, see Reeves, J. T. et al *J. Am. Chem. Soc.* (2015), 137, 9481; Ushijima, S., Togo, H. *Synlett*, (2010), 1067; US 2007/0155739, WO 2017/055473, and WO 2009/022746. This reaction is shown in Scheme 25.

Alternatively, compounds of formula (XXII) can be prepared from compounds of formula (XIII), wherein Y is $NH_2$, via radical-nucleophilic aromatic substitution reactions using a nitrite source (eg, $NaNO_2$ or iso-amylnitrite), an acid (eg, hydrochloric acid or $HBF_4$), and a copper source (eg, CuCN) in an acceptable solvent, such as aqueous acetonitrile, at temperatures between 0° C. to 100° C. For related examples, see Wen, Q. et al *Tet. Lett.* (2014), 55, 1271. This reaction is shown in Scheme 25.

Scheme 25

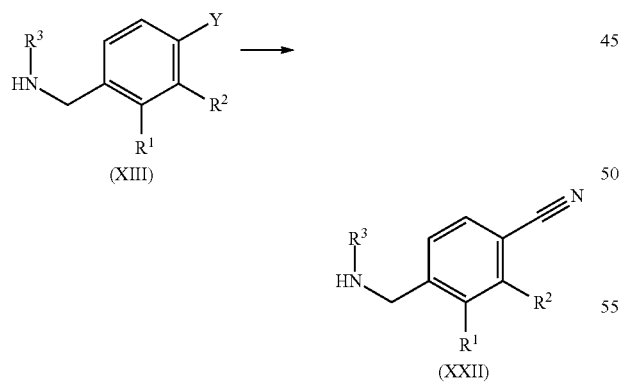

Compounds of Formula (XXIII), wherein T is $CH_3$, $CH_2OH$, $NH_2$, Cl, Br, or I, can be prepared from compounds of Formula (XXIV) via reactions with trifluoroacetic acid, trifluoroacetic ester, trifluoroacetic anhydride, or trifluoroacetyl halide (including trifluoroacetyl fluoride, trifluoroacetyl chloride and trifluoroacetyl bromide), optionally in the presence of a base (eg, pyridine or 4-dimethylaminopyridine) in a suitable solvent, (eg, toluene, ethyl acetate, tetrahydrofuran, 2-methyl tetrahydrofuran, or ethanol), at temperatures between 0° C. and 75° C. For related examples, see: WO 2003/028729, WO 2017/055473, and WO 2010/045251. This reaction is shown in Scheme 26.

Scheme 26

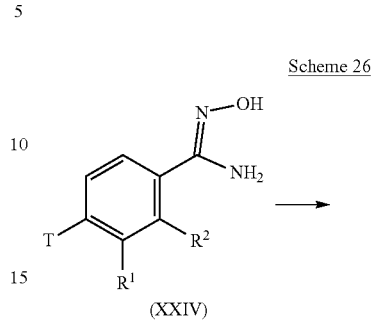

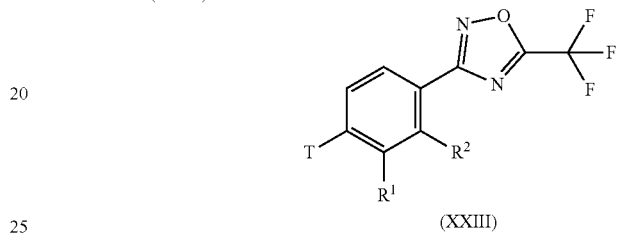

Compounds of Formula (XXIV), wherein T is $CH_3$, $CH_2OH$, $NH_2$, CN, Cl, Br, or I, can be prepared from compounds of Formula (XXV), via reactions with a hydroxylamine hydrochloride salt or a hydroxylamine solution in water, optionally in the presence of a base, such as triethylamine or potassium carbonate, in a suitable solvent, such as methanol or ethanol, at temperatures between 0° C. and 80° C. For related examples, see Kitamura, S. et al *Chem. Pharm. Bull.* (2001), 49, 268 and WO 2013/066838. In some cases, a better reaction performance may be gained from the use of a catalyst (e.g. 8-hydroxyquinoline). Compounds of Formula (XXV) are prepared by known methods or are commercially available. For related examples, see Kitamura, S. et al *Chem. Pharm. Bull.* (2001), 49, 268; WO 2017/055473, and WO 2013/066838. This reaction is shown in Scheme 27.

Scheme 27

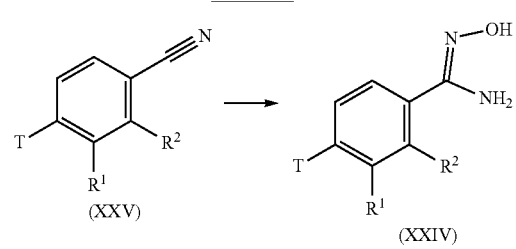

Compounds of formula (XIII), wherein Y is CN, Cl, Br, or I, can be prepared from aldehyde compounds of formula (XXVII), via condensation reactions with amines of formula (XXVI), in a suitable solvent (eg, tetrahydrofuran or methanol) at temperatures between 25° C. and 75° C., followed by the addition of a reducing reagent, such as $NaBH_3CN$, in a suitable solvent (eg, tetrahydrofuran or ethanol) at temperatures between 0° C. and 25° C. For related examples, see Gazzola, C., Kenyon, G. L. *Journal of Labeled Compounds and Radiopharmaceuticals*, (1978), 15, 181 and WO 2017/055473. This reaction is shown in Scheme 28.

Scheme 28

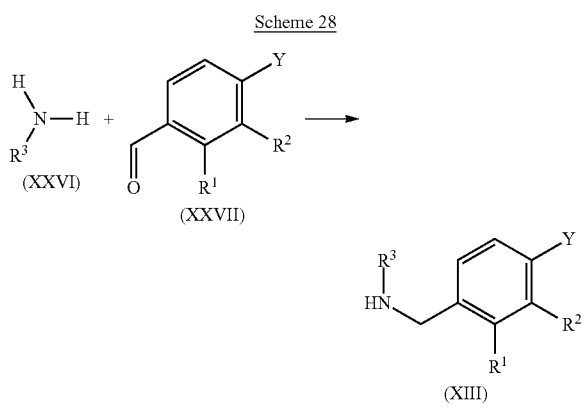

Compounds of formula (VII), wherein Y is CN, Cl, Br, I, or 5-(trifluoromethyl)-1,2,4-oxadiazol-3-yl, can be prepared from aldehyde compounds of formula (XXVII), via condensation reactions with amides or ureas of formula (XVII), in the presence of an zinc complex (eg, $Zn(OAc)_2 \cdot H_2O$), in a suitable solvent (eg, NMP, DMF, and $H_2O$) at elevated temperatures (eg, 150° C.). For related examples, see Yang, Luo et al *Adv. Synth. & Catal.* (2018), 360, 485; Barba, F. et al *Tetrahedron. Lett.* (2013), 54, 1835; Wang, J. et al *Chem. Commun.* (2014), 50, 4736. This reaction is shown in Scheme 29.

Scheme 29

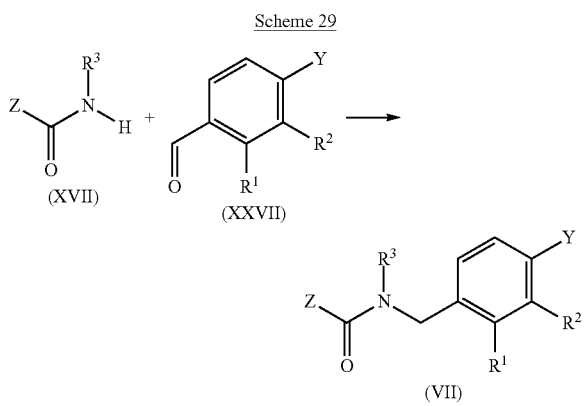

Compositions of this invention, including all of the above disclosed embodiments and preferred examples thereof, can be mixed with one or more further pesticides including further fungicides, insecticides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection.

Examples of such agricultural protectants with which the composition of this invention can be formulated are:

Fungicides such as etridiazole, fluazinam, benalaxyl, benalaxyl-M (kiralaxyl), furalaxyl, metalaxyl, metalaxyl-M (mefenoxam), dodicin, N'-(2,5-dimethyl-4-phenoxy-phenyl)-N-ethyl-N-methyl-formamidine, N'-[4-(4,5-dichloro-thiazol-2-yloxy)-2,5-dimethyl-phenyl]-N-ethyl-N-methyl-formamidine, N'-[4-[[3-[(4-chlorophenyl)methyl]-1,2,4-thiadiazol-5-yl]oxy]-2,5-dimethyl-phenyl]-N-ethyl-N-methyl-formamidine, ethirimol, 3'-chloro-2-methoxy-N-[(3RS)-tetrahydro-2-oxofuran-3-yl]acet-2',6'-xylidide (clozylacon), cyprodinil, mepanipyrim, pyrimethanil, dithianon, aureofungin, blasticidin-S, biphenyl, chloroneb, dicloran, benzovindiflupyr, pydiflumetofen, hexachlorobenzene, quintozene, tecnazene, (TCNB), tolclofos-methyl, metrafenone, 2,6-dichloro-N-(4-trifluoromethylbenzyl)-benzamide, fluopicolide (flupicolide), tioxymid, flusulfamide, benomyl, carbendazim, carbendazim chlorhydrate, chlorfenazole, fuberidazole, thiabendazole, thiophanate-methyl, benthiavalicarb, chlobenthiazone, probenazole, acibenzolar, bethoxazin, pyriofenone (IKF-309), acibenzolar-S-methyl, pyribencarb (KIF-7767), butylamine, 3-iodo-2-propinyl n-butylcarbamate (IPBC), iodocarb (isopropanyl butylcarbamate), isopropanyl butylcarbamate (iodocarb), picarbutrazox, polycarbamate, propamocarb, tolprocarb, 3-(difluoromethyl)-N-(7-fluoro-1,1,3,3-tetramethyl-indan-4-yl)-1-methyl-pyrazole-4-carboxamide diclocymet, N-[(5-chloro-2-isopropyl-phenyl)methyl]-N-cyclopropyl-3-(difluoromethyl)-5-fluoro-1-methyl-pyrazole-4-carboxamide N-cyclopropyl-3-(difluoromethyl)-5-fluoro-N-[(2-isopropylphenyl)methyl]-1-methyl-pyrazole-4-carboxamide carpropamid, chlorothalonil, flumorph, oxinecopper, cymoxanil, phenamacril, cyazofamid, flutianil, thicyofen, chlozolinate, iprodione, procymidone, vinclozolin, bupirimate, dinocton, dinopenton, dinobuton, dinocap, meptyldinocap, diphenylamine, phosdiphen, 2,6-dimethyl-[1,4]dithiino[2,3-c:5,6-c']dipyrrole-1,3,5,7(2H,6H)-tetraone, azithiram, etem, ferbam, mancozeb, maneb, metam, metiram (polyram), metiram-zinc, nabam, propineb, thiram, vapam (metam sodium), zineb, ziram, dithioether, isoprothiolane, ethaboxam, fosetyl, phosetyl-Al (fosetyl-al), methyl bromide, methyl iodide, methyl isothiocyanate, cyclafuramid, fenfuram, validamycin, streptomycin, (2RS)-2-bromo-2-(bromomethyl)glutaronitrile (bromothalonil), dodine, doguadine, guazatine, iminoctadine, iminoctadine triacetate, 2,4-D, 2,4-DB, kasugamycin, dimethirimol, fenhexamid, hymexazole, hydroxyisoxazole imazalil, imazalil sulphate, oxpoconazole, pefurazoate, prochloraz, triflumizole, fenamidone, Bordeaux mixture, calcium polysulfide, copper acetate, copper carbonate, copper hydroxide, copper naphthenate, copper oleate, copper oxychloride, copper oxyquinolate, copper silicate, copper sulphate, copper tallate, cuprous oxide, sulphur, carbaryl, phthalide (fthalide), dingjunezuo (Jun Si Qi), oxathiapiprolin, fluoroimide, mandipropamid, KSF-1002, benzamorf, dimethomorph, fenpropimorph, tridemorph, dodemorph, diethofencarb, fentin acetate, fentin hydroxide, carboxin, oxycarboxin, drazoxolon, famoxadone, m-phenylphenol, p-phenylphenol, tribromophenol (TBP), 2-[2-[(7,8-difluoro-2-methyl-3-quinolyl)oxy]-6-fluoro-phenyl]propan-2-ol 2-[2-fluoro-6-[(8-fluoro-2-methyl-3-quinolyl)oxy]phenyl]propan-2-ol cyflufenamid, ofurace, oxadixyl, flutolanil, mepronil, isofetamid, fenpiclonil, fludioxonil, pencycuron, edifenphos, iprobenfos, pyrazophos, phosphorus acids, tecloftalam, captafol, captan, ditalimfos, triforine, fenpropidin, piperalin, osthol, 1-methylcyclopropene, 4-CPA, chlormequat, clofencet, dichlorprop, dimethipin, endothal, ethephon, flumetralin, forchlorfenuron, gibberellic acid, gibberellins, hymexazol, maleic hydrazide, mepiquat, naphthalene acetamide, paclobutrazol, prohexadione, prohexadione-calcium, thidiazuron, tribufos (tributyl phosphorotrithioate), trinexapac, uniconazole, α-naphthalene acetic acid, polyoxin D (polyoxrim), BLAD, chitosan, fenoxanil, folpet, 3-(difluoromethyl)-N-methoxy-1-methyl-N-[1-methyl-2-(2,4,6-trichlorophenyl)ethyl]pyrazole-4-carboxamide, bixafen, fluxapyroxad, furametpyr, isopyrazam, penflufen, penthiopyrad, sedaxane, fenpyrazamine, diclomezine, pyrifenox, boscalid, fluopyram, diflumetorim, fenarimol, 5-fluoro-2-(p-tolylmethoxy)pyrimidin-4-amine ferimzone, dimetachlone (dimethaclone), pyroquilon, proquinazid, ethoxyquin, quinoxyfen, 4,4,5-trifluoro-3,3-dimethyl-1-(3-quinolyl)isoquinoline, 4,4-difluoro-3,3-dimethyl-1-(3-quinolyl)isoquinoline 5-fluoro-3,3,4,4-tetramethyl-1-(3-quinolyl)isoquinoline 9-fluoro-2,2-dimethyl-5-(3-quinolyl)-3H-1,4-benzoxazepine, tebufloquin, oxolinic acid, chinomethionate (oxythioquinox, quinoxymethionate), spiroxamine, (E)-N-methyl-2-[2-(2,5-dimethylphenoxymethyl) phenyl]-2-methoxy-iminoacetamide, (mandestrobin), azoxystrobin, coumoxystrobin, dimoxystrobin, enestroburin, enoxastrobin, fenamistrobin, flufenoxystrobin, fluoxastrobin, kresoxim-methyl, mandestrobin, metaminostrobin, metominostrobin, orysastrobin, picoxystrobin, pyraclostrobin, pyrametostrobin, pyraoxystrobin, triclopyricarb, trifloxystrobin, amisulbrom, dichlofluanid, tolylfluanid, but-3-ynyl N-[6-[[(Z)-[(1-methyltetrazol-5-yl)-phenyl-methylene]amino] oxymethyl]-2-pyridyl]carbamate, dazomet, isotianil, tiadinil, thifluzamide, benthiazole (TCMTB), silthiofam, zoxamide, anilazine, tricyclazole, (.+–.)-cis-1-(4-chlorophenyl)-2-(1H-1,2,4-triazol-1-yl)-cycloheptanol (huanjunzuo), 1-(5-bromo-2-pyridyl)-2-(2,4-difluorophenyl)-1,1-difluoro-3-(1,2,4-triazol-1-yl)propan-2-ol 2-(1-tert-butyl)-1-(2-chlorophenyl)-3-(1,2,4-triazol-1-yl)-propan-2-ol (TCDP), azaconazole, bitertanol (biloxazol), bromuconazole, climbazole, cyproconazole, difenoconazole, dimetconazole, diniconazole, diniconazole-M, epoxiconazole, etaconazole, fenbuconazole, fluquinconazole, flusilazole, flutriafol, hexaconazole, imibenconazole, ipconazole, ipfentrifluconazole, metconazole, myclobutanil, penconazole, propiconazole, prothioconazole, simeconazole, tebuconazole, tetraconazole, triadimefon, triadimenol, triazoxide, triticonazole, mefentrifluconazole, 2-[[(1R,5S)-5-[(4-fluorophenyl) methyl]-1-hydroxy-2,2-dimethyl-cyclopentyl]methyl]-4H-1,2,4-triazole-3-thione, 2-[[3-(2-chlorophenyl)-2-(2,4-difluorophenyl)oxiran-2-yl]methyl]-4H-1,2,4-triazole-3-thione, ametoctradin (imidium), iprovalicarb, valifenalate, 2-benzyl-4-chlorophenol (Chlorphene), allyl alcohol, azafenidin, benzalkonium chloride, chloropicrin, cresol, daracide, dichlorophen (dichlorophene), difenzoquat, dipyrithione, N-(2-p-chlorobenzoylethyl)-hexaminium chloride, NNF-0721, octhilinone, oxasulfuron, propamidine and propionic acid.

Insecticides such as abamectin, acephate, acetamiprid, amidoflumet (S-1955), avermectin, azadirachtin, azinphos-methyl, bifenthrin, bifenazate, buprofezin, carbofu ran, cartap, chlorantraniliprole (DPX-E2Y45), chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, taufluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron;

Bactericides such as streptomycin;

Acaricides such as amitraz, chinomethionat, chlorobenzilate, cyenopyrafen, cyhexatin, dicofol, dienochlor, etoxazole, fenazaquin, fenbutatin oxide, fenpropathrin, fenpyroximate, hexythiazox, propargite, pyridaben and tebufenpyrad; and Biological agents such as *Bacillus thuringiensis, Bacillus thuringiensis* delta endotoxin, baculovirus, and entomopathogenic bacteria, virus and fungi.

Other examples of "reference" mixture compositions are as follows (wherein the term "TX" represents a compound (according to the definition of component (A) of the compositions of the present invention) selected from compound no. X.01, X.02, X.03, X.04, X.05, X.06, X.07, X.08, X.09, X.10, X.11, X.12, X.13, X.14, X.15, X.16, X.17, X.18, X.19, X.20, X.21, X.22, X.23, X.24 or X.25, as defined in the Table X above or Table T1 below):

an adjuvant selected from the group of substances consisting of petroleum oils (alternative name) (628)+TX,
an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50,439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+

TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, *Bacillus subtilis* var. *amyloliquefaciens* Strain FZB24 (available from Novozymes Biologicals Inc., 5400 Corporate Circle, Salem, Va. 24153, U.S.A. and known under the trade name Taegro®)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure Bi (alternative name) (839)+TX, trimedlure B2 (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis (4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name)

(210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, Myrothecium verrucaria composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesamolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of ametoctradin [865318-97-4]+TX, amisulbrom [348635-87-0]+TX, azaconazole [60207-31-0]+TX, benzovindiflupyr [1072957-71-1]+TX, bitertanol [70585-36-3]+TX, bixafen [581809-46-3]+TX, bromuconazole [116255-48-2]+TX, coumoxystrobin [850881-70-8]+TX, cyproconazole [94361-06-5]+TX, difenoconazole [119446-68-3]+TX, diniconazole [83657-24-3]+TX, enoxastrobin [238410-11-2]+TX, epoxiconazole [106325-08-0]+TX, fenbuconazole [114369-43-6]+TX, fenpyrazamine [473798-59-3]+TX, fluquinconazole [136426-54-5]+TX, flusilazole [85509-19-9]+TX, flutriafol [76674-21-0]+TX, fluxapyroxad [907204-31-3]+TX, fluopyram [658066-35-4]+TX, fenaminstrobin [366815-39-6]+TX, isofetamid [875915-78-9]+TX, hexaconazole [79983-71-4]+TX, imazalil [35554-44-0]+TX, imibenconazole [86598-92-7]+TX, ipconazole [125225-28-7]+TX, ipfentrifluconazole [1417782-08-1]+TX, inpyrfluxam [1352994-67-2]+TX, isotianil [224049-04-1]+TX, mandestrobin [173662-97-0] (can be prepared according to the procedures described in WO 2010/093059)+TX, mefentrifluconazole [1417782-03-6]+TX, metconazole [125116-23-6]+TX, myclobutanil [88671-89-0]+TX, paclobutrazol [76738-62-0]+TX, pefurazoate [101903-30-4]+TX, penflufen [494793-67-8]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidin [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, fluindapyr [1383809-87-7]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, flutianil [958647-10-4]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, pyraoxystrobin [862588-11-2]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, picarbutrazox [500207-04-5]+TX, polyoxins [11113-80-7]+TX, probenazole [27605-76-1]+TX, propamocarb [25606-41-1]+TX, proquinazid [189278-12-4]+TX, pydiflumetofen [1228284-64-7]+TX, pyrametostrobin [915410-70-7]+TX, pyroquilon [57369-32-1]+TX, pyriofenone [688046-61-9]+TX, pyribencarb [799247-52-2]+TX, pyrisoxazole [847749-37-5]+TX, quinoxyfen [124495-18-7]+TX, quintozene [82-68-8]+TX, sulfur [7704-34-9]+TX, Timorex Gold™ (plant extract containing tea tree oil from the Stockton Group)+TX, tebufloquin [376645-78-2]+TX, tiadinil [223580-51-6]+TX, triazoxide [72459-58-6]+TX, tolprocarb [911499-62-2]+TX, triclopyricarb [902760-40-1]+TX, tricyclazole [41814-78-2]+TX, triforine [26644-46-2]+TX, validamycin [37248-47-8]+TX, valifenalate [283159-90-0]+TX, zoxamide (RH7281) [156052-68-5]+TX, mandipropamid [374726-62-2]+TX, isopyrazam [881685-58-1]+TX, phenamacril+TX, sedaxane [874967-67-6]+TX, trinexapac-ethyl [95266-40-3]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX, or a biologically active compound selected from the group consisting of N-[(5-chloro-2-isopropyl-phenyl)methyl]-N-cyclopropyl-3-(difluoromethyl)-5-fluoro-1-methyl-pyrazole-4-carboxamide (can be prepared according to the procedures described in WO 2010/130767)+TX, 2,6-Dimethyl-1H,5H-[1,4]dithiino[2,3-c:5,6-c']dipyrrole-1,3,5,7(2H,6H)-tetrone (can be prepared according to the procedures described in WO 2011/138281)+TX, 6-ethyl-5,7-dioxo-pyrrolo[4,5][1,4]dithiino[1,2-c]isothiazole-3-carbonitrile+TX, 4-(2-bromo-4-fluoro-phenyl)-N-(2-chloro-6-fluoro-phenyl)-2,5-dimethyl-pyrazol-3-amine (can be prepared according to the procedures described in WO 2012/031061)+TX, 3-(difluoromethyl)-N-(7-fluoro-1,1,3-trimethyl-indan-4-yl)-1-methyl-pyrazole-4-carboxamide (can be prepared according to the procedures described in WO 2012/084812)+TX, CAS 850881-30-0+TX, 3-(3,4-dichloro-1,2-thiazol-5-ylmethoxy)-1,2-benzothiazole 1,1-dioxide (can be prepared according to the procedures described in WO 2007/129454)+TX, 2-[2-[(2,5-dimethylphenoxy)methyl]phenyl]-2-methoxy-N-methyl-acetamide+TX, 3-(4,4-difluoro-3,4-dihydro-3,3-dimethylisoquinolin-1-yl)quinolone (can be prepared according to the procedures described in WO 2005/070917)+TX, 2-[2-fluoro-6-[(8-fluoro-2-methyl-3-quinolyl)oxy]phenyl]propan-2-ol (can be prepared according to the procedures described in WO 2011/081174)+TX, 2-[2-[(7,8-difluoro-2-methyl-3-quinolyl)oxy]-6-fluoro-phenyl]propan-2-ol (can be prepared according to the procedures described in WO 2011/081174)+TX, oxathiapiprolin+TX [1003318-67-9], tert-butyl N-[6-[[[(1-methyltetrazol-5-yl)-phenyl-methylene]amino]oxymethyl]-2-pyridyl]carbamate+TX, N-[2-(3,4-difluorophenyl)phenyl]-3-(trifluoromethyl)pyrazine-2-carboxamide (can be prepared according to the procedures described in WO 2007/072999)+TX, 3-(difluoromethyl)-1-methyl-N-[(3R)-1,1,3-trimethylindan-4-yl]pyrazole-4-carboxamide (can be prepared according to the procedures described in WO 2014/013842)+TX, 2,2,2-trifluoroethyl N-[2-methyl-1-[[(4-methylbenzoyl)amino]methyl]propyl]carbamate+TX, (2RS)-2-[4-(4-chlorophenoxy)-α,α,α-trifluoro-o-tolyl]-1-(1H-1,2,4-triazol-1-yl)propan-2-ol+TX, (2RS)-2-[4-(4-chlorophenoxy)-α,α,α-trifluoro-o-tolyl]-3-methyl-1-(1H-1,2,4-triazol-1-yl)butan-2-ol+TX, 2-(difluoromethyl)-N-[(3R)-3- ethyl-1,1-dimethyl-indan-4-yl]pyridine-3-carboxamide+TX, 2-(difluoromethyl)-N-[3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine (can be prepared according to the procedures described in WO 2007/031513)+TX, [2-[3-[2-[1-[2-[3,5-bis(difluoromethyl)pyrazol-1-yl]acetyl]-4-piperidyl]thiazol-4-yl]-4,5-dihydroisoxazol-5-yl]-3-chloro-phenyl] methanesulfonate (can be prepared according to the procedures described in WO 2012/025557)+TX, but-3-ynyl N-[6-[[(Z)-[(1-methyltetrazol-5-yl)-phenyl-methylene]amino]oxymethyl]-2-pyridyl]carbamate (can be prepared according to the procedures described in WO 2010/000841)+TX, 2-[[3-(2-chlorophenyl)-2-(2,4-difluorophenyl)oxiran-2-yl]methyl]-4H-1,2,4-triazole-3-thione (can be prepared according to the procedures described in WO 2010/146031)+TX, methyl N-[[5-[4-(2,4-dimethylphenyl)triazol-2-yl]-2-methyl-phenyl]methyl]carbamate+TX, 3-chloro-6-methyl-5-phenyl-4-(2,4,6-trifluorophenyl)pyridazine (can be prepared according to the procedures described in WO 2005/121104)+TX, 2-[2-chloro-4-(4-chlorophenoxy)phenyl]-1-(1,2,4-triazol-1-yl)propan-2-ol (can be prepared according to the procedures described in WO 2013/024082)+TX, 3-chloro-4-(2,6-difluorophenyl)-6-methyl-5-phenyl-pyridazine (can be prepared according to the procedures described in WO 2012/020774)+TX, 4-(2,6-difluorophenyl)-6-methyl-5-phenyl-pyridazine-3-carbonitrile (can be prepared according to the procedures described in WO 2012/020774)+TX, (R)-3-(difluoromethyl)-1-methyl-N-[1,1,3-trimethylindan-4-yl]pyrazole-4-carboxamide (can be prepared according to the procedures described in WO 2011/162397)+TX, 3-(difluoromethyl)-N-(7-fluoro-1,1,3-trimethyl-indan-4-yl)-1-methyl-pyrazole-4-carboxamide (can be prepared according to the procedures described in WO 2012/084812)+TX, 1-[2-[[1-(4-chlorophenyl)pyrazol-3-yl]oxymethyl]-3-methyl-phenyl]-4-methyl-tetrazol-5-one (can be prepared according to the procedures described in WO 2013/162072)+TX, 1-methyl-4-[3-methyl-2-[[2-methyl-4-(3,4,5-trimethylpyrazol-1-yl)phenoxy]methyl]phenyl]tetrazol-5-one (can be prepared according to the procedures described in WO 2014/051165)+TX, (Z,2E)-5-[1-(4-chlorophenyl)pyrazol-3-yl]oxy-2-methoxyimino-N,3-dimethyl-pent-3-enamide+TX, (4-phenoxyphenyl)methyl 2-amino-6-methyl-pyridine-3-carboxylate+TX, N-(5-chloro-2-isopropylbenzyl)-N-cyclopropyl-3-(difluoromethyl)-5-fluoro-1-methylpyrazole-4-carboxamide [1255734-28-1] (can be prepared according to the procedures described in WO 2010/130767)+TX, 3-(difluoromethyl)-N-[(R)-2,3-dihydro-1,1,3-trimethyl-1H-inden-4-yl]-1-methylpyrazole-4-carboxamide [1352994-67-2]+TX, N'-(2,5-dimethyl-4-phenoxy-phenyl)-N-ethyl-N-methyl-formamidine+TX, N'-[4-(4,5-dichloro-thiazol-2-yloxy)-2,5-dimethyl-phenyl]-N-ethyl-N-methyl-formamidine+TX, N'-(2,5-dimethyl-4-phenoxy-phenyl)-N-ethyl-N-methyl-formamidine+TX, N'-[4-(4,5-dichloro-thiazol-2-yloxy)-2,5-dimethyl-phenyl]-N-ethyl-N-methyl-formamidine+TX,

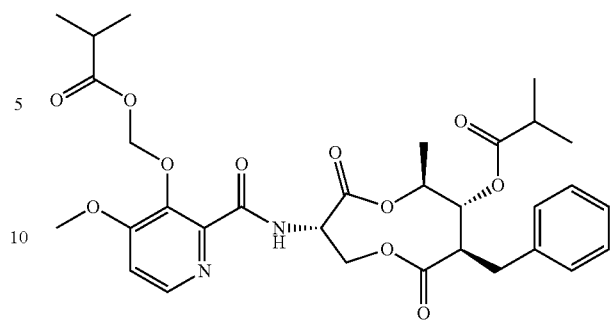

(fenpicoxamid [517875-34-2]) (as described in WO 2003/035617)+TX, (1S)-2,2-bis(4-fluorophenyl)-1-methylethyl-N-{[3-(acetyloxy)-4-methoxy-2-pyridyl]carbonyl}-L-alaninate [1961312-55-9] (as described in WO 2016/122802)+TX, N'-[5-bromo-2-methyl-6-(1-methyl-2-propoxy-ethoxy)-3-pyridyl]-N-ethyl-N-methyl-formamidine [1817828-69-5]+TX, N'-[5-bromo-2-methyl-6-[(1S)-1-methyl-2-propoxy-ethoxy]-3-pyridyl]-N-ethyl-N-methyl-formamidine+TX, N'-[5-bromo-2-methyl-6-[(1R)-1-methyl-2-propoxy-ethoxy]-3-pyridyl]-N-ethyl-N-methyl-formamidine+TX, N'-[5-bromo-2-methyl-6-(1-methyl-2-propoxy-ethoxy)-3-pyridyl]-N-isopropyl-N-methyl-formamidine+TX, N'-[5-chloro-2-methyl-6-(1-methyl-2-propoxy-ethoxy)-3-pyridyl]-N-ethyl-N-methyl-formamidine+TX; or 2-(difluoromethyl)-N-(1,1,3-trimethylindan-4-yl)pyridine-3-carboxamide+TX, 2-(difluoromethyl)-N-(3-ethyl-1,1-dimethyl-indan-4-yl)pyridine-3-carboxamide+TX, 2-(difluoromethyl)-N-(1,1-dimethyl-3-propyl-indan-4-yl)pyridine-3-carboxamide+TX, 2-(difluoromethyl)-N-(3-isobutyl-1,1-dimethyl-indan-4-yl)pyridine-3-carboxamide+TX, 2-(difluoromethyl)-N-[(3R)-1,1,3-trimethylindan-4-yl]pyridine-3-carboxamide+TX, 2-(difluoromethyl)-N-[(3R)-3-ethyl-1,1-dimethyl-indan-4-yl]pyridine-3-carboxamide+TX, and 2-(difluoromethyl)-N-[(3R)-1,1-dimethyl-3-propyl-indan-4-yl]pyridine-3-carboxamide+TX, wherein each of these carboxamide compounds can be prepared according to the procedures described in WO 2014/095675 and/or WO 2016/139189.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright 1995-2004]; for example, the compound "acetoprole" is described under the internet address http://www.alanwood.net/pesticides/acetoprole.html Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

In the "reference" mixture compositions the mixtures of compounds of formula (I) (selected from Table X (above)) with active ingredients described above comprise a compound selected from Table X (above) and an active ingredient as described above preferably in a mixing ratio of from 100:1 to 1:100, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixture compositions as described above (both according to the invention and the "reference" mixture compositions) can be used in a method for controlling pests, which comprises applying a composition comprising a mixture as described above to the pests or their environment.

The mixtures comprising a compound of formula (I) selected from Table X (above) and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula (I) selected from Table X (above) and the active ingredients as described above is not essential for working the present invention.

The compositions of the present invention may also be used in crop enhancement. According to the present invention, 'crop enhancement' means an improvement in plant vigour, an improvement in plant quality, improved tolerance to stress factors, and/or improved input use efficiency.

According to the present invention, an 'improvement in plant vigour' means that certain traits are improved qualitatively or quantitatively when compared with the same trait in a control plant which has been grown under the same conditions in the absence of the method of the invention. Such traits include, but are not limited to, early and/or improved germination, improved emergence, the ability to use less seeds, increased root growth, a more developed root system, increased root nodulation, increased shoot growth, increased tillering, stronger tillers, more productive tillers, increased or improved plant stand, less plant verse (lodging), an increase and/or improvement in plant height, an increase in plant weight (fresh or dry), bigger leaf blades, greener leaf colour, increased pigment content, increased photosynthetic activity, earlier flowering, longer panicles, early grain maturity, increased seed, fruit or pod size, increased pod or ear number, increased seed number per pod or ear, increased seed mass, enhanced seed filling, less dead basal leaves, delay of senescence, improved vitality of the plant, increased levels of amino acids in storage tissues and/or less inputs needed (e.g. less fertiliser, water and/or labour needed). A plant with improved vigour may have an increase in any of the aforementioned traits or any combination or two or more of the aforementioned traits.

According to the present invention, an 'improvement in plant quality' means that certain traits are improved qualitatively or quantitatively when compared with the same trait in a control plant which has been grown under the same conditions in the absence of the method of the invention. Such traits include, but are not limited to, improved visual appearance of the plant, reduced ethylene (reduced production and/or inhibition of reception), improved quality of harvested material, e.g. seeds, fruits, leaves, vegetables (such improved quality may manifest as improved visual appearance of the harvested material), improved carbohydrate content (e.g. increased quantities of sugar and/or starch, improved sugar acid ratio, reduction of reducing sugars, increased rate of development of sugar), improved protein content, improved oil content and composition, improved nutritional value, reduction in anti-nutritional compounds, improved organoleptic properties (e.g. improved taste) and/or improved consumer health benefits (e.g. increased levels of vitamins and anti-oxidants)), improved post-harvest characteristics (e.g. enhanced shelf-life and/or storage stability, easier processability, easier extraction of compounds), more homogenous crop development (e.g. synchronised germination, flowering and/or fruiting of plants), and/or improved seed quality (e.g. for use in following seasons). A plant with improved quality may have an increase in any of the aforementioned traits or any combination or two or more of the aforementioned traits.

According to the present invention, an 'improved tolerance to stress factors' means that certain traits are improved qualitatively or quantitatively when compared with the same trait in a control plant which has been grown under the same conditions in the absence of the method of the invention. Such traits include, but are not limited to, an increased tolerance and/or resistance to abiotic stress factors which cause sub-optimal growing conditions such as drought (e.g. any stress which leads to a lack of water content in plants, a lack of water uptake potential or a reduction in the water supply to plants), cold exposure, heat exposure, osmotic stress, UV stress, flooding, increased salinity (e.g. in the soil), increased mineral exposure, ozone exposure, high light exposure and/or limited availability of nutrients (e.g. nitrogen and/or phosphorus nutrients). A plant with improved tolerance to stress factors may have an increase in any of the aforementioned traits or any combination or two or more of the aforementioned traits. In the case of drought and nutrient stress, such improved tolerances may be due to, for example, more efficient uptake, use or retention of water and nutrients.

According to the present invention, an 'improved input use efficiency' means that the plants are able to grow more effectively using given levels of inputs compared to the grown of control plants which are grown under the same conditions in the absence of the method of the invention. In particular, the inputs include, but are not limited to fertiliser (such as nitrogen, phosphorous, potassium, micronutrients), light and water. A plant with improved input use efficiency may have an improved use of any of the aforementioned inputs or any combination of two or more of the aforementioned inputs.

Other crop enhancements of the present invention include a decrease in plant height, or reduction in tillering, which are beneficial features in crops or conditions where it is desirable to have less biomass and fewer tillers.

Any or all of the above crop enhancements may lead to an improved yield by improving e.g. plant physiology, plant growth and development and/or plant architecture. In the context of the present invention 'yield' includes, but is not limited to, (i) an increase in biomass production, grain yield, starch content, oil content and/or protein content, which may result from (a) an increase in the amount produced by the plant per se or (b) an improved ability to harvest plant matter, (ii) an improvement in the composition of the harvested material (e.g. improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life. Increased yield of an agricultural plant means that, where it is possible to take a quantitative measurement, the yield of a product of the respective plant is increased by a measurable amount over the yield of the same product of the plant produced under the same conditions, but without application of the present invention. According to the present invention, it is preferred that the yield be increased by at least 0.5%, more preferred at least 1%, even more preferred at least 2%, still more preferred at least 4%, preferably 5% or even more.

Any or all of the above crop enhancements may also lead to an improved utilisation of land, i.e. land which was previously unavailable or sub-optimal for cultivation may become available. For example, plants which show an increased ability to survive in drought conditions, may be able to be cultivated in areas of sub-optimal rainfall, e.g. perhaps on the fringe of a desert or even the desert itself.

In one aspect of the present invention, crop enhancements are made in the substantial absence of pressure from pests and/or diseases and/or abiotic stress. In a further aspect of the present invention, improvements in plant vigour, stress tolerance, quality and/or yield are made in the substantial absence of pressure from pests and/or diseases. For example pests and/or diseases may be controlled by a pesticidal treatment that is applied prior to, or at the same time as, the method of the present invention. In a still further aspect of the present invention, improvements in plant vigour, stress tolerance, quality and/or yield are made in the absence of pest and/or disease pressure. In a further embodiment, improvements in plant vigour, quality and/or yield are made in the absence, or substantial absence, of abiotic stress.

The compositions of the present invention may also be used in the field of protecting storage goods against attack of fungi. According to the present invention, the term "storage goods" is understood to denote natural substances of vegetable and/or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The composition according the present invention can prevent disadvantageous effects such as decay, discoloration or mold. Preferably "storage goods" is understood to denote natural substances of vegetable origin and/or their processed forms, more preferably fruits and their processed forms, such as pomes, stone fruits, soft fruits and citrus fruits and their processed forms. In another preferred embodiment of the invention "storage goods" is understood to denote wood.

Therefore a further aspect of the present invention is a method of protecting storage goods, which comprises applying to the storage goods a composition according to the invention.

The composition of the present invention may also be used in the field of protecting technical material against attack of fungi. According to the present invention, the term "technical material" includes paper; carpets; constructions; cooling and heating systems; wall-boards; ventilation and air conditioning systems and the like; preferably "technical material" is understood to denote wall-boards. The composition according the present invention can prevent disadvantageous effects such as decay, discoloration or mold.

The composition according to the invention is generally formulated in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, micro-emulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art.

Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the formulations according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood, N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The formulations according to the invention can include an additive comprising an oil of vegetable or animal origin, a mineral oil, alkyl esters of such oils or mixtures of such oils and oil derivatives. The amount of oil additive in the formulation according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The formulations generally comprise from 0.1 to 99% by weight, especially from 0.1 to 95% by weight, of compounds of component (A) and component (B) and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Certain mixture compositions comprising a compound of formula (I) described above may show a synergistic effect. This occurs whenever the action of an active ingredient combination is greater than the sum of the actions of the individual components. The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient A) using p ppm of active ingredient

Y=% action by active ingredient B) using q ppm of active ingredient.

According to COLBY, the expected (additive) action of active ingredients A)+B) using p+q ppm of active ingredient is:

$$E = X + Y - \frac{X \cdot Y}{100}.$$

If the action actually observed (O) is greater than the expected action (E), then the action of the combination is super-additive, i.e. there is a synergistic effect. In mathematical terms, synergism corresponds to a positive value for the difference of (O-E). In the case of purely complementary addition of activities (expected activity), said difference (O-E) is zero. A negative value of said difference (O-E) signals a loss of activity compared to the expected activity.

However, besides the actual synergistic action with respect to fungicidal activity, the composition according to the invention may also have further surprising advantageous properties. Examples of such advantageous properties that may be mentioned are: more advantageous degradability; improved toxicological and/or ecotoxicological behaviour; or improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination.

The composition according to the invention can be applied to the phytopathogenic microorganisms, the useful plants, the locus thereof, the propagation material thereof, storage goods or technical materials threatened by microorganism attack.

The composition according to the invention may be applied before or after infection of the useful plants, the propagation material thereof, storage goods or technical materials by the microorganisms.

The amount of a composition according to the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of fungi to be controlled or the application time.

When applied to the useful plants component (A) is typically applied at a rate of 5 to 2000 g a.i./ha, particularly 10 to 1000 g a.i./ha, e.g. 50, 75, 100 or 200 g a.i./ha, typically in association with 1 to 5000 g a.i./ha, particularly 2 to 2000 g a.i./ha, e.g. 100, 250, 500, 800, 1000, 1500 g a.i./ha of component (B).

In agricultural practice the application rates of the composition according to the invention depend on the type of effect desired, and typically range from 20 to 4000 g of total composition per hectare.

When the composition according to the invention is used for treating seed, rates of 0.001 to 50 g of a compound of component (A) per kg of seed, preferably from 0.01 to 10 g per kg of seed, and 0.001 to 50 g of a compound of component (B), per kg of seed, preferably from 0.01 to 10 g per kg of seed, are generally sufficient.

For the avoidance of doubt, where a literary reference, patent application, or patent, is cited within the text of this application, the entire text of said citation is herein incorporated by reference.

EXAMPLES

The Examples which follow serve to illustrate the invention. The compounds (and compositions) of the invention may be distinguished from known compounds (and compositions) by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm or 0.2 ppm of active ingredient(s).

Throughout this description, temperatures are given in degrees Celsius (° C.) and "mp." means melting point. LC/MS means Liquid Chromatography Mass Spectrometry and the description of the apparatus and the method (Methods A and B) is as follows:

The Description of the LC/MS Apparatus and the Method A is:
SQ Detector 2 from Waters
Ionisation method: Electrospray
Polarity: positive and negative ions
Capillary (kV) 3.0, Cone (V) 30.00, Extractor (V) 2.00, Source Temperature (° C.) 150, Desolvation Temperature (° C.) 350, Cone Gas Flow (L/Hr) 0, Desolvation Gas Flow (L/Hr) 650
Mass range: 100 to 900 Da
DAD Wavelength range (nm): 210 to 500
Method Waters ACQUITY UPLC with the Following HPLC Gradient Conditions:
(Solvent A: Water/Methanol 20:1+0.05% Formic Acid and Solvent B: Acetonitrile+0.05% Formic Acid)

| Time (minutes) | A (%) | B (%) | Flow rate (ml/min) |
|---|---|---|---|
| 0 | 100 | 0 | 0.85 |
| 1.2 | 0 | 100 | 0.85 |
| 1.5 | 0 | 100 | 0.85 |

Type of column: Waters ACQUITY UPLC HSS T3; Column length: 30 mm; Internal diameter of column: 2.1 mm; Particle Size: 1.8 micron; Temperature: 60° C.

The Description of the LC/MS Apparatus and the Method B is:
SQ Detector 2 from Waters
Ionisation method: Electrospray
Polarity: positive ions
Capillary (kV) 3.5, Cone (V) 30.00, Extractor (V) 3.00, Source Temperature (° C.) 150, Desolvation Temperature (° C.) 400, Cone Gas Flow (L/Hr) 60, Desolvation Gas Flow (L/Hr) 700
Mass range: 140 to 800 Da
DAD Wavelength range (nm): 210 to 400
Method Waters ACQUITY UPLC with the Following HPLC Gradient Conditions
(Solvent A: Water/Methanol 9:1+0.1% Formic Acid and Solvent B: Acetonitrile+0.1% Formic Acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

Where necessary, enantiomerically pure final compounds may be obtained from racemic materials as appropriate via standard physical separation techniques, such as reverse phase chiral chromatography, or through stereoselective synthetic techniques, eg, by using chiral starting materials.

A Representative Description of a Chiral Analysis Apparatus is:
Supercritical Fluid Chromatography:
Waters Acquity UPC$^2$/QDa
PDA Detector Waters Acquity UPC$^2$
Column: Daicel SFC CHIRALPAK® IC, 3 μm, 0.3 cm×10 cm, 40° C.
Mobile phase: A: CO$_2$ B: iPr gradient: 05% B in 3.8 min
ABPR: 1800 psi
Flow rate: 2.0 mL/min
Detection: 247 nm
Sample concentration: 1 mg/mL in Acetonitril/iPrôpanol 50/50
Injection: 1 μL

FORMULATION EXAMPLES

| Wettable powders | a) | b) | c) |
|---|---|---|---|
| active ingredients [components (A) and (B)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients [components (A) and (B)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

| Emulsifiable concentrate | |
|---|---|
| active ingredients [components (A) and (B)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| active ingredients [components (A) and (B)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| active ingredients [components (A) and (B)] | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| active ingredients [components (A) and (B)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredients [components (A) and (B)] | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredients [components (A) and (B)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the active ingredients [components (A) and (B)] is mixed with 2 parts of an aromatic solvent and 7 parts of toluene diisocyanate/polymethylenepolyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

LIST OF ABBREVIATIONS

AIBN=azobisisobutyronitrile
BOP-Cl=phosphoric acid bis(2-oxooxazolidide) chloride
CDI=carbonyl diimidazole
DCE=1,2-dichloroethane
DCM=dichloromethane
DIPEA=N,N-diisopropylethylamine
DMA=dimethylacetamide
DMF=dimethylformamide
EdCl=3-(ethyliminomethyleneamino)-N,N-dimethylpropan-1-amine
EtOAc=ethyl acetate
EtOH=ethyl alcohol
HCl=hydrochloric acid
HOAt=1-hydroxy-7-azabenzotriazole
HATU=1-[bis(dimethylamino)methylene]-1H-1,2,3-triazolo[4,5-b]pyridinium 3-oxid-hexafluorophosphate
mp=melting point
MeOH=methyl alcohol
NaOH=sodium hydroxide
NBS=N-bromosuccinimide
rh=relative humidity
TFAA=trifluoroacetic acid anhydride
THF=tetrahydrofuran

PREPARATION EXAMPLES

The below compound of component (B) N'-[5-bromo-2-methyl-6-(1-methyl-2-propoxy-ethoxy)-3-pyridyl]-N-ethyl-N-methyl-formamidine and its synthesis is known from WO 2015/155075, as are the syntheses of closely-related compounds described in accordance with the present invention.

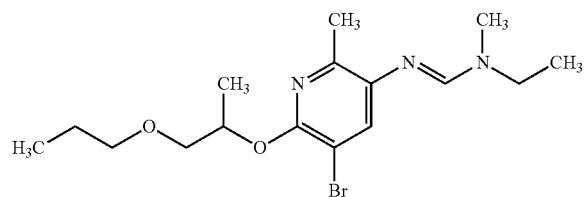

The compound of component (B) Timorex Gold™ (active ingredient tea tree (*Melaleuca alternifolia*) oil) is a plant extract available from the Stockton Group (http://www.stockton-ag.com/products/timorex-gold/).

Using the synthetic techniques described both above and below, compounds of formula (I) may be prepared accordingly.

Example 1: This example illustrates the preparation of 2-(difluoromethoxy)-N-methyl-N-[[4-[5-(trifluoromethyl)-1,2,4-oxadiazol-3-yl]phenyl]methyl]acetamide (Compound X.11 of Table T1)

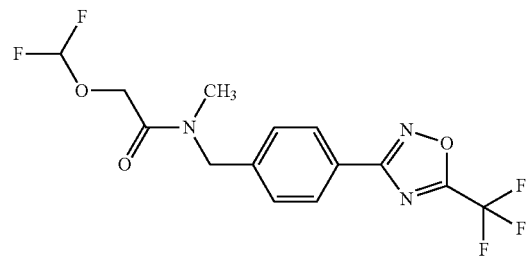

Step 1: Preparation of N'-hydroxy-4-methyl-benzamidine

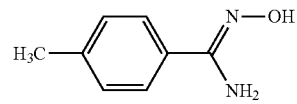

To a suspension of 4-methylbenzonitrile (35 g, 0.29 mol) in ethanol (220 mL) and water (440 mL) was added at room temperature hydroxylamine hydrochloride (41.1 g, 0.58 mol), potassium carbonate (65.4 g, 0.47 mol), and 8-hydroxyquinoline (0.22 g, 1.5 mmol). The reaction mixture was heated at 80° C. for 4 hours, then cooled to room temperature, and diluted with 2N HCl until pH 8. The volatiles were removed under reduced pressure and the reaction contents were filtered, washed with water, and dried under vacuum to afford 39.1 g of the title compound. LC/MS (Method A) retention time=0.23 minutes, 151.0 (M+H).

Step 2: Preparation of 3-(p-tolyl)-5-(trifluoromethyl)-1,2,4-oxadiazole

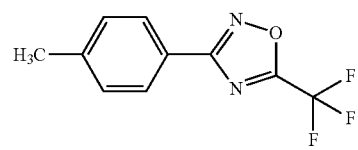

To a solution of N'-hydroxy-4-methyl-benzamidine (38.7 g, 0.25 mol) in 2-methyltetrahydrofuran (750 mL) was added TFAA at 0° C. The reaction mixture was stirred at 15° C. for two hours then diluted with water. The organic layer was separated, washed successively with a saturated aqueous sodium bicarbonate solution, a saturated aqueous ammonium chloride solution, and water then dried over sodium sulfate, filtered, and concentrated under reduced pressure. The resultant crude residue was purified by flash chromatography over silica gel (heptane/EtOAc eluent gradient 99:1 to 90:10) to afford 54.1 g of the title compound as clear oil, which solidified after storage. LC/MS (Method A) retention time=1.15 minutes, mass not detected.

$^1$H NMR (400 MHz, CDCl$_3$) δ ppm: 8.00 (d, 2H), 7.32 (d, 2H), 2.45 (s, 3H).
$^{19}$F NMR (400 MHz, CDCl$_3$) δ ppm: −65.41 (s).

Step 3a: Preparation of 3-[4-(bromomethyl)phenyl]-5-(trifluoromethyl)-1,2,4-oxadiazole

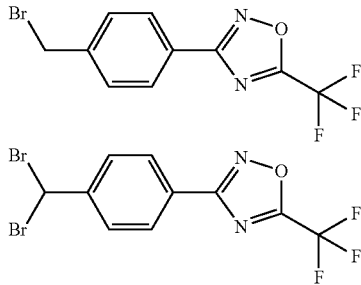

A mixture of 3-(p-tolyl)-5-(trifluoromethyl)-1,2,4-oxadiazole (56.0 g, 0.24 mol) and NBS (45.4 g, 0.25 mol) in tetrachloromethane (480 mL) under argon was heated to 70° C. AIBN (4.03 g, 24 mmol) was added and the reaction mixture was stirred at 65° C. for 18 hours. The mixture was then cooled to room temperature and diluted with dichloromethane and water. The layers were separated and the organic layer was washed with a saturated aqueous sodium bicarbonate solution, dried over sodium sulfate, filtered, and concentrated under reduced pressure. The crude residue was purified by flash chromatography over silica gel (cyclohexane/EtOAc eluent gradient 100:0 to 95:5) to afford 44.7 g of the title compound as a white solid. mp: 58-63° C.

$^1$H NMR (400 MHz, CDCl$_3$) δ ppm: 8.11 (d, 2H), 7.55 (d, 2H), 4.53 (s, 2H).
$^{19}$F NMR (400 MHz, CDCl$_3$) δ ppm: −65.32 (s).

3-[4-(dibromomethyl)phenyl]-5-(trifluoromethyl)-1,2,4-oxadiazole was isolated as by-product as white solid. mp: 61-66° C.

$^1$H NMR (400 MHz, CDCl$_3$) δ ppm: 8.15 (d, 2H), 7.73 (d, 2H), 6.68 (s, 1H).
$^{19}$F NMR (400 MHz, CDCl$_3$) δ ppm: −65.34 (s).

Step 3b: Preparation of 3-[4-(bromomethyl)phenyl]-5-(trifluoromethyl)-1,2,4-oxadiazole from 3-[4-(dibromomethyl)phenyl]-5-(trifluoromethyl)-1,2,4-oxadiazole

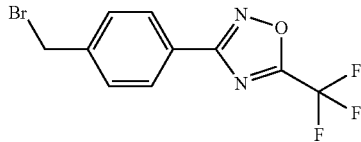

To a 1:9 ratio mixture of 3-[4-(bromomethyl)phenyl]-5-(trifluoromethyl)-1,2,4-oxadiazole and 3-[4-(dibromomethyl)phenyl]-5-(trifluoromethyl)-1,2,4-oxadiazole (10.2 g) in acetonitrile (95 mL), water (1.9 mL) and DIPEA (6.20 mL, 35.7 mmol) was added diethylphosphite (4.7 mL, 35.7 mmol) at 5° C. The mixture was stirred at 5-10° C. for two hours, aqueous 1M HCl was added, and volatiles were removed under reduced pressure. The resultant white slurry was extracted with dichloromethane and the total combined organic layer was dried over sodium sulfate, filtered, and concentrated under reduced pressure. The resultant crude residue was purified by flash chromatography over silica gel (cyclohexane/EtOAc eluent gradient 99:1 to 9:1) to afford 7.10 g of the title compound as a white solid. mp: 58-63° C.

$^1$H NMR (400 MHz, CDCl$_3$) δ ppm: 8.11 (d, 2H), 7.55 (d, 2H), 4.53 (s, 2H).
$^{19}$F NMR (400 MHz, CDCl$_3$) δ ppm: −65.32 (s).

Step 4: Preparation of N-[[4-[5-(trifluoromethyl)-1,2,4-oxadiazol-3-yl]phenyl]methyl]methanamine

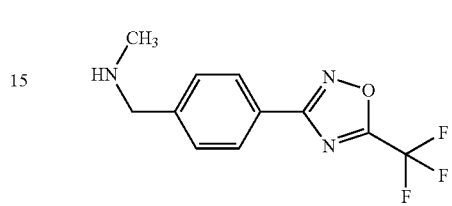

A solution of 3-[4-(bromomethyl)phenyl]-5-(trifluoromethyl)-1,2,4-oxadiazole (15 g, 46.9 mmol) in THF (20 mL) was added dropwise at room temperature to a solution of methylamine (2M in THF, 120 mL, 234.5 mmol) and stirred at room temperature for 24 hours. The solvent was removed under reduced pressure and the resultant crude material was purified by flash chromatography over silica gel (cyclohexane/EtOAc eluent gradient 1:0 to 1:1) to give 10.3 g of the title compound as a clear oil. LC/MS (Method A) retention time=0.58 minutes, 258 (M+H).

$^1$H NMR (400 MHz, CDCl$_3$) δ ppm: 8.08 (d, 2H), 7.47 (d, 2H), 3.84 (s, 2H), 2.48 (s, 3H).
$^{19}$F NMR (400 MHz, CDCl$_3$) δ ppm: −65.39 (s).

Step 5: Preparation of 2-hydroxy-N-methyl-N-[[4-[5-(trifluoromethyl)-1,2,4-oxadiazol-3-yl]phenyl]methyl]acetamide

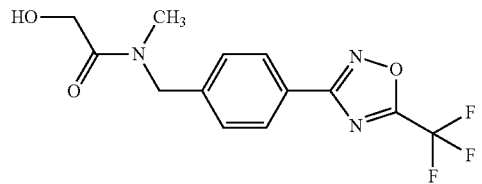

To a suspension of N-[[4-[5-(trifluoromethyl)-1,2,4-oxadiazol-3-yl]phenyl]methyl]methanamine (0.50 g, 1.94 mmol) in DMF (7.8 mL) under nitrogen atmosphere was added DIPEA (1.0 mL, 5.83 mmol) followed by 2-hydroxy acetic acid (0.22 g, 2.92 mmol), HATU (1.1 g, 2.92 mmol). After the reaction stirred overnight, the contents were diluted with an aqueous saturated sodium bicarbonate solution and extracted with ethyl acetate. The total combined organic layer was dried over sodium sulfate and filtered. The solvent was removed under reduced pressure and the resultant crude was purified by flash chromatography over silica gel (cyclohexane/EtOAc eluent gradient 95:5 to 9:1) to afford 442 mg of the title compound as a clear oil. LC/MS (Method A) retention time=0.90 minutes, 316 (M+H).
$^{19}$F NMR (400 MHz, CDCl$_3$) δ ppm: −65.34 (s).

Step 6: Preparation of 2-(difluoromethoxy)-N-methyl-N-[[4-[5-(trifluoromethyl)-1,2,4-oxadiazol-3-yl]phenyl]methyl]acetamide 2-hydroxy-N-methyl-N-[[4-[5-(trifluoromethyl)-1,2,4-oxadiazol-3-yl]phenyl]methyl]acetamide (442 mg, 1.40 mmol) was suspended in dry acetonitrile (3.4 mL, dried over 2 Å molecular sieves) and CuI (0.07 g, 0.34 mmol) was introduced. The contents were heated at 45° C. and 2,2-difluoro-2-fluorosulfonyl-acetic acid (0.20 mL, 1.89 mmol) in acetonitrile (2 mL) was introduced via syringe pump over 40 minutes. The reaction mixture was heated for 30 minutes, cooled to room temperature, quenched with water (30 mL), and extracted with ethyl acetate. The total combined organic layer was washed with brine, dried over sodium sulfate, and filtered. The solvent was removed under reduced pressure and the resultant crude was purified by flash chromatography over silica gel (cyclohexane/EtOAc eluent gradient 1:0 to 1:1) to give 22 mg of the title compound as a clear oil. LC/MS (Method A) retention time=1.02 minutes, 366 (M+H).

$^1$H NMR (400 MHz, CDCl$_3$) δ ppm: 8.12 (m, 2H), 7.40 (m, 2H), 6.44 (t, 1H), 4.69 (m, 2H), 4.58 (m, 2H), 2.96 (m, 3H).

$^{19}$F NMR (400 MHz, CDCl$_3$) δ ppm: −65.34 (s), −85.92 (s).

Example 2: This example illustrates the preparation of 1-cyclopropyl-3-methoxy-3-methyl-1-[[4-[5-(trifluoromethyl)-1,2,4-oxadiazol-3-yl]phenyl]methyl] urea (Compound X.18 of Table X)

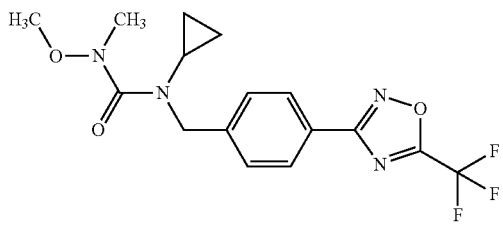

Step 1: Preparation of 1 N-[[4-[5-(trifluoromethyl)-1,2,4-oxadiazol-3-yl]phenyl]methyl]cyclopropanamine

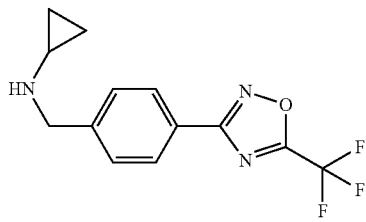

A solution of 3-[4-(bromomethyl)phenyl]-5-(trifluoromethyl)-1,2,4-oxadiazole (2.50 g, 8.1 mmol) in dichloromethane (5 mL) was added over 2 hours at room temperature to a solution of cyclopropanamine (3.7 g, 65 mmol) and N-ethyl-N-isopropyl-propan-2-amine (1.4 mL, 8.1 mmol) in dichloromethane (10 mL). The mixture was stirred at room temperature for 30 minutes, poured into water and then extracted with dichloromethane. The total combined organic layer was washed with brine, dried over sodium sulfate, and filtered. The solvent was removed under reduced pressure and the resultant crude residue was purified by flash chromatography over silica gel (cyclohexane/EtOAc eluent gradient 1:0 to 1:1) to give 1.18 g of the title compound as a white solid, LC/MS (Method A) retention time=0.71 minutes, 300 (M+H).

$^1$H NMR (400 MHz, CDCl$_3$) δ ppm: 8.06 (d, 2H), 7.49 (d, 2H), 3.92 (s, 2H), 2.18 (m, 1H), 1.85 (brs, 1H), 0.42 (m, 2H), 0.39 (m, 2H).

$^{19}$F NMR (400 MHz, CDCl$_3$) δ ppm: −65.36 (s).

Step 2: Preparation of 1-cyclopropyl-3-methoxy-3-methyl-1-[[4-[5-(trifluoromethyl)-1,2,4-oxadiazol-3-yl]phenyl]methyl]urea To a stirred suspension of N-[[4-[5-(trifluoromethyl)-1,2,4-oxadiazol-3-yl]phenyl]methyl]cyclopropanamine (0.15 g, 0.53 mmol) in dichloromethane (3 mL) at 0° C. was added triethylamine (0.15 mL, 1.06 mmol) followed by N-methoxy-N-methylcarbamoyl chloride (0.07 g, 0.58 mmol). After 4 hours, the reaction mixture volatiles were removed under reduced pressure and the resultant crude residue was purified by flash chromatography over silica gel (cyclohexane/EtOAc eluent gradient 95:5 to 9:1) to afford 183 mg of the desired product as a light yellow oil. LC/MS (Method A) retention time=1.10 minutes, 371 (M+H).

$^1$H NMR (400 MHz, CDCl$_3$) δ ppm: 8.08 (d, 2H), 7.44 (d, 2H), 4.62 (s, 2H), 3.68 (s, 3H), 3.08 (s, 3H), 2.68 (m, 1H), 0.74 (m, 4H).

Example 3: This example illustrates the preparation of 2-methoxy-N-(2,2,2-trifluoroethyl)-N-[[4-[5-(trifluoromethyl)-1,2,4-oxadiazol-3-yl]phenyl]methyl] acetamide (Compound X.09 of Table X)

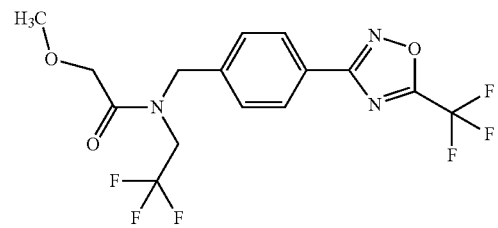

Step 1: Preparation of the intermediate 2,2,2-trifluoro-N-[[4-[5-(trifluoromethyl)-1,2,4-oxadiazol-3-yl]phenyl]methyl]ethanamine

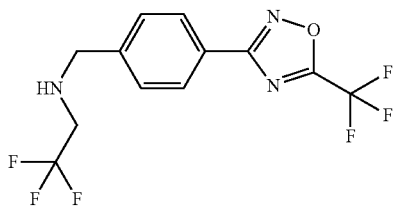

To a solution of 3-[4-(bromomethyl)phenyl]-5-(trifluoromethyl)-1,2,4-oxadiazole (1.5 g, 4.69 mmol) in dichloromethane (10 mL) was introduced dropwise DIPEA (0.82 mL, 4.69 mmol) followed by 2,2,2-trifluoroethanamine (2.94 mL, 37.5 mmol). The reaction mixture was stirred at room temperature for 24 hours then poured into water and extracted with dichloromethane. The total combined organic layer was dried over sodium sulfate and filtered. The solvent was removed under reduced pressure and the resultant crude residue was purified by flash chromatography over silica gel (cyclohexane/EtOAc eluent gradient 1:0 to 0:1) to give 1.53 g of the title compound as a clear oil.

$^1$H NMR (400 MHz, CDCl$_3$) δ ppm: 8.09 (d, 2H), 7.51 (d, 2H), 4.00 (s, 2H), 3.22 (q, 2H), 1.71 (s, 1H).

Step 2: Preparation of 2-methoxy-N-(2,2,2-trifluoroethyl)-N-[[4-[5-(trifluoromethyl)-1,2,4-oxadiazol-3-yl]phenyl]methyl]acetamide To a suspension of 2,2,2-trifluoro-N-[[4-[5-(trifluoromethyl)-1,2,4-oxadiazol-3-yl]phenyl]methyl]ethanamine (0.1 g, 0.31 mmol) in dichloromethane (6 mL) at 0° C. was added triethylamine (0.09 mL, 0.62 mmol) followed by 2-methoxyacetyl chloride (0.03 mL, 0.32 mmol). The reaction mixture stirred overnight, was reduced under reduced pressure, and the resultant crude residue was subjected to flash chromatography over silica gel (heptane/EtOAc eluent gradient 9:1 to 1:9) to afford 116 mg of the desired product as a white solid mp: 92-95° C. LC/MS (Method A) retention time=1.08 minutes, 398 (M+H).

$^1$H NMR (400 MHz, CDCl$_3$) δ ppm: 8.12 (m, 2H), 7.36 (m, 2H), 4.82 (s, 2H), 4.08 (m, 2H), 3.98 (m, 2H), 3.45 (s, 3H).

Example 4: This example illustrates the preparation of intermediate N-propoxy-1-[4-[5-(trifluoromethyl)-1,2,4-oxadiazol-3-yl]phenyl]methanamine

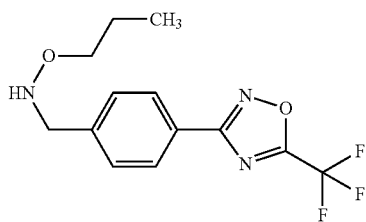

A solution of 3-[4-(bromomethyl)phenyl]-5-(trifluoromethyl)-1,2,4-oxadiazole (1.30 g, 4.06 mmol) in dichloromethane (10 mL) was added dropwise to a solution of O-propylhydroxylamine hydrochloride (3.74 g, 32.5 mmol) and DIPEA (6.40 mL, 36.6 mmol) in dichloromethane (6 mL). The reaction mixture was stirred at room temperature for 24 hours then poured onto water and the layers were separated. The aqueous layer was extracted with dichloromethane and the total combined organic layer was washed with brine, dried over sodium sulfate, and filtered. The solvent was removed under reduced pressure and the resultant crude was purified by flash chromatography over silica gel (cyclohexane/EtOAc eluent gradient 1:0 to 1:1) to give 0.92 g of the title compound as a clear oil. LC/MS (Method A) retention time=1.12 minutes, 302 (M+H).

$^1$H NMR (400 MHz, CDCl$_3$) δ ppm: 8.09 (d, 2H), 7.02 (d, 2H), 5.70 (sbr, 1H), 4.11 (s, 2H), 3.59 (m, 2H), 1.52 (m, 2H), 0.86 (s, 3H).

$^{19}$F NMR (400 MHz, CDCl$_3$) δ ppm: −65.33 (s).

Example 5: This example illustrates the preparation 1-[[3-fluoro-4-[5-(trifluoromethyl)-1,2,4-oxadiazol-3-yl]phenyl]methyl]-1-methoxy-3-methyl-urea (Compound X.21 of Table X)

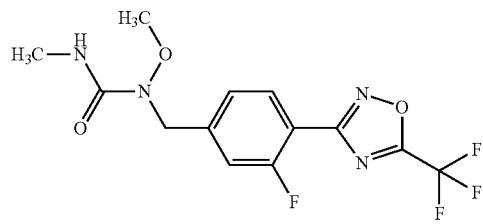

Step 1: Preparation of 2-fluoro-N'-hydroxy-4-methyl-benzamidine

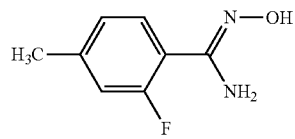

To a suspension of 2-fluoro-4-methylbenzonitrile (5 g, 37.0 mmol) in ethanol (125 mL) at 25° C. was added hydroxylamine hydrochloride (7.7 g, 111 mmol) and the reaction mixture was heated at 80° C. for 2 hours. After cooling to room temperature the volatiles were removed under reduced pressure thus affording a white solid that was used in the next transformation without additional purification. LC/MS (Method A) retention time=1.14 minutes, 169.2 (M+H).

$^1$H NMR (400 MHz, CDCl$_3$) δ ppm: 7.96 (t, 1H), 7.11 (m, 2H), 2.45 (s, 3H).

Step 2: Preparation of 3-(2-fluoro-4-methyl-phenyl)-5-(trifluoromethyl)-1,2,4-oxadiazole

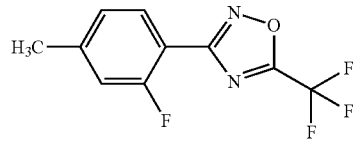

To a solution of 2-fluoro-N'-hydroxy-4-methyl-benzamidine (37 mmol) in tetrahydrofuran (122 mL) cooled via an ice bath was added TFAA (7.71 mL, 55.5 mmol). The reaction mixture was stirred at 25° C. overnight and then diluted with water. The organic layer was separated, washed successively with a saturated aqueous sodium bicarbonate solution, a saturated aqueous ammonium chloride solution, and water then dried over sodium sulfate, filtered, and concentrated under reduced pressure. The resultant crude residue was purified by flash chromatography over silica gel (cyclohexane/EtOAc eluent gradient 99:1 to 1:1) to afford 6.6 g of the title compound as an amorphous white solid. LC/MS (Method A) retention time=1.14 minutes, 247 (M+H).

¹H NMR (400 MHz, CDCl₃) δ ppm: 8.00 (d, 1H), 7.32 (d, 2H), 2.45 (s, 3H).

¹⁹F NMR (400 MHz, CDCl₃) δ ppm: −65.3 (s), 108.1 (s).

Step 3a: Preparation of 3-[4-(bromomethyl)phenyl]-5-(trifluoromethyl)-1,2,4-oxadiazole

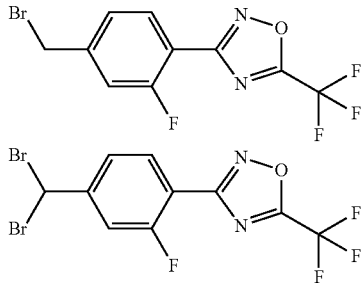

A mixture of 3-(2-fluoro-4-methyl-phenyl)-5-(trifluoromethyl)-1,2,4-oxadiazole (4.2 g, 17.1 mmol) and NBS (3.11 g, 17.1 mmol) in tetrachloromethane (34.3 mL) was heated to 70° C. AIBN (0.29 g, 1.71 mmol) was introduced and the reaction mixture stirred at 65° C. for 18 hours. The contents were cooled to 25° C., diluted with dichloromethane and water, and the layers were separated. A succinimide by-product was removed via filtration and the solvent was removed under reduced pressure to afford a brown gum. This residue was purified by flash chromatography over silica gel (cyclohexane/EtOAc 100:0 to 4:1) to afford 1.7 g of the title compound as a white solid. LC/MS (Method A) retention time=1.13 minutes, (M+H) not detected.

¹H NMR (400 MHz, CDCl₃) δ ppm: 8.09 (t, 1H), 7.34 (m, 2H), 4.49 (s, 2H).

¹⁹F NMR (400 MHz, CDCl₃) δ ppm: −65.18 (s), −106.2 (s).

3-[4-(dibromomethyl)phenyl]-5-(trifluoromethyl)-1,2,4-oxadiazole was isolated as by-product in the form of a beige solid (4.0 g, 58% yield) LC/MS (Method A) retention time=1.20 minutes, (M+H) not detected.

¹H NMR (400 MHz, CDCl₃) δ ppm: 8.14 (d, 1H), 7.52 (dd, 2H), 6.63 (s, 1H).

Step 3b: Preparation of 3-[4-(bromomethyl)-2-fluoro-phenyl]-5-(trifluoromethyl)-1,2,4-oxadiazole from 33-[4-(dibromomethyl)-2-fluoro-phenyl]-5-(trifluoromethyl)-1,2,4-oxadiazole

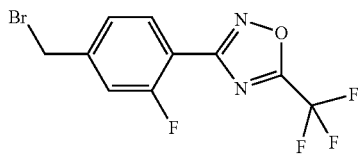

To a 1:20 mixture of 3-[4-(bromomethyl)-2-fluoro-phenyl]-5-(trifluoromethyl)-1,2,4-oxadiazole and 3-[4-(dibromomethyl)-2-fluoro-phenyl]-5-(trifluoromethyl)-1,2,4-oxadiazole (4.0 g, 9.9 mmol) in acetonitrile (37 mL), water (0.8 mL) and DIPEA (2.59 mL, 14.8 mmol) at 5° C. was added diethylphosphite (2.0 mL, 14.8 mmol). The mixture was stirred at 5-10° C. for 2 hours, then water and aqueous 1M HCl were added. Volatiles were removed under reduced pressure and the resultant white slurry was extracted with dichloromethane. The total combined organic layer was dried over sodium sulfate and filtered. The solvent was removed under reduced pressure and the resultant light orange colored crude residue was purified by flash chromatography over silica gel (cyclohexane/EtOAc eluent gradient 99:1 to 1:1) to afford 2.2 g of the title compound as a white solid. LC/MS (Method A) retention time=1.13 minutes, (M+H) not detected.

¹H NMR (400 MHz, CDCl₃) δ ppm: 8.09 (t, 1H), 7.34 (m, 2H), 4.49 (s, 2H).

¹⁹F NMR (400 MHz, CDCl₃) δ ppm: −65.18 (s), −106.2 (s).

Step 4: Preparation of 1-[3-fluoro-4-[5-(trifluoromethyl)-1,2,4-oxadiazol-3-yl]phenyl]-N-methoxy-methanamine

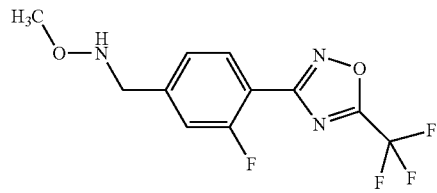

To a solution of O-methylhydroxylamine hydrochloride (4.9 g, 59 mmol) in dichloromethane (15 mL) was introduced dropwise DIPEA (12 mL, 66 mmol) followed by a solution of 3-[4-(bromomethyl)-2-fluorophenyl]-5-(trifluoromethyl)-1,2,4-oxadiazole (1.2 g, 3.7 mmol) in dichloromethane (5 mL). After 18 hours, water was introduced (10 mL) and the reaction contents were extracted twice with dichloromethane and the total combined organic layer was dried over sodium sulfate then filtered. The resultant residue was purified by flash chromatography over silica gel (cyclohexane/EtOAc eluent gradient 1:0 to 1:1) to afford 410 mg of the title compound as a colorless oil LC/MS (Method A) retention time=1.01 minutes, (M+H) not detected.

¹H NMR (400 MHz, CDCl₃) δ ppm: 8.05 (t, 1H), 7.45 (m, 2H), 5.85 (brs, 1H), 4.12 (s, 2H), 3.50 (s, 3H).

¹⁹F NMR (400 MHz, CDCl₃) δ ppm: −65.21 (s), −107.33 (s).

Step 5: Preparation of 1-[[3-fluoro-4-[5-(trifluoromethyl)-1,2,4-oxadiazol-3-yl]phenyl]methyl]-1-methoxy-3-methyl-urea To a solution of 1-[3-fluoro-4-[5-(trifluoromethyl)-1,2,4-oxadiazol-3-yl]phenyl]-N-methoxy-methanamine (20 mg, 0.07 mmol) in dichloromethane (0.23 mL) was added N-methylcarbamoyl chloride (0.012 g, 0.14 mmol) and triethylamine (0.02 mL, 0.13 mmol). After 1 hour, the reaction mixture was concentrated under reduced pressure and the resultant crude residue was purified by flash chromatography over silica gel (cyclohexane/EtOAc eluent gradient 99:1 to 1:1) to provide 12 mg of the desired product as a gum. LC/MS (Method A) retention time=0.97 minutes, 349 (M+H).

¹H NMR (400 MHz, CDCl₃) δ ppm: 8.04 (t, 1H), 7.31 (m, 2H), 5.81 (m, 1H), 4.71 (s, 2H), 3.60 (s, 3H), 2.87 (d, 3H).

¹⁹F NMR (400 MHz, CDCl₃) δ ppm: −65.17 (s), −107.10 (s).

Example 6: This example illustrates the preparation of N-[[2,3-difluoro-4-[5-(trifluoromethyl)-1,2,4-oxadiazol-3-yl]phenyl]methyl]-N-methoxy-cyclopropanecarboxamide (Compound X.10 of Table X)

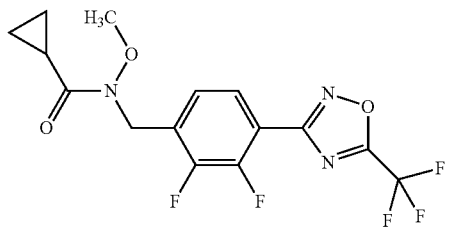

Step 1: Preparation of 2,3-difluoro-N'-hydroxy-4-methyl-benzamidine

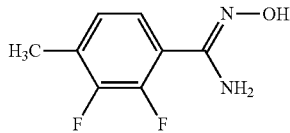

To a suspension of 2,3-difluoro-4-methylbenzonitrile (5.0 g, 32.6 mmol) in ethanol (111 mL) at 25° C. was added hydroxylamine hydrochloride (4.5 g, 65.3 mmol). The reaction mixture was heated at 80° C. for 2 hours. After cooling to room temperature, the volatiles were removed under reduced pressure thus affording a white solid that was used in the next transformation without purification.

$^1$H NMR (400 MHz, CDCl$_3$) δ ppm: 7.30 (m, 1H), 6.95 (m, 1H), 6.50 (brs, 1H), 5.05 (brs, 2H), 2.30 (s, 3H).

Step 2: Preparation of 3-(2,3-difluoro-4-methyl-phenyl)-5-(trifluoromethyl)-1,2,4-oxadiazole

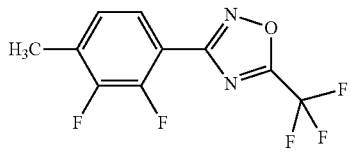

To a solution of 2,3-difluoro-N'-hydroxy-4-methyl-benzamidine (2.6 mmol) in tetrahydrofuran (108 mL) cooled via an ice bath was added TFAA (6.9 mL, 49 mmol). The reaction mixture was stirred at 25° C. overnight and then diluted with water. The organic layer was separated, washed successively with a saturated aqueous sodium bicarbonate solution, a saturated aqueous ammonium chloride solution, and water then dried over sodium sulfate, filtered, and concentrated under reduced pressure. The title compound (6.6 g) was isolated as a light brown solid that was used in the next transformation without further purification. LC/MS (Method A) retention time=1.16 minutes, 265 (M+H).

$^1$H NMR (400 MHz, CDCl$_3$) δ ppm: 7.76 (d, 1H), 7.12 (d, 1H), 2.41 (s, 3H).

$^{19}$F NMR (400 MHz, CDCl$_3$) δ ppm: −65.41 (s), −133.3 (s), −140.1 (s).

Step 3: Preparation of 3-[4-(bromomethyl)-2,3-difluoro-phenyl]-5-(trifluoromethyl)-1,2,4-oxadiazole

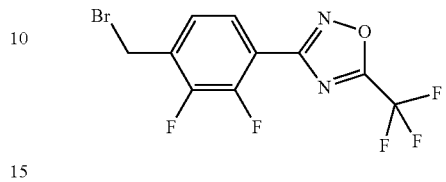

A mixture of 3-(2,3-difluoro-4-methyl-phenyl)-5-(trifluoromethyl)-1,2,4-oxadiazole (6.0 g, 22.6 mmol) and NBS (7.17 g, 10.0 mmol) in tetrachloromethane (79 mL) under argon was heated to 70° C. AIBN (0.68 g, 3.95 mmol) was added and the reaction mixture stirred at 65° C. for 36 hours. The mixture was cooled to 25° C., diluted with dichloromethane, water, and the layers were separated. The succinimide by-product was removed via filtration and volatiles were removed under reduced pressure. The resultant crude residue was purified by flash chromatography over silica gel (cyclohexane/EtOAc eluent gradient 100:0 to 4:1) to afford 4.8 g of the title compound as a white solid. LC/MS (Method A) retention time=1.16 minutes, 344 (M+H).

$^1$H NMR (400 MHz, CDCl$_3$) δ ppm: 7.80 (m, 1H), 7.37 (m, 1H), 4.55 (s, 2H).

$^{19}$F NMR (400 MHz, CDCl$_3$) δ ppm: −65.1 (s), −131.2 (s), −139.1 (s).

Step 4: Preparation of 1-[2,3-difluoro-4-[5-(trifluoromethyl)-1,2,4-oxadiazol-3-yl]phenyl]-N-methoxy-methenamine

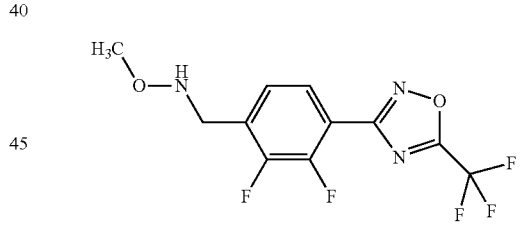

A solution of O-methylhydroxylamine hydrochloride (3.5 g, 42 mmol) in dichloromethane (8 mL) was treated dropwise with DIPEA (8.3 mL, 47 mmol) followed by a solution of 3-[4-(bromomethyl)-2,3-difluoro-phenyl]-5-(trifluoromethyl)-1,2,4-oxadiazole (2.0 g, 5.2 mmol) in dichloromethane (5 mL). After 18 hours, water was introduced (10 mL), the reaction contents were extracted twice with dichloromethane, and the total combined organic layer was dried over sodium sulfate and filtered. The resultant residue was purified by flash chromatography over silica gel (cyclohexane/EtOAc eluent gradient 1:0 to 1:1) to afford 1.10 g of the title compound as a pale yellow oil. LC/MS (Method A) retention time=1.03 minutes, 310 (M+H).

$^1$H NMR (400 MHz, CDCl$_3$) δ ppm: 7.84 (t, 1H), 7.38 (t, 1H), 5.87 (brs, 1H), 4.20 (s, 2H), 3.52 (s, 3H).

$^{19}$F NMR (400 MHz, CDCl$_3$) δ ppm: −65.21 (s), −132.53 (s), −147.50 (s).

Step 5: Preparation of N-[[2,3-difluoro-4-[5-(trifluoromethyl)-1,2,4-oxadiazol-3-yl]phenyl]methyl]-N-methoxy-cyclopropanecarboxamide To a solution of 1-[2,3-difluoro-4-[5-(trifluoromethyl)-1,2,4-oxadiazol-3-yl]phenyl]-N-methoxy-methanamine (0.18 g, 0.58 mmol) in dichloromethane (2.9 mL) was added cyclopropanecarbonyl chloride (0.06 mL, 0.61 mmol) followed by triethylamine (0.16 mL, 1.16 mmol). After 1 hour, the reaction mixture was concentrated under reduced pressure and the crude residue was purified by flash chromatography over silica gel (cyclohexane/EtOAc eluent gradient 99:1 to 1:1) to provide 207 mg of the title compound as a gum. LC/MS (Method A) retention time=1.11 minutes, 378 (M+H).

Example 7a: This example illustrates the preparation of N-ethyl-2-methyl-N-[[4-[5-(trifluoromethyl)-1,2,4-oxadiazol-3-yl]phenyl]methyl]propanamide (Compound X.07 of Table X)

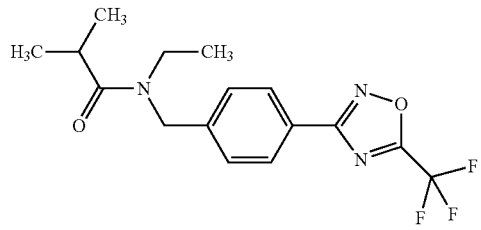

Step 1: Preparation of N-[[4-[5-(trifluoromethyl)-1,2,4-oxadiazol-3-yl]phenyl]methyl]ethanamine

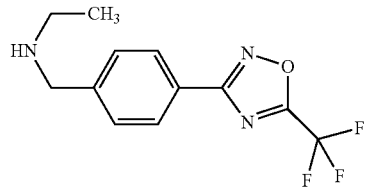

A solution of 3-[4-(bromomethyl)phenyl]-5-(trifluoromethyl)-1,2,4-oxadiazole (1.50 g, 4.69 mmol) in dichloromethane (9.4 mL) was added dropwise at room temperature to a solution of ethylamine 2M in MeOH (12 mL, 24.0 mmol). The mixture was stirred at room temperature for 24 hours then poured into water and the layers were separated. The aqueous layer was extracted with dichloromethane and the total combined organic layer was washed with brine, dried over sodium sulfate, and filtered. The solvent was removed under reduced pressure and the resultant crude was purified by flash chromatography over silica gel (cyclohexane/EtOAc eluent gradient 1:0 to 1:1) to give 0.92 g of the title compound as a white solid mp: 102-112° C., LC/MS (Method A) retention time=0.66 minutes, 272 (M+H).
$^1$H NMR (400 MHz, CDCl$_3$) δ ppm: 8.01 (d, 2H), 7.57 (d, 2H), 3.86 (q, 2H), 3.29 (brs, 1H), 2.53 (q, 2H), 1.05 (t, 3H).
$^{19}$F NMR (400 MHz, CDCl$_3$) δ ppm: −64.77 (s).

Step 2: Preparation of N-ethyl-2-methyl-N-[[4-[5-(trifluoromethyl)-1,2,4-oxadiazol-3-yl]phenyl]methyl]propanamide To a suspension of N-[[4-[5-(trifluoromethyl)-1,2,4-oxadiazol-3-yl]phenyl]methyl]ethanamine (4.8 g, 18 mmol) in dichloromethane (58 mL) at 0° C. was added triethylamine (4.9 mL, 35 mmol) followed by 2-methylpropanoyl chloride (2.0 mL, 19 mmol). The reaction mixture stirred for 1 hour, then a saturated aqueous ammonia chloride solution was introduced followed by extraction with ethyl acetate. The total combined organic layer was dried over sodium sulfate and filtered. The solvent was removed under reduced pressure and the resultant crude residue was subjected to flash chromatography over silica gel (cyclohexane/EtOAc eluent gradient 9:1 to 1:9) to afford 5.1 g of the desired product as an orange oil. LC/MS (Method A) retention time=1.11 minutes, 342.6 (M+H).
$^1$H NMR (400 MHz, CDCl$_3$) δ ppm: 8.07 (m, 2H), 7.36 (m, 2H), 4.66 (m, 2H), 3.36 (m, 2H), 2.87 (m, 1H), 1.15 (m, 9H).
$^{19}$F NMR (400 MHz, CDCl$_3$) δ ppm: −64.36 (s).

Example 7b: This example illustrates an alternative preparation of N-ethyl-2-methyl-N-[[4-[5-(trifluoromethyl)-1,2,4-oxadiazol-3-yl]phenyl]methyl]propanamide (Compound X.07 of Table X)

Step 1: Preparation of 4-(ethylaminomethyl)benzonitrile

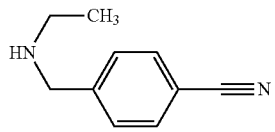

To a solution of 4-(chloromethyl)benzonitrile (3.0 g, 19.4 mmol) in tetrahydrofuran (30 mL) heated at 40° C. was added a 70% aqueous ethylamine solution (4 equiv., 77.6 mmol) and the reaction was heated at 40° C. for 16 hours. Upon cooling to 25° C., the reaction contents were diluted with water (25 mL) and tert-butyl methyl ether (50 mL) and the layers were separated. The aqueous layer was extracted with tert-butyl methyl ether and the total combined organic fraction was washed with brine, dried over sodium sulfate, and filtered. The solvent was removed under reduced pressure to give 3.05 g of the title compound as a yellow gum that was used in the next transformation without further purification.
$^1$H NMR (400 MHz, CDCl$_3$) δ ppm: 7.61 (d, 2H), 7.42 (d, 2H), 3.85 (s, 2H), 2.53 (q, 2H), 1.13 (t, 3H).

Step 2: Preparation of N-[(4-cyanophenyl)methyl]-N-ethyl-2-methyl-propanamide

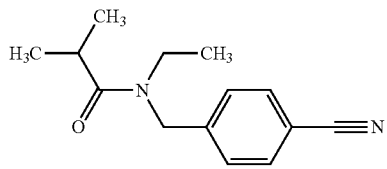

To a suspension of 4-(ethylaminomethyl)benzonitrile (2.0 g, 11.2 mmol) in toluene (13 mL) at 0° C. was added sodium hydroxide (0.50 g, 12.3 mmol) as a water solution (6.6 mL) followed by 2-methylpropanoyl chloride (1.38 g, 12.3 mmol). The ice bath was removed and the reaction mixture stirred for 24 hours. After, the reaction contents were diluted water (100 mL) and tert-butyl methyl ether (100 mL) then the layers were separated. The aqueous layer was extracted with tert-butyl methyl ether and the total combined organic fraction was dried over sodium sulfate and filtered. The solvent was removed under reduced pressure to afford 2.65 g of the desired product as an orange oil that was used in the next transformation without further purification.

¹H NMR (400 MHz, CDCl₃) δ ppm: 7.58 (m, 2H), 7.30 (m, 2H), 4.61 (m, 2H), 3.49 (m, 2H), 2.85 (m, 1H), 1.17 (m, 9H).

Step 3: Preparation of N-ethyl-N-[[4-(N-hydroxycarbamimidoyl)phenyl]methyl]-2-methyl-propanamide

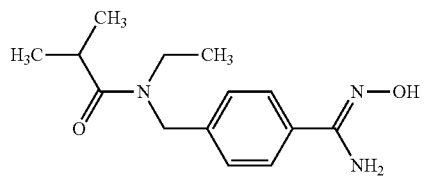

To a solution of N-[(4-cyanophenyl)methyl]-N-ethyl-2-methyl-propanamide (2.80 g, 11 mmol) and ethanol (28 mL) was introduced a 50% aqueous hydroxylamine solution (1.5 equiv., 17 mmol). After 18 hours, the reaction contents were concentrated under reduced pressure and dried under vacuum. Water (10 mL) was introduced and the contents were stirred for 15 minutes. The resultant white solid was filtered and dried under vacuum to afford 2.52 mg of the title compound as a white solid that was used in the next transformation without further purification.

¹H NMR (400 MHz, DMSO-d₆) δ ppm: 9.60 (sbr, 1H), 7.63 (m, 2H), 7.17 (m, 2H), 4.55 (m, 2H), 3.31 (m, 1H), 3.27 (m, 2H), 1.07 (m, 9H).

Step 4: Preparation of N-ethyl-2-methyl-N-[[4-[5-(trifluoromethyl)-1,2,4-oxadiazol-3-yl]phenyl]methyl]propanamide A 30 mL Schlenk tube, connected to trap-1 (empty) followed by trap-2 (filled with an 4N NaOH aqueous solution), was charged with N-ethyl-N-[[4-(N-hydroxycarbamimidoyl)phenyl]methyl]-2-methyl-propanamide (2.00 g, 7.22 mmol), ethyl acetate (20 mL), and pyridine (0.88 mL, 10.8 mmol). The contents were stirred for 10 minutes, then to the resultant white suspension was introduced 2,2,2-trifluoroacetyl chloride (1.05 g, 7.94 mmol) by gentle bubbling. The reaction media became colorless upon stirring at 25° C. and after 1 hour the reaction contents were diluted with ethyl acetate, washed with water, dried over sodium sulfate, and concentrated under reduced pressure to afford 2.5 g of the title compound as an orange oil. LC/MS (Method A) retention time=1.11 minutes, 342.6 (M+H).

¹H NMR (400 MHz, CDCl₃) δ ppm: 8.07 (m, 2H), 7.36 (m, 2H), 4.66 (m, 2H), 3.36 (m, 2H), 2.87 (m, 1H), 1.15 (m, 9H).

¹⁹F NMR (400 MHz, CDCl₃) δ ppm: −64.36 (s).

Example 8a: This example illustrates the preparation of N-methoxy-N-[[4-[5-(trifluoromethyl)-1,2,4-oxadiazol-3-yl]phenyl]methyl]cyclopropanecarboxamide (Compound X.01 of Table X)

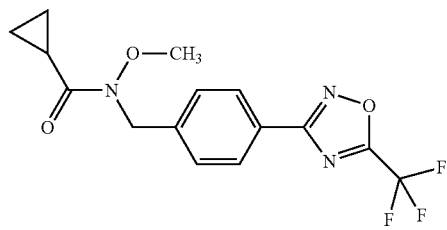

Step 1: Preparation of N-methoxy-1-[4-[5-(trifluoromethyl)-1,2,4-oxadiazol-3-yl]phenyl]methanamine

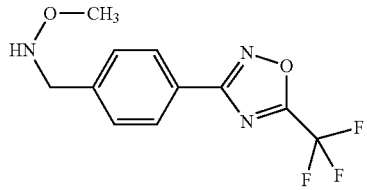

To a solution of O-methylhydroxylamine hydrochloride (11.2 g, 131.3 mmol) in dichloromethane (91 mL) was introduced DIPEA (19.1 g, 147.7 mmol) via dropwise addition. After 20 minutes, 3-[4-(bromomethyl)phenyl]-5-(trifluoromethyl)-1,2,4-oxadiazole (14.0 g, 16.4 mmol) was introduced as a dichloromethane (4 mL) solution. The reaction mixture was stirred at room temperature for 24 hours, then poured into water and the layers were separated. The organic layer was washed with water, the organic fraction was concentrated under reduced pressure, and the resultant crude residue was purified by flash chromatography over silica gel (cyclohexane/EtOAc eluent gradient 1:0 to 7:3) to give 4.4 g of the title compound as a yellowish oil.

¹H NMR (400 MHz, CDCl₃) δ ppm: 8.09 (d, 2H), 7.53 (d, 2H), 5.33 (brs, 1H), 4.12 (s, 2H), 3.50 (s, 3H).

¹⁹F NMR (400 MHz, CDCl₃) δ ppm: −65.32 (s).

Step 2: Preparation of N-methoxy-N-[[4-[5-(trifluoromethyl)-1,2,4-oxadiazol-3-yl]phenyl]methyl]cyclopropanecarboxamide To a suspension of N-methoxy-1-[4-[5-(trifluoromethyl)-1,2,4-oxadiazol-3-yl]phenyl]methanamine (0.11 g, 0.38 mmol) in dichloromethane (2.8 mL) was introduced triethylamine (0.16 mL, 1.14 mmol) followed by cyclopropanecarboxylic acid (0.4 mL, 0.49 mmol) and EDCl (0.15 g, 0.76 mmol). After 18 hours, the contents were diluted with an aqueous 1M HCl solution and extracted with dichloromethane. The total combined organic layer was dried over sodium sulfate and filtered. The solvent was removed under reduced pressure and the resultant crude residue was purified by flash chromatography over silica gel (cyclohexane/EtOAc eluent gradient 99:1 to 8:2) to afford 126 mg of the title compound as a white solid, mp: 35-38° C., LC/MS (Method A) retention time=0.99 minutes, 316.3 (M+H).

$^1$H NMR (400 MHz, CDCl$_3$) δ ppm: 8.09 (d, 2H), 7.53 (d, 2H), 4.87 (s, 2H), 3.73 (s, 3H), 2.19 (m, 1H), 1.05 (m, 2H), 0.86 (m, 2H).

$^{19}$F NMR (400 MHz, CDCl$_3$) δ ppm: −65.33 (s).

Example 8b: This example illustrates an alternative preparation of N-methoxy-N-[[4-[5-(trifluoromethyl)-1,2,4-oxadiazol-3-yl]phenyl]methyl]cyclopropanecarboxamide (Compound X.01 of Table X)

Step 1: Preparation of N-methoxycyclopropanecarboxamide

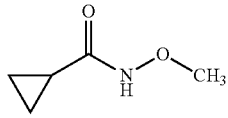

To a solution of O-methylhydroxylamine (0.80 g, 21.8 mmol) and potassium carbonate (0.52 mL, 2.88 mmol) in ethyl acetate (7.7 mL) cooled via ice bath was introduced dropwise cyclopropanecarbonyl chloride (2.0 g, 18.2 mmol) over 30 minutes. The ice bath was removed and after the contents were stirred for 2 hours EtOH (5 mL) was introduced and the contents were stirred for an additional 30 minutes. The solids were filtered then dried under vacuum to afford 2.14 g of the title compound as a white solid.

$^1$H NMR (400 MHz, DMSO-d$_6$) δ ppm: 11.13 (s, 1H), 3.57 (s, 3H), 1.34 (m, 1H), 0.87 (m, 1H), 0.68 (m, 3H).

Step 2: Preparation of N-[(4-cyanophenyl)methyl]-N-methoxy-cyclopropanecarboxamide

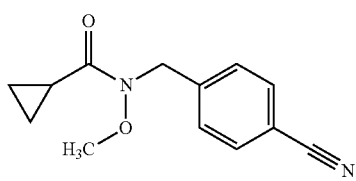

To a solution of N-methoxycyclopropanecarboxamide (0.67 g, 5.50 mmol) in acetonitrile (10 mL) was introduced potassium carbonate (0.80 g, 5.50 mmol) followed by 4-(bromomethyl)benzonitrile (1.0 g, 5.50 mmol). The reaction was heated at 60° C. during 8 hours then cooled to 25° C. and quenched with water. The contents were extracted with ethyl acetate and the total combined organic layer was dried with sodium sulfate, filtered, and concentrated under reduced pressure. The resultant crude was purified by flash chromatography over silica gel (cyclohexane/EtOAc eluent gradient 1:0 to 7:3) to give 1.0 g of the title compound as a yellowish oil.

$^1$H NMR (400 MHz, CDCl$_3$) δ ppm: 7.61 (d, 2H), 7.42 (d, 2H), 4.84 (s, 2H), 3.74 (s, 3H), 2.18 (m, 1H), 1.04 (m, 2H), 0.89 (m, 2H).

Step 3: Preparation of N-[[4-(N-hydroxycarbamimidoyl)phenyl]methyl]-N-methoxy-cyclopropanecarboxamide

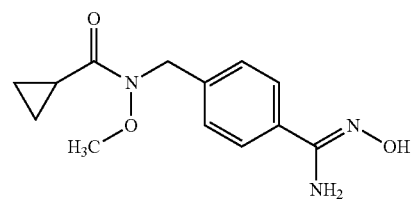

To a solution of N-[(4-cyanophenyl)methyl]-N-methoxy-cyclopropanecarboxamide (0.50 g, 2.30 mmol) and ethanol (2.5 mL) was introduced a 50% aqueous hydroxylamine solution (0.18 mL, 2.99 mmol). The reaction was then heated at 80° C. for 2 hours, cooled to 25° C., and concentrated under reduced pressure. The contents were basified to pH 8 with using an aqueous 30% NaOH solution, extracted with EtOAc, and then the total combined organic fraction was concentrated under reduced pressure and dried under vacuum to afford 270 mg of the title compound as a white solid.

$^1$H NMR (400 MHz, DMSO-d$_6$) δ ppm: 9.60 (s, 1H), 7.62 (d, 2H), 7.28 (d, 2H), 5.77 (s, 2H), 4.55 (s, 2H), 3.71 (s, 3H), 2.17 (m, 1H), 0.82 (m, 4H).

Step 4: Preparation of N-methoxy-N-[[4-[5-(trifluoromethyl)-1,2,4-oxadiazol-3-yl]phenyl]methyl]cyclopropanecarboxamide To a 30 mL Schlenk tube connected to trap-1 (empty) followed by trap-2 (filled with an 4N NaOH aqueous solution) was added N-[[4-(N-hydroxycarbamimidoyl)phenyl]methyl]-N-methoxy-cyclopropanecarboxamide (1.05 g, 4.00 mmol), ethyl acetate (20 mL), and pyridine (0.49 mL, 6.0 mmol). The contents were stirred for 10 minutes then cooled to 0° C. To the resultant white suspension was introduced 2,2,2-trifluoroacetyl chloride (0.58 g, 4.40 mmol) by gentle bubbling. The reaction media became colorless upon stirring at 25° C. and after 1 hour the contents were diluted with ethyl acetate, washed with water, dried over sodium sulfate, filtered and then concentrated under reduced pressure to afford 1.26 g of the title compound as an orange oil which solidified upon storage. mp: 35-38° C., LC/MS (Method A) retention time=0.99 minutes, 316.3 (M+H).

$^1$H NMR (400 MHz, CDCl$_3$) δ ppm: 8.09 (d, 2H), 7.53 (d, 2H), 4.87 (s, 2H), 3.73 (s, 3H), 2.19 (m, 1H), 1.05 (m, 2H), 0.86 (m, 2H).

$^{19}$F NMR (400 MHz, CDCl$_3$) δ ppm: −65.33 (s).

Example 9a: This example illustrates the preparation of N,2-dimethoxy-N-[[4-[5-(trifluoromethyl)-1,2,4-oxadiazol-3-yl]phenyl]methyl]propanamide (Compound X.04 of Table X)

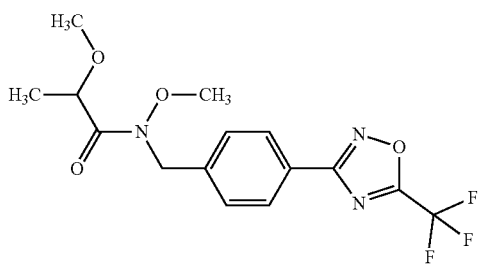

To a solution of 2-methoxypropanoic acid (0.2 g, 1.92 mmol) in DMF (7.7 mL) was added HATU (0.80 g, 2.11 mmol) and DIPEA (0.52 mL, 2.88 mmol). After the contents stirred for 20 minutes, N-methoxy-1-[4-[5-(trifluoromethyl)-1,2,4-oxadiazol-3-yl]phenyl]methanamine (0.524 g, 1.92 mmol) was introduced. After 2 hours, the contents were diluted with water and ethyl acetate, the layers were separated, and the aqueous phase was extracted with ethyl acetate. The total combined organic layer was dried over sodium sulfate and filtered. The solvent was removed under reduced pressure and the resultant crude residue was purified by flash chromatography over silica gel (cyclohexane/EtOAc eluent gradient 4:1 to 1:9) to afford 418 mg of the title compound as a white solid, mp: 62-65° C., LC/MS (Method A) retention time=1.02 minutes, 360.6 (M+H). A single enantiomeric form, i.e., (R)- or (S)-enantiomer, of 2-methoxypropanoic acid can be introduced, using identical conditions, to afford the corresponding single enantiomeric form of Compound X.04.

$^1$H NMR (400 MHz, CDCl$_3$) δ ppm: 8.09 (d, 2H), 7.48 (d, 2H), 4.98 (m, 1H), 4.80 (m, 1H), 4.27 (m, 1H), 3.71 (s, 3H), 3.34 (s, 3H), 1.37 (d, 3H).

$^{19}$F NMR (400 MHz, CDCl$_3$) δ ppm: −65.35 (s).

Example 9b: This example illustrates an alternative preparation of N,2-dimethoxy-N-[[4-[5-(trifluoromethyl)-1,2,4-oxadiazol-3-yl]phenyl]methyl]propanamide (Compound X.04 of Table X)

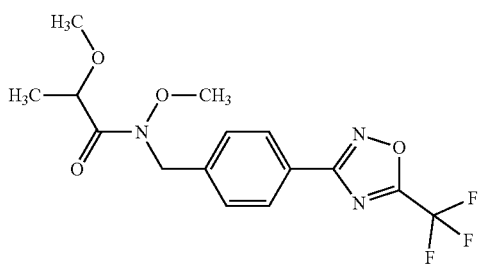

Step 1: Preparation of 2-methoxypropanoyl chloride

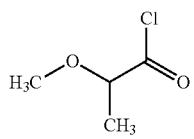

To a solution of 2-methoxypropanoic acid (0.70 g, 6.72 mmol), dimethylformamide (0.005 mL) and dichloromethane cooled via ice bath was introduced oxalyl chloride (0.90 mL, 10.1 mmol). After 30 minutes, the ice bath was removed and stirring continued for 3.5 hours. The contents were then concentrated under slightly reduced pressure (ca. 500 mbar) to afford 200 mg of the title compound that was used directly in the next transformation. A single enantiomeric form, i.e., (R)- or (S)-enantiomer, of 2-methoxypropanoic acid can be introduced, using identical conditions, to afford the corresponding single enantiomeric form of 2-methoxypropanoyl chloride.

Step 2: Preparation of 4-[(methoxyamino)methyl]benzonitrile hydrochloride

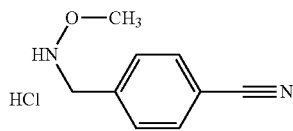

To a solution of 4-(bromomethyl)benzonitrile (2.0 g, 10.2 mmol) in acetonitrile (10 mL) was added O-methylhydroxylamine hydrochloride (1.7 g, 20.4 mmol) and potassium carbonate (3.0 g, 21.4 mmol). After 17 hours, the reaction mixture was poured into water and extracted with ethyl acetate. The total combined organic layer was washed with water and brine then dried over sodium sulfate, filtered, and concentrated under reduced pressure. The resultant crude residue was taken up in tert-butyl methyl ether (15 mL), cooled to via ice bath, and 4M HCl in dioxane (2.2 mL) was introduced dropwise. After 10 minutes, the ice bath was removed and the crude contents were stirred for 2 hours. After, all solids were collected via filtration, rinsed with tert-butyl methyl ether, and dried under vacuum to afford 1.6 g of the title compound as a white solid that was used in the next transformation without further purification.

$^1$H NMR (400 MHz, DMSO-d$_6$) δ ppm: 7.90 (d, 2H), 7.72 (d, 2H), 4.41 (s, 2H), 3.75 (s, 3H).

Step 3: Preparation of N-[(4-cyanophenyl)methyl]-N,2-dimethoxy-propanamide

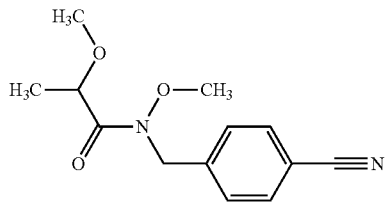

To a suspension of 4-[(methoxyamino)methyl]benzonitrile hydrochloride (0.33 g, 1.63 mmol) and sodium hydrogen carbonate (0.42 g, 4.90 mmol) in dichloromethane (25 mL) at cooled via ice bath was introduced dropwise 2-methoxypropanoyl chloride (0.20 g, 1.63 mmol) as a dichloromethane solution (10 mL). After 10 minutes, the ice bath was removed and the reaction mixture stirred for 15 minutes. After, the solids were removed via filtration and the filtrate solution was concentrated under reduced pressure. The resultant crude residue was purified by flash chromatography over silica gel (cyclohexane/EtOAc eluent gradient 99:1 to 1:1) to provide 155 mg of the title compound as a colorless oil. A single enantiomeric form, i.e., (R)- or (S)-enantiomer, of 2-methoxypropanoyl chloride can be introduced, using identical conditions, to afford the corresponding single enantiomeric form of N-[(4-cyanophenyl)methyl]-N,2-dimethoxy-propanamide.

$^1$H NMR (400 MHz, CDCl$_3$) δ ppm: 7.65 (d, 2H), 7.45 (d, 2H), 4.95 (m, 1H), 4.72 (m, 1H), 4.25 (q, 1H), 3.70 (s, 3H), 3.36 (s, 3H), 1.35 (d, 3H).

Step 4: Preparation of N-[[4-(N-hydroxycarbamimidoyl)phenyl]methyl]-N,2-dimethoxy-propanamide

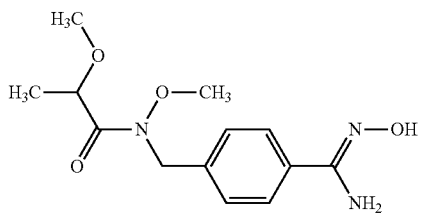

To a solution of N-[(4-cyanophenyl)methyl]-N,2-dimethoxy-propanamide (1.0 g, 4.03 mmol) and ethanol (5 mL) was introduced a 50% aqueous hydroxylamine solution (0.3 mL, 4.29 mmol). The reaction was heated at 60° C. for 3 hours, cooled to 25° C., and then concentrated under reduced pressure. The contents were basified to pH 8 with using an aqueous 30% NaOH solution, extracted with EtOAc, and the total combined organic phase was concentrated under reduced pressure then oven dried to afford 270 mg of the title compound as a white solid that was use in the next transformation without further purification. A single enantiomeric form, i.e., (R)- or (S)-enantiomer, of N-[(4-cyanophenyl)methyl]-N,2-dimethoxy-propanamide can be introduced, using identical conditions, to afford the corresponding single enantiomeric form of N-[[4-(N-hydroxycarbamimidoyl)phenyl]methyl]-N,2-dimethoxy-propanamide.

$^1$H NMR (400 MHz, DMSO-d$_6$) δ ppm: 9.59 (s, 1H), 7.63 (d, 2H), 7.25 (d, 2H), 5.77 (s, 2H), 4.88 (s, 1H), 4.71 (m, 1H), 4.25 (q, 1H), 3.69 (m, 3H), 3.21 (s, 3H), 1.20 (d, 3H).

Step 5: Preparation of N,2-dimethoxy-N-[[4-[5-(trifluoromethyl)-1,2,4-oxadiazol-3-yl]phenyl]methyl]propanamide To a 30 mL Schlenk tube connected to trap-1 (empty) followed by trap-2 (filled with an 4N NaOH aqueous solution) was added N-[[4-(N-hydroxycarbamimidoyl)phenyl]methyl]-N,2-dimethoxy-propanamide (1.0 g, 3.34 mmol), ethyl acetate (20 mL), and pyridine (0.41 mL, 5.0 mmol). The contents were stirred for 10 minutes and then cooled via ice bath. To the resultant white suspension was introduced 2,2,2-trifluoroacetyl chloride (0.49 g, 3.68 mmol) by gentle bubbling. The ice bath was removed and the reaction media became colorless solution upon stirring at room temperature. After 1 hour, the reaction contents were diluted with ethyl acetate, washed with water, dried over sodium sulfate, and concentrated under reduced pressure to afford 1.26 g of the title compound as white solid. mp: 62-65° C., LC/MS (Method A) retention time=1.02 minutes, 360.6 (M+H). A single enantiomeric form, i.e., (R)- or (S)-enantiomer, of N-[[4-(N-hydroxycarbamimidoyl)phenyl]methyl]-N,2-dimethoxy-propanamide can be introduced, using identical conditions, to afford the corresponding single enantiomeric form of Compound X.04.

$^1$H NMR (400 MHz, CDCl$_3$) δ ppm: 8.09 (d, 2H), 7.48 (d, 2H), 4.98 (m, 1H), 4.80 (m, 1H), 4.27 (m, 1H), 3.71 (s, 3H), 3.34 (s, 3H), 1.37 (d, 3H).

$^{19}$F NMR (400 MHz, CDCl$_3$) δ ppm: −65.35 (s).

Example 10a: This example illustrates the preparation of 1-methoxy-3-methyl-1-[[4-[5-(trifluoromethyl)-1,2,4-oxadiazol-3-yl]phenyl]methyl]urea (Compound X.14 of Table X)

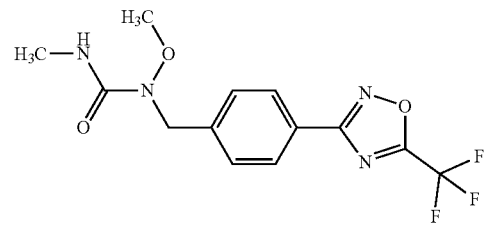

To a solution of N-methoxy-1-[4-[5-(trifluoromethyl)-1,2,4-oxadiazol-3-yl]phenyl]methanamine (0.10 g, 0.37 mmol) in dichloromethane (1.23 mL) was added N-methylcarbamoyl chloride (0.07 g, 0.73 mmol) and triethylamine (0.10 mL, 0.73 mmol). After 1 hour, the reaction mixture was concentrated under reduced pressure and the resultant crude residue was purified by flash chromatography over silica gel (cyclohexane/EtOAc eluent gradient 99:1 to 1:1) to provide 79 mg of the title compound as a white solid, mp: 75-78° C. LC/MS (Method A) retention time=0.96 minutes, (M+H) not observed.

$^1$H NMR (400 MHz, CDCl$_3$) δ ppm: 8.00 (d, 2H), 7.45 (d, 2H), 5.72 (m, 1H), 4.61 (s, 2H), 3.50 (s, 3H), 2.79 (d, 3H).

Example 10b: This example illustrates an alternative preparation of 1-methoxy-3-methyl-1-[[4-[5-(trifluoromethyl)-1,2,4-oxadiazol-3-yl]phenyl]methyl]urea (Compound X.14 of Table X)

Step 1: Preparation of 1-methoxy-3-methyl-urea

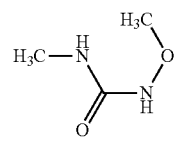

A 250 mL reactor equipped with mechanical stirrer and a condenser charged with water (10 mL), N-methoxyamine hydrochloride (9.0 g, 106.9 mmol), and sodium bicarbonate (20.0 g, 253.3 mmol), cooled via an ice bath, was stirred with cooling via ice bath for 15 minutes. Then, N-methyl carbamoyl chloride (10.0 g, 106.9 mmol) was introduced dropwise as a solution in EtOAc (15 mL) over 1 hour, keeping the temperature between 0° C. to 10° C. The contents were stirred an additional 2 hours at 0° C., then the ice bath was removed. After 4 hours, THF (25 mL) and EtOAc (10 mL) were added to the reaction mixture. After 15 minutes, stirring was stopped and the phases were allowed to separate. The organic layer was concentrated under reduced pressure to give a crude solid that was dried under vacuum. To the reactor was introduced a EtOAc/THF solution (1:1, 40 mL) and the contents stirred for 15 minutes. The solution was then concentrated under reduced pressure and the resultant crude solid was dried under vacuum. The two crude solid fractions were combined and triturated using pentane (50 mL), filtered, and dried under vacuum to afford 10.8 g of the title compound as a white solid that was used in the next transformation without further purification.

$^1$H NMR (400 MHz, DMSO-d6) δ ppm: 9.00 (s, 1H), 6.78 (sbr, 1H), 3.50 (s, 3H), 2.61 (m, 3H).

Step 2: Preparation of 1-[(4-cyanophenyl)methyl]-1-methoxy-3-methyl-urea

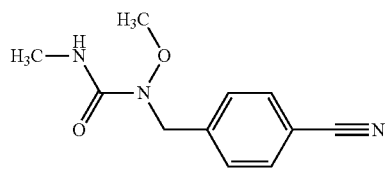

To a solution of 1-methoxy-3-methyl-urea (765 mg, 7.26 mmol), 4-(chloromethyl)benzonitrile (1.0 g, 6.60 mmol), tetrabutylammonium sulfate (0.113 g, 0.33 mmol), and acetonitrile (10 mL) was added potassium carbonate (1.02 g, 7.26 mmol). The contents were heated at 80° C. for 4 hours, cooled to 25° C., and the solids were removed via filtration, rinsed with EtOAc, and the filtrate was concentrated under reduced pressure. The resultant crude residue was dissolved in EtOAc (50 mL), washed sequentially with an aqueous 1N NaOH solution, water, and brine then dried with sodium sulfate and concentrated under reduced pressure to afford 1.4 g of the title compound as a yellow crystalline solid that was used in the next transformation without further purification.

$^1$H NMR (400 MHz, CDCl$_3$) δ ppm: 7.61 (d, 2H), 7.47 (d, 2H), 5.74 (brs, 1H), 4.67 (s, 2H), 3.54 (s, 3H), 2.82 (s, 3H).

Step 3: Preparation of 1-[[4-(N-hydroxycarbamimidoyl)phenyl]methyl]-1-methoxy-3-methyl-urea

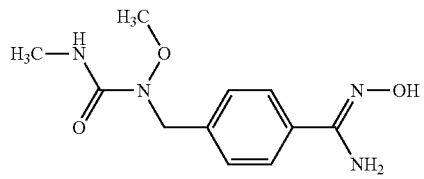

To a solution of 1-[(4-cyanophenyl)methyl]-1-methoxy-3-methyl-urea (1.00 g, 4.56 mmol) and ethanol (5 mL) was added hydroxylamine hydrochloride (0.380 g, 5.47 mmol) followed by the dropwise introduction of triethylamine (0.77 mL, 5.47 mmol). The reaction media was heated at 80° C. for 2 hours, cooled to 25° C., and then concentrated under reduced pressure. The reaction contents were basified to pH 8 with using an aqueous 30% NaOH solution, extracted with EtOAc, and the total combined organic phase was concentrated under reduced pressure then oven dried to afford 970 mg of the title compound as a yellow solid.

$^1$H NMR (400 MHz, DMSO-d6) δ ppm: 7.60 (d, 2H), 7.25 (d, 2H), 7.12 (m, 1H), 5.75 (s, 2H), 4.50 (s, 3H), 3.50 (s, 3H), 2.50 (d, 3H).

Step 4: Preparation of 1-methoxy-3-methyl-1-[[4-[5-(trifluoromethyl)-1,2,4-oxadiazol-3-yl]phenyl]methyl]urea A 30 mL Schlenk tube, connected to trap-1 (empty) followed by trap-2 (filled with an 4N NaOH aqueous solution), was charged with 1-[[4-(N-hydroxycarbamimidoyl)phenyl]methyl]-1-methoxy-3-methyl-urea (1.00 g, 3.75 mmol), ethyl acetate (20 mL), and pyridine (0.46 mL, 5.62 mmol). After 10 minutes, to the resultant white suspension was introduced 2,2,2-trifluoroacetyl fluoride (0.57 g, 4.12 mmol) by gentle bubbling. The reaction media became colorless and after 4.5 hours the reaction contents were diluted with ethyl acetate, washed with water, dried over sodium sulfate, and concentrated under reduced pressure to afford 1.21 g of the title compound as a white solid, mp: 75-78° C. LC/MS (Method A) retention time=0.96 minutes, (M+H) not observed.

$^1$H NMR (400 MHz, CDCl$_3$) δ ppm: 8.00 (d, 2H), 7.45 (d, 2H), 5.72 (m, 1H), 4.61 (s, 2H), 3.50 (s, 3H), 2.79 (d, 3H).

Example 11: This example illustrates an alternative preparation 3-ethyl-1-methoxy-1-[[4-[5-(trifluoromethyl)-1,2,4-oxadiazol-3-yl]phenyl]methyl]urea (Compound X.25 of Table X)

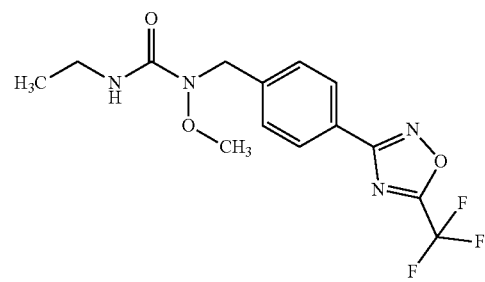

Triphosgene (130 mg) was dissolved in 1,2-dichloroethane (5 mL) and cooled via ice bath. To this colorless solution was added N-methoxy-1-[4-[5-(trifluoromethyl)-1,2,4-oxadiazol-3-yl]phenyl]methanamine (300 mg) dissolved in 1,2-dichloroethane (2.5 mL) and triethylamine (0.38 mL). After 1 hour, a solution of ethylamine hydrochloride (179 mg) dissolved in 1,2-dichloroethane (2.5 mL) was introduced to the reaction mixture followed by triethylamine (0.38 mL) and the mixture stirred for 24 hours. Then sodium hydrogen carbonate and dichloromethane were added to the mixture and the aqueous layer was extracted twice with dichloromethane. The total combined organic layer was washed with brine, dried over sodium sulfate, filtered, and concentrated under reduced pressure. The crude residue was purified by flash chromatography on silica gel using a cyclohexane/ethyl acetate eluent gradient to afford 0.084 g of the title compound as a white solid. mp: 58-63° C. LC/MS (Method A) retention time=1.02 minutes, 345 (M+H).

¹H NMR (400 MHz, CDCl₃) δ ppm: 8.12 (d, 2H), 7.50 (d, 2H), 5.85 (m, 1H), 4.7 (s, 2H), 3.60 (s, 3H), 3.35 (m, 2H), 1.15 (t, 3H)

Example 12: This example illustrates an alternative preparation of 1,3-dimethoxy-1-[[4-[5(trifluoromethyl)-1,2,4-oxadiazol-3-yl]phenyl]methyl]urea (Compound X.24 of Table X)

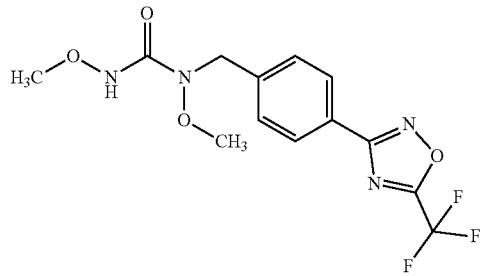

N-methoxy-1-[4-[5-(trifluoromethyl)-1,2,4-oxadiazol-3-yl]phenyl]methanamine (140 mg) was dissolved in tetrahydrofuran (1.54 mL) and to this suspension was introduced CDI (111 mg) in one portion. The suspension slowly turned into a clear solution as the mixture was stirred for 1.5 hours at ambient temperature. Then O-methylhydroxylamine hydrochloride (131 mg) was added followed by triethylamine (0.21 mL). After 24 hours, the reaction contents were concentrated under reduced pressure and the crude residue was purified by flash chromatography on silica gel using a cyclohexane/ethyl acetate gradient to afford 0.14 g of the title compound as a white solid. mp: 88-91° C. LC/MS (Method A) retention time=0.95 minutes, 347 (M+H).

¹H NMR (400 MHz, CDCl₃) δ ppm: 8.32 (s, 1H), 8.12 (d, 2H), 7.50 (d, 2H), 4.72 (s, 2H), 3.80 (s, 3H), 3.60 (s, 3H).

The following procedure was used in a combinatorial fashion to provide the compounds of Formula (I), wherein Z represents —R⁴, using appropriate building blocks (compounds (II) and (III)). The compounds prepared via the following combinatorial protocol were analyzed using LC/MS Method B.

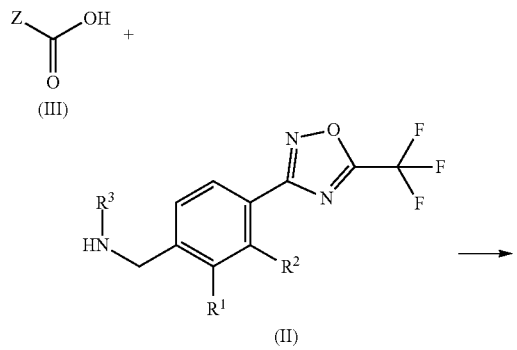

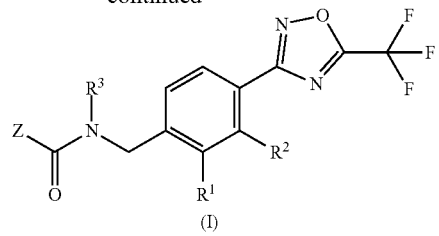

By way of exemplification, acid derivatives of formula (III) (0.038 mmol in DMA (375 μL) were transferred to a 96 slot deep well plate (DWP96) containing the [4-[5-(trifluoromethyl)-1,2,4-oxadiazol-3-yl]aryl]methanamine derivative of formula (II) (0.03 mmol) and DIPEA (0.09 mmol) in DMA (250 μL), followed by the addition of BOP-Cl (0.06 mmol) dissolved in DMA (250 μL). The DWP was sealed and stirred at 50° C. for 18 hours. The solvent was removed under a stream of nitrogen. The resultant crude residues were solubilized in a mixture of MeOH (250 μL) and DMA (500 μL) and directly submitted for preparative LC/MS purification which provided the compounds of formula (I) in 10-85% yields.

Alternatively, the following procedures (protocol A and protocol B) were used in a combinatorial fashion to provide the compounds of Formula (I), wherein Z represents —NR⁶R⁷, using appropriate building blocks (compounds (II) and (IV)). The compounds prepared via the following combinatorial protocols were analyzed using LC/MS Method B.

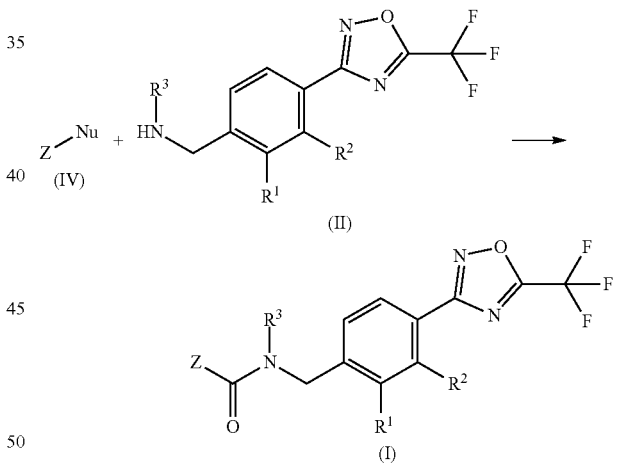

Protocol A: Portions of triphosgene (6 mg) in DCE (0.3 mL) were transferred at 0° C. to a 96 slot deep well plate (DWP96) containing compounds of formula (IV) (0.05 mmol), wherein Z-Nu is an amine derivative [HNR⁶R⁷], and triethylamine (0.12 mmol) in DMA (200 μL). The reaction mixtures were stirred at room temperature for 30 minutes. Then, [4-[5-(trifluoromethyl)-1,2,4-oxadiazol-3-yl]aryl] methanamine derivatives of formula (II) (0.05 mmol) and triethylamine (0.12 mmol) in DMA (200 μL) were added. The DWP was sealed and stirred at room temperature for 18 hours. DCE was removed under the Barkey station. The crude residues were solubilized in a mixture of MeOH (200 μL) and DMA (600 μL) and directly submitted for preparative LC/MS purification which provided the compounds of formula (I) in 3-45% yields.

Protocol B: The amine derivative [HNR⁶R⁷] of formula (IV) (0.05 mmol) and DIPEA (0.25 mmol) in DMA (300 μL) were transferred at room temperature to a 96 slot deep well plate (DWP96). CDI (0.10 mmol) in DMA (300 μL) were added and the contents stirred until solubilization. [4-[5-(trifluoromethyl)-1,2,4-oxadiazol-3-yl]aryl]methanamine derivatives of formula (II) (0.05 mmol) and triethylamine (0.12 mmol) in DMA (200 μL) were then introduced. The DWP was sealed and stirred at room temperature for 18 hours. The DCE was removed under the Barkey station. The crude residues were solubilized in a mixture of MeOH (200 μL) and DMA (600 μL) and directly submitted for preparative LC/MS purification which provided the compounds of formula (I) in 5-47% yields.

Where necessary, enantiomerically pure final compounds may be obtained from racemic materials as appropriate via standard physical separation techniques, such as reverse phase chiral chromatography, or through stereoselective synthetic techniques, (eg, by using chiral starting materials).

TABLE T1

Melting point (mp) data and/or retention times ($R_t$) for compounds X.01 to X.25 according to Formula (I):

| Entry | Compound name | Structure | RT (min) | [M + H] (measured) | Method | mp ° C. |
|---|---|---|---|---|---|---|
| X.01 | N-methoxy-N-[[4-[5-(trifluoromethyl)-1,2,4-oxadiazol-3-yl]phenyl]methyl] cyclopropanecarboxamide | 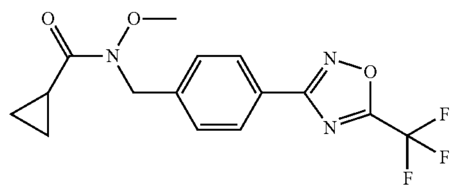 | 0.99 | 316.3 | A | 38-41 |
| X.02 | N-methoxy-N-[[4-[5-(trifluoromethyl)-1,2,4-oxadiazol-3-yl]phenyl]methyl] pent-4-ynamide | 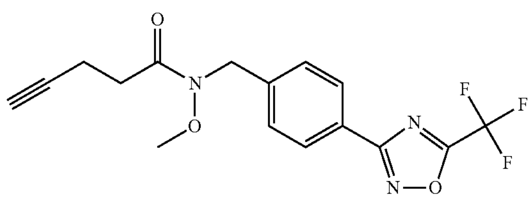 | 1.73 | 354.2 | B | |
| X.03 | N-methoxy-2-methyl-N-[[4-[5-(trifluoromethyl)-1,2,4-oxadiazol-3-yl]phenyl]methyl] prop-2-enamide | 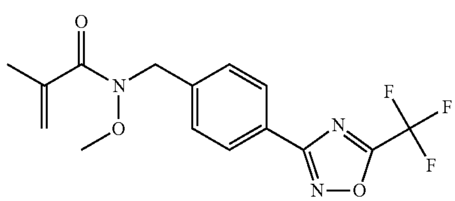 | 1.74 | 342.2 | B | |
| X.04 | N,2-dimethoxy-N-[[4-[5-(trifluoromethyl)-1,2,4-oxadiazol-3-yl]phenyl]methyl] propanamide | 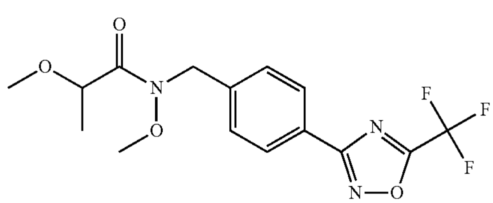 | 1.62 | 360.2 | B | 62-65 |
| X.05 | N-cyclopropyl-3,3,3-trifluoro-N-[[4-[5-(trifluoromethyl)-1,2,4-oxadiazol-3-yl]phenyl]methyl] propanamide | 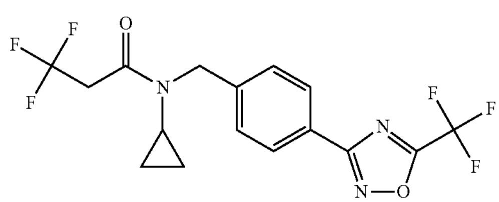 | 1.84 | 394.2 | B | |
| X.06 | 2,2-difluoro-N-(2-methoxyethyl)-N-[[4-[5-(trifluoromethyl)-1,2,4-oxadiazol-3-yl]phenyl]methyl] cyclopropanecarboxamide | 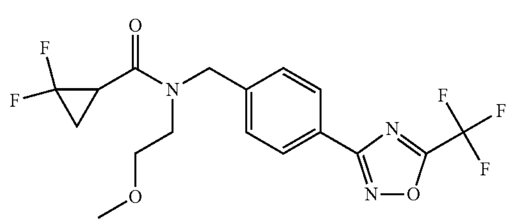 | 1.73 | 406.3 | B | |

TABLE T1-continued

Melting point (mp) data and/or retention times (R_t) for compounds X.01 to X.25 according to Formula (I):

| Entry | Compound name | Structure | RT (min) | [M + H] (measured) | Method | mp ° C. |
|---|---|---|---|---|---|---|
| X.07 | N-ethyl-2-methyl-N-[[4-[5-(trifluoromethyl)-1,2,4-oxadiazol-3-yl]phenyl]methyl] propanamide | 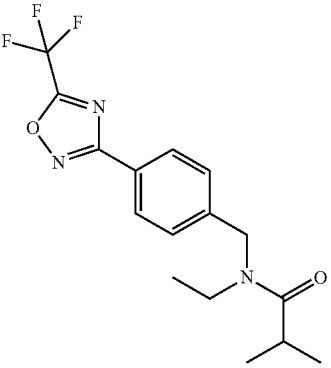 | 1.78 | 342.3 | B | |
| X.08 | N-[[3-fluoro-4-[5-(trifluoromethyl)-1,2,4-oxadiazol-3-yl]phenyl]methyl]-N-methoxy-propanamide | 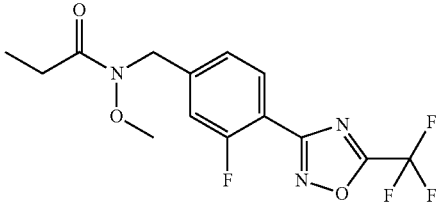 | 1.05 | 348 | A | |
| X.09 | 2-methoxy-N-(2,2,2-trifluoroethyl)-N-[[4-[5-(trifluoromethyl)-1,2,4-oxadiazol-3-yl]phenyl]methyl] acetamide | 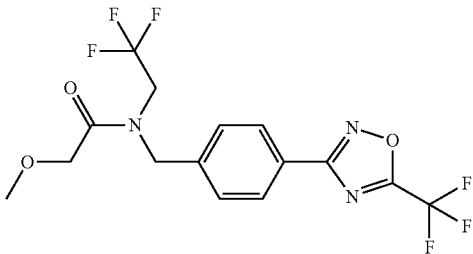 | | | | 92.6-94.3 |
| X.10 | N-[[2,3-difluoro-4-[5-(trifluoromethyl)-1,2,4-oxadiazol-3-yl]phenyl]methyl]-N-methoxy-cyclopropanecarboxamide | 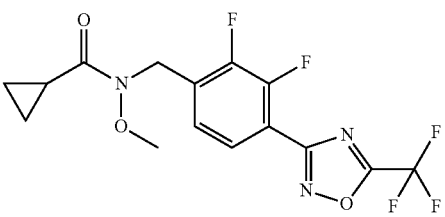 | 1.11 | 378 | A | |
| X.11 | 2-(difluoromethoxy)-N-methyl-N-[[4-[5-(trifluoromethyl)-1,2,4-oxadiazol-3-yl]phenyl]methyl] acetamide | 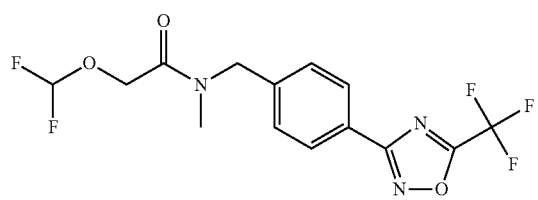 | 1.02 | 366 | A | |

TABLE T1-continued

Melting point (mp) data and/or retention times (R$_t$) for compounds X.01 to X.25 according to Formula (I):

| Entry | Compound name | Structure | RT (min) | [M + H] (measured) | Method | mp ° C. |
|---|---|---|---|---|---|---|
| X.12 | N-ethoxy-2-methoxy-N-[[4-[5-(trifluoromethyl)-1,2,4-oxadiazol-3-yl]phenyl]methyl]propanamide | 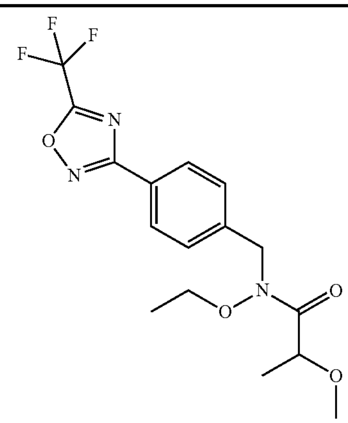 | 1.67 | 374.17 | B | |
| X.13 | N-isopropyl-N-[[4-[5-(trifluoromethyl)-1,2,4-oxadiazol-3-yl]phenyl]methyl]tetrahydrofuran-2-carboxamide | 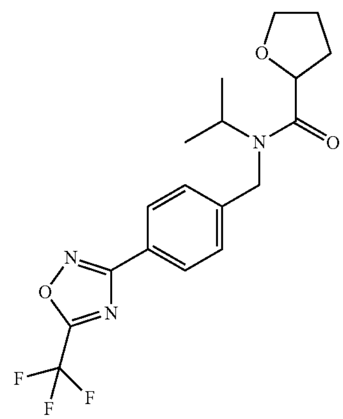 | 1.67 | 374.17 | B | |
| X.14 | 1-methoxy-3-methyl-1-[[4-[5-(trifluoromethyl)-1,2,4-oxadiazol-3-yl]phenyl]methyl]urea | 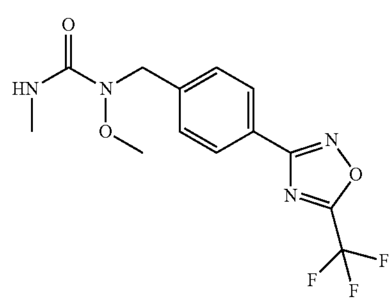 | | | | 75-78 |
| X.15 | 3-cyclopropyl-1-methoxy-1-[[4-[5-(trifluoromethyl)-1,2,4-oxadiazol-3-yl]phenyl]methyl]urea | 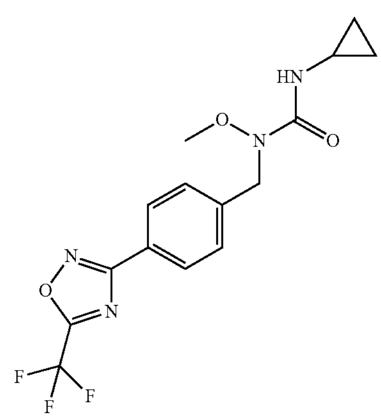 | | | | 84-87 |

TABLE T1-continued

Melting point (mp) data and/or retention times (R_t) for compounds X.01 to X.25 according to Formula (I):

| Entry | Compound name | Structure | RT (min) | [M + H] (measured) | Method | mp ° C. |
|---|---|---|---|---|---|---|
| X.16 | 3-ethoxy-1-methoxy-1-[[4-[5-(trifluoromethyl)-1,2,4-oxadiazol-3-yl]phenyl]methyl]urea | 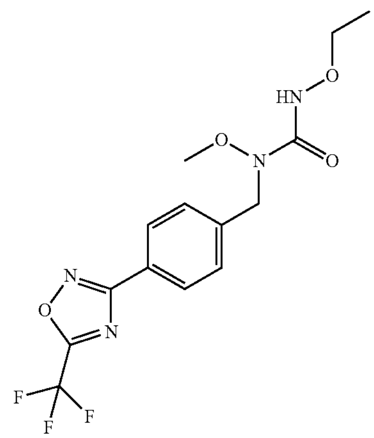 | | | | 107-110 |
| X.17 | 3-allyl-1-methoxy-1-[[4-[5-(trifluoromethyl)-1,2,4-oxadiazol-3-yl]phenyl]methyl]urea | 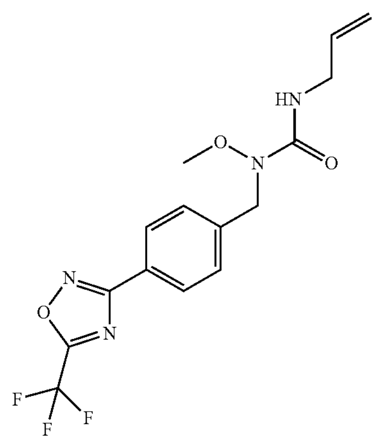 | | | | 64-70 |
| X.18 | 1-cyclopropyl-3-methoxy-3-methyl-1-[[4-[5-(trifluoromethyl)-1,2,4-oxadiazol-3-yl]phenyl]methyl]urea | 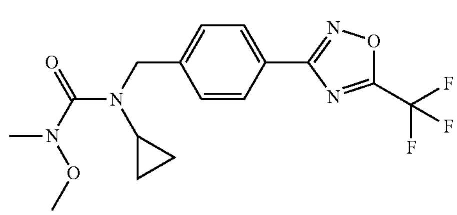 | 1.1 | 371 | A | |
| X.19 | 3-isopropyl-1-methoxy-1-[[4-[5-(trifluoromethyl)-1,2,4-oxadiazol-3-yl]phenyl]methyl]urea | 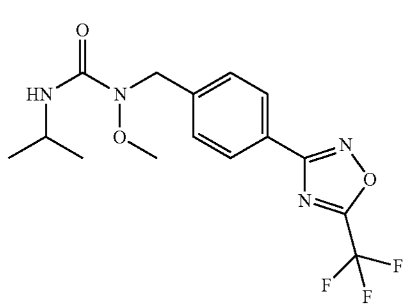 | | | | 106-107.3 |

TABLE T1-continued

Melting point (mp) data and/or retention times ($R_t$) for compounds X.01 to X.25 according to Formula (I):

| Entry | Compound name | Structure | RT (min) | [M + H] (measured) | Method | mp ° C. |
|---|---|---|---|---|---|---|
| X.20 | 1-methoxy-3-prop-2-ynyl-1-[[4-[5-(trifluoromethyl)-1,2,4-oxadiazol-3-yl]phenyl]methyl]urea | 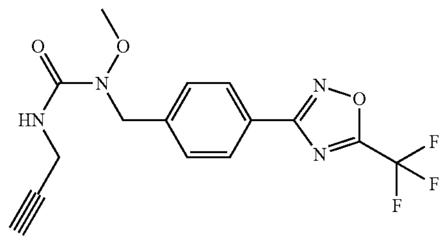 | | | | 88.9-90.6 |
| X.21 | 1-[[3-fluoro-4-[5-(trifluoromethyl)-1,2,4-oxadiazol-3-yl]phenyl]methyl]-1-methoxy-3-methyl-urea | 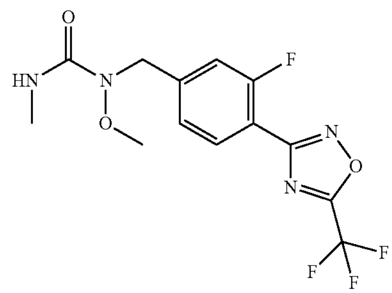 | 0.98 | 349 | A | |
| X.22 | 3-(cyclopropylmethyl)-1-methyl-1-[[4-[5-(trifluoromethyl)-1,2,4-oxadiazol-3-yl]phenyl]methyl]urea | 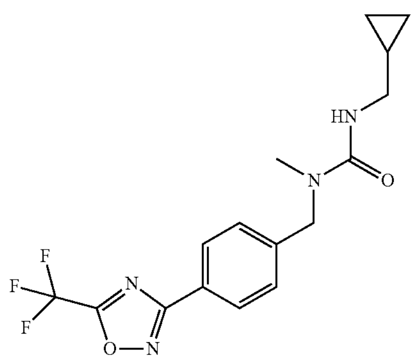 | 1.63 | 355.2 | B | |
| X.23 | 1-ethyl-3-(2,2,2-trifluoroethyl)-1-(trifluoromethyl)-1,2,4-oxadiazol-3-yl]phenyl]methyl]urea | 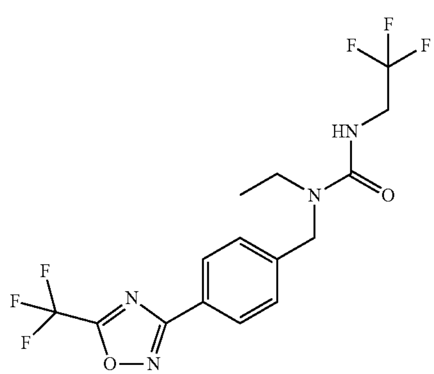 | 1.7 | 397.2 | B | |

TABLE T1-continued

Melting point (mp) data and/or retention times ($R_t$) for compounds X.01 to X.25 according to Formula (I):

| Entry | Compound name | Structure | RT (min) | [M + H] (measured) | Method | mp ° C. |
|---|---|---|---|---|---|---|
| X.24 | 1,3-dimethoxy-1-[[4-[5-(trifluoromethyl)-1,2,4-oxadiazol-3-yl]phenyl]methyl]urea | 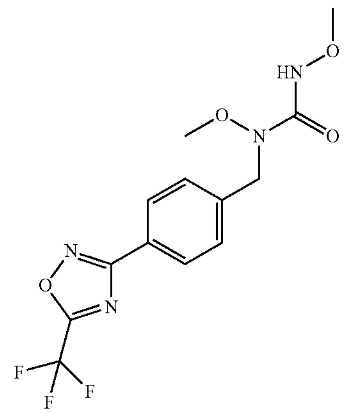 | | | | 88-91 |
| X.25 | 3-ethyl-1-methoxy-1-[[4-[5-(trifluoromethyl)-1,2,4-oxadiazol-3-yl]phenyl]methyl]urea | 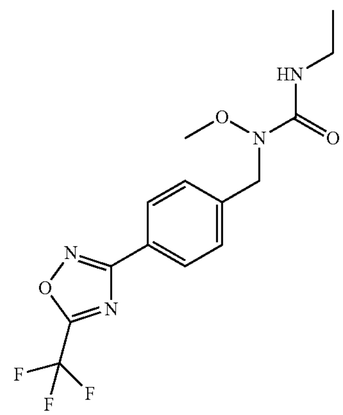 | | | | 58-63 |

BIOLOGICAL EXAMPLES

General Examples of Leaf Disk Tests in Well Plates:

Leaf disks or leaf segments of various plant species are cut from plants grown in a greenhouse. The cut leaf disks or segments are placed in multiwell plates (24-well format) onto water agar. The leaf disks are sprayed with a test solution before (preventative) or after (curative) inoculation. Compounds to be tested are prepared as DMSO solutions (max. 10 mg/ml) which are diluted to the appropriate concentration with 0.025% Tween20 just before spraying. The inoculated leaf disks or segments are incubated under defined conditions (temperature, relative humidity, light, etc.) according to the respective test system. A single evaluation of disease level is carried out 3 to 14 days after inoculation, depending on the pathosystem. Percent disease control relative to the untreated check leaf disks or segments is then calculated.

General Examples of Liquid Culture Tests in Well Plates:

Mycelia fragments or conidia suspensions of a fungus prepared either freshly from liquid cultures of the fungus or from cryogenic storage, are directly mixed into nutrient broth. DMSO solutions of the test compound (max. 10 mg/ml) are diluted with 0.025% Tween20 by a factor of 50 and 10 µl of this solution is pipetted into a microtiter plate (96-well format). The nutrient broth containing the fungal spores/mycelia fragments is then added to give an end concentration of the tested compound. The test plates are incubated in the dark at 24° C. and 96% relative humidity. The inhibition of fungal growth is determined photometrically after 2 to 7 days, depending on the pathosystem, and percent antifungal activity relative to the untreated check is calculated.

Example A1: Fungicidal Activity Against *Puccinia Recondita* f. sp. *Tritici*/Wheat/Leaf Disc Preventative (Brown Rust)

Wheat leaf segments cv. Kanzler were placed on agar in multiwell plates (24-well format) and sprayed with the formulated test compound diluted in water. The leaf disks were inoculated with a spore suspension of the fungus 1 day after application. The inoculated leaf segments were incubated at 19° C. and 75% relative humidity (rh) under a light regime of 12 hours light/12 hours darkness in a climate cabinet and the activity of a compound was assessed as percent disease control compared to untreated when an appropriate level of disease damage appears in untreated check leaf segments (7 to 9 days after application).

The following compounds at 200 ppm in the applied formulation give at least 80% disease control in this test when compared to untreated control leaf disks under the same conditions, which show extensive disease development.

Compounds (from Table T1) X.01, X.02, X.03, X.04, X.05, X.06, X.07, X.08, X.09, X.10, X.11, X.12, and X.13, X.14, X.15, X.16, X.17, X.18, X.19, X.20, X.21, X.22, X.23, X.24, and X.25.

Example A2: Fungicidal Activity Against *Puccinia Recondite* f. sp. *Tritici*/Wheat/Leaf Disc Curative (Brown Rust)

Wheat leaf segments cv. Kanzler are placed on agar in multiwell plates (24-well format). The leaf segments are then inoculated with a spore suspension of the fungus. Plates were stored in darkness at 19° C. and 75% relative humidity. The formulated test compound diluted in water was applied 1 day after inoculation. The leaf segments were incubated at 19° C. and 75% relative humidity under a light regime of 12 hours light/12 hours darkness in a climate cabinet and the activity of a compound was assessed as percent disease control compared to untreated when an appropriate level of disease damage appears in untreated check leaf segments (6 to 8 days after application).

The following compounds at 200 ppm in the applied formulation give at least 80% disease control in this test when compared to untreated control leaf disks under the same conditions, which show extensive disease development.

Compounds (from Table T1) X.01, X.02, X.03, X.04, X.05, X.06, X.07, X.08, X.09, X.10, X.11, X.12, and X.13, X.14, X.15, X.16, X.17, X.18, X.19, X.20, X.21, X.22, X.23, X.24, and X.25.

Example A3: Fungicidal Activity Against *Phakopsora Pachyrhizi*/Soybean/Leaf Disc Preventative (Asian Soybean Rust)

Soybean leaf disks are placed on water agar in multiwell plates (24-well format) and sprayed with the formulated test compound diluted in water. One day after application leaf discs are inoculated by spraying a spore suspension on the lower leaf surface. After an incubation period in a climate cabinet of 24-36 hours in darkness at 20° C. and 75% rh leaf disc are kept at 20° C. with 12 h light/day and 75% rh. The activity of a compound is assessed as percent disease control compared to untreated when an appropriate level of disease damage appears in untreated check leaf disks (12 to 14 days after application).

The following compounds at 200 ppm in the applied formulation give at least 80% disease control in this test when compared to untreated control leaf disks under the same conditions, which show extensive disease development.

Compounds (from Table T1) X.01, X.02, X.03, X.04, X.05, X.06, X.07, X.08, X.09, X.10, X.11, X.12, and X.13, X.14, X.15, X.16, X.17, X.18, X.19, X.20, X.21, X.22, X.23, X.24, and X.25.

Example A4: Fungicidal Activity Against *Glomerella Lagenarium* (*Colletotrichum Lagenarium*) Liquid Culture/Cucumber/Preventative (Anthracnose)

Conidia of the fungus from cryogenic storage are directly mixed into nutrient broth (PDB—potato dextrose broth). After placing a (DMSO) solution of test compound into a microtiter plate (96-well format), the nutrient broth containing the fungal spores is added. The test plates are incubated at 24° C. and the inhibition of growth is measured photometrically 3 to 4 days after application.

The following compounds at 20 ppm in the applied formulation give at least 80% disease control in this test when compared to untreated control under the same conditions, which show extensive disease development.

Compounds (from Table T1) X.01, X.02, X.03, X.04, X.05, X.06, X.07, X.08, X.09, X.10, X.11, X.12, and X.13, X.14, X.15, X.16, X.17, X.18, X.19, X.20, X.21, X.22, X.23, X.24, and X.25.

Further biolgical test examples relating to fungicidal composition comprising a mixture of components (A) and (B) as active ingredients:

Example B1: Preventative Activity Against *Phakopsora Pachyrhizi* on Soybean 4-week old soybean plants are sprayed in a spray chamber with a tank-mix of formulated test compounds (WP10) diluted in water. Leaf disks are cut from treated plants and placed on agar into 24-well plates one day after application. Leaf disks are inoculated by spraying them with a spore suspension on their lower leaf surface. After an incubation period in a climate cabinet of 24-36 hours in darkness at 20° C. and 75% rh, the leaf disks are then kept at 20° C. with 12 h light/day and 75% rh. The percentage leaf disk area covered by disease is assessed when an appropriate level of disease appears on untreated check plants (10-14 days after application).

The following mixture compositions (A:B) at the reported concentration (in ppm) gave at least 80% disease control in this test.

| Component A (Compound) | Component B | Ratio A:B | Conc. (ppm) (A:B) |
|---|---|---|---|
| X.01 | Benzovindiflupyr | 1:3 | 40:120 |
| X.01 | Benzovindiflupyr | 1:1 | 40:40 |
| X.01 | Benzovindiflupyr | 1:1 | 120:120 |
| X.01 | Benzovindiflupyr | 3:1 | 120:40 |
| X.14 | Benzovindiflupyr | 1:3 | 40:120 |
| X.14 | Benzovindiflupyr | 1:2 | 10:20 |
| X.14 | Benzovindiflupyr | 1:1 | 20:20 |
| X.14 | Benzovindiflupyr | 1:1 | 120:120 |
| X.14 | Benzovindiflupyr | 3:1 | 120:40 |
| X.04 | Benzovindiflupyr | 1:1 | 9:9 |
| X.04 | Benzovindiflupyr | 2:1 | 9:4.5 |
| X.04 | Benzovindiflupyr | 1:3 | 3:9 |
| X.07 | Benzovindiflupyr | 1:1 | 9:9 |
| X.07 | Benzovindiflupyr | 2:1 | 9:4.5 |
| X.07 | Benzovindiflupyr | 1:3 | 3:9 |
| X.07 | Benzovindiflupyr | 1:1.5 | 3:4.5 |
| X.25 | Benzovindiflupyr | 1:1 | 9:9 |
| X.25 | Benzovindiflupyr | 2:1 | 9:4.5 |
| X.25 | Benzovindiflupyr | 1:3 | 3:9 |
| X.25 | Benzovindiflupyr | 1:1.5 | 3:4.5 |
| X.24 | Benzovindiflupyr | 1:1 | 9:9 |
| X.24 | Benzovindiflupyr | 2:1 | 9:4.5 |
| X.24 | Benzovindiflupyr | 1:3 | 3:9 |
| X.24 | Benzovindiflupyr | 1:1.5 | 3:4.5 |
| X.01 | Fluxapyroxad | 1:3 | 40:120 |
| X.01 | Fluxapyroxad | 1:1 | 40:40 |
| X.01 | Fluxapyroxad | 1:1 | 120:120 |
| X.01 | Fluxapyroxad | 3:1 | 120:40 |
| X.14 | Fluxapyroxad | 1:3 | 40:120 |
| X.14 | Fluxapyroxad | 1:1 | 120:120 |
| X.14 | Fluxapyroxad | 3:1 | 120:40 |
| X.04 | Fluxapyroxad | 1:1 | 9:9 |
| X.04 | Fluxapyroxad | 2:1 | 9:4.5 |
| X.04 | Fluxapyroxad | 1:1.5 | 3:4.5 |
| X.07 | Fluxapyroxad | 1:1 | 9:9 |
| X.07 | Fluxapyroxad | 2:1 | 9:4.5 |
| X.07 | Fluxapyroxad | 1:1.5 | 3:4.5 |

| Component A (Compound) | Component B | Ratio A:B | Conc. (ppm) (A:B) |
|---|---|---|---|
| X.25 | Fluxapyroxad | 1:1 | 9:9 |
| X.25 | Fluxapyroxad | 2:1 | 9:4.5 |
| X.25 | Fluxapyroxad | 1:3 | 3:9 |
| X.25 | Fluxapyroxad | 1:1.5 | 3:4.5 |
| X.24 | Fluxapyroxad | 1:1 | 9:9 |
| X.24 | Fluxapyroxad | 2:1 | 9:4.5 |
| X.24 | Fluxapyroxad | 1:3 | 3:9 |
| X.24 | Fluxapyroxad | 1:1.5 | 3:4.5 |
| X.01 | Pydiflumetofen | 1:5 | 120:600 |
| X.01 | Pydiflumetofen | 1:3 | 120:300 |
| X.14 | Pydiflumetofen | 1:15 | 40:600 |
| X.14 | Pydiflumetofen | 1:7.5 | 40:300 |
| X.14 | Pydiflumetofen | 1:5 | 120:600 |
| X.14 | Pydiflumetofen | 1:3 | 120:300 |
| X.04 | Pydiflumetofen | 1:6.67 | 9:60 |
| X.04 | Pydiflumetofen | 3:1 | 9:3 |
| X.04 | Pydiflumetofen | 1:20 | 3:60 |
| X.04 | Pydiflumetofen | 1:1 | 3:3 |
| X.07 | Pydiflumetofen | 1:6.67 | 9:60 |
| X.07 | Pydiflumetofen | 3:1 | 9:3 |
| X.07 | Pydiflumetofen | 1:20 | 3:60 |
| X.07 | Pydiflumetofen | 1:1 | 3:3 |
| X.25 | Pydiflumetofen | 1:6.67 | 9:60 |
| X.25 | Pydiflumetofen | 3:1 | 9:3 |
| X.25 | Pydiflumetofen | 1:20 | 3:60 |
| X.25 | Pydiflumetofen | 1:1 | 3:3 |
| X.24 | Pydiflumetofen | 1:6.67 | 9:60 |
| X.24 | Pydiflumetofen | 3:1 | 9:3 |
| X.24 | Pydiflumetofen | 1:20 | 3:60 |
| X.24 | Pydiflumetofen | 1:1 | 3:3 |
| X.01 | Fluopyram | 1:15 | 120:600 |
| X.01 | Fluopyram | 1:7.5 | 120:300 |
| X.14 | Fluopyram | 1:15 | 40:600 |
| X.14 | Fluopyram | 1:7.5 | 40:300 |
| X.14 | Fluopyram | 1:5 | 120:600 |
| X.14 | Fluopyram | 1:3 | 120:300 |
| X.04 | Fluopyram | 1:6.67 | 9:60 |
| X.04 | Fluopyram | 3:1 | 9:3 |
| X.04 | Fluopyram | 1:20 | 3:60 |
| X.04 | Fluopyram | 1:1 | 3:3 |
| X.07 | Fluopyram | 1:6.67 | 9:60 |
| X.07 | Fluopyram | 3:1 | 9:3 |
| X.07 | Fluopyram | 1:20 | 3:60 |
| X.07 | Fluopyram | 1:1 | 3:3 |
| X.25 | Fluopyram | 1:6.67 | 9:60 |
| X.25 | Fluopyram | 3:1 | 9:3 |
| X.25 | Fluopyram | 1:20 | 3:60 |
| X.25 | Fluopyram | 1:1 | 3:3 |
| X.24 | Fluopyram | 1:6.67 | 9:60 |
| X.24 | Fluopyram | 3:1 | 9:3 |
| X.24 | Fluopyram | 1:1 | 3:3 |
| X.01 | Penthiopyrad | 1:6 | 40:240 |
| X.01 | Penthiopyrad | 1:3 | 40:120 |
| X.01 | Penthiopyrad | 1:2 | 120:240 |
| X.01 | Penthiopyrad | 1:1 | 120:120 |
| X.14 | Penthiopyrad | 1:6 | 40:240 |
| X.14 | Penthiopyrad | 1:2 | 120:240 |
| X.14 | Penthiopyrad | 1:1 | 120:120 |
| X.04 | Penthiopyrad | 1:3.33 | 9:30 |
| X.04 | Penthiopyrad | 1:1.67 | 9:15 |
| X.04 | Penthiopyrad | 1:10 | 3:30 |
| X.04 | Penthiopyrad | 1:5 | 3:15 |
| X.07 | Penthiopyrad | 1:3.33 | 9:30 |
| X.07 | Penthiopyrad | 1:1.67 | 9:15 |
| X.07 | Penthiopyrad | 1:10 | 3:30 |
| X.07 | Penthiopyrad | 1:5 | 3:15 |
| X.25 | Penthiopyrad | 1:3.33 | 9:30 |
| X.25 | Penthiopyrad | 1:1.67 | 9:15 |
| X.25 | Penthiopyrad | 1:10 | 3:30 |
| X.25 | Penthiopyrad | 1:5 | 3:15 |
| X.24 | Penthiopyrad | 1:3.33 | 9:30 |
| X.24 | Penthiopyrad | 1:1.67 | 9:15 |
| X.24 | Penthiopyrad | 1:10 | 3:30 |
| X.24 | Penthiopyrad | 1:5 | 3:15 |
| X.01 | Difenoconazole | 1:30 | 40:1200 |
| X.01 | Difenoconazole | 1:10 | 120:1200 |
| X.01 | Difenoconazole | 1:6 | 40:240 |
| X.01 | Difenoconazole | 1:2 | 120:240 |
| X.14 | Difenoconazole | 1:60 | 10:600 |
| X.14 | Difenoconazole | 1:30 | 40:1200 |
| X.14 | Difenoconazole | 1:30 | 10:300 |
| X.14 | Difenoconazole | 1:30 | 20:600 |
| X.14 | Difenoconazole | 1:15 | 20:300 |
| X.14 | Difenoconazole | 1:10 | 120:1200 |
| X.14 | Difenoconazole | 1:6 | 40:240 |
| X.14 | Difenoconazole | 1:2 | 120:240 |
| X.04 | Difenoconazole | 1:6.67 | 9:60 |
| X.04 | Difenoconazole | 1:1.33 | 9:12 |
| X.04 | Difenoconazole | 1:20 | 3:60 |
| X.04 | Difenoconazole | 1:4 | 3:12 |
| X.07 | Difenoconazole | 1:6.67 | 9:60 |
| X.07 | Difenoconazole | 1:1.33 | 9:12 |
| X.07 | Difenoconazole | 1:20 | 3:60 |
| X.07 | Difenoconazole | 1:4 | 3:12 |
| X.25 | Difenoconazole | 1:6.67 | 9:60 |
| X.25 | Difenoconazole | 1:1.33 | 9:12 |
| X.25 | Difenoconazole | 1:20 | 3:60 |
| X.25 | Difenoconazole | 1:4 | 3:12 |
| X.24 | Difenoconazole | 1:6.67 | 9:60 |
| X.24 | Difenoconazole | 1:1.33 | 9:12 |
| X.24 | Difenoconazole | 1:20 | 3:60 |
| X.24 | Difenoconazole | 1:4 | 3:12 |
| X.01 | Cyproconazole | 1:30 | 40:1200 |
| X.01 | Cyproconazole | 1:10 | 120:1200 |
| X.01 | Cyproconazole | 1:6 | 40:240 |
| X.01 | Cyproconazole | 1:2 | 120:240 |
| X.14 | Cyproconazole | 1:30 | 10:300 |
| X.14 | Cyproconazole | 1:30 | 40:1200 |
| X.14 | Cyproconazole | 1:15 | 10:150 |
| X.14 | Cyproconazole | 1:15 | 20:300 |
| X.14 | Cyproconazole | 1:10 | 120:1200 |
| X.14 | Cyproconazole | 1:7.5 | 20:150 |
| X.14 | Cyproconazole | 1:6 | 40:240 |
| X.14 | Cyproconazole | 1:2 | 120:240 |
| X.04 | Cyproconazole | 1:6.67 | 9:60 |
| X.04 | Cyproconazole | 1:1.33 | 9:12 |
| X.04 | Cyproconazole | 1:20 | 3:60 |
| X.04 | Cyproconazole | 1:4 | 3:12 |
| X.07 | Cyproconazole | 1:6.67 | 9:60 |
| X.07 | Cyproconazole | 1:1.33 | 9:12 |
| X.07 | Cyproconazole | 1:20 | 3:60 |
| X.07 | Cyproconazole | 1:4 | 3:12 |
| X.25 | Cyproconazole | 1:6.67 | 9:60 |
| X.25 | Cyproconazole | 1:1.33 | 9:12 |
| X.25 | Cyproconazole | 1:20 | 3:60 |
| X.25 | Cyproconazole | 1:4 | 3:12 |
| X.24 | Cyproconazole | 1:6.67 | 9:60 |
| X.24 | Cyproconazole | 1:1.33 | 9:12 |
| X.24 | Cyproconazole | 1:20 | 3:60 |
| X.24 | Cyproconazole | 1:4 | 3:12 |
| X.01 | Tebuconazole | 1:30 | 40:1200 |
| X.01 | Tebuconazole | 1:15 | 20:300 |
| X.01 | Tebuconazole | 1:10 | 120:1200 |
| X.01 | Tebuconazole | 1:7.5 | 20:150 |
| X.01 | Tebuconazole | 1:6 | 40:240 |
| X.01 | Tebuconazole | 1:2 | 120:240 |
| X.14 | Tebuconazole | 1:60 | 5:300 |
| X.14 | Tebuconazole | 1:30 | 40:1200 |
| X.14 | Tebuconazole | 1:30 | 10:300 |
| X.14 | Tebuconazole | 1:15 | 20:300 |
| X.14 | Tebuconazole | 1:15 | 10:150 |
| X.14 | Tebuconazole | 1:10 | 120:1200 |
| X.14 | Tebuconazole | 1:7.5 | 20:150 |
| X.14 | Tebuconazole | 1:6 | 40:240 |
| X.14 | Tebuconazole | 1:2 | 120:240 |
| X.04 | Tebuconazole | 1:6.67 | 9:60 |
| X.04 | Tebuconazole | 1:1.33 | 9:12 |
| X.04 | Tebuconazole | 1:20 | 3:60 |
| X.04 | Tebuconazole | 1:4 | 3:12 |
| X.07 | Tebuconazole | 1:6.67 | 9:60 |
| X.07 | Tebuconazole | 1:1.33 | 9:12 |
| X.07 | Tebuconazole | 1:20 | 3:60 |

-continued

| Component A (Compound) | Component B | Ratio A:B | Conc. (ppm) (A:B) |
|---|---|---|---|
| X.07 | Tebuconazole | 1:4 | 3:12 |
| X.25 | Tebuconazole | 1:6.67 | 9:60 |
| X.25 | Tebuconazole | 1:1.33 | 9:12 |
| X.25 | Tebuconazole | 1:20 | 3:60 |
| X.25 | Tebuconazole | 1:4 | 3:12 |
| X.24 | Tebuconazole | 1:6.67 | 9:60 |
| X.24 | Tebuconazole | 1:1.33 | 9:12 |
| X.24 | Tebuconazole | 1:20 | 3:60 |
| X.24 | Tebuconazole | 1:4 | 3:12 |
| X.01 | Hexaconazole | 1:30 | 40:1200 |
| X.01 | Hexaconazole | 1:10 | 120:1200 |
| X.01 | Hexaconazole | 1:6 | 40:240 |
| X.01 | Hexaconazole | 1:2 | 120:240 |
| X.14 | Hexaconazole | 1:30 | 40:1200 |
| X.14 | Hexaconazole | 1:10 | 120:1200 |
| X.14 | Hexaconazole | 1:6 | 40:240 |
| X.14 | Hexaconazole | 1:2 | 120:240 |
| X.04 | Hexaconazole | 1:6.67 | 9:60 |
| X.04 | Hexaconazole | 1:1.33 | 9:12 |
| X.04 | Hexaconazole | 1:20 | 3:60 |
| X.04 | Hexaconazole | 1:4 | 3:12 |
| X.07 | Hexaconazole | 1:6.67 | 9:60 |
| X.07 | Hexaconazole | 1:1.33 | 9:12 |
| X.07 | Hexaconazole | 1:20 | 3:60 |
| X.07 | Hexaconazole | 1:4 | 3:12 |
| X.25 | Hexaconazole | 1:6.67 | 9:60 |
| X.25 | Hexaconazole | 1:1.33 | 9:12 |
| X.25 | Hexaconazole | 1:20 | 3:60 |
| X.25 | Hexaconazole | 1:4 | 3:12 |
| X.24 | Hexaconazole | 1:6.67 | 9:60 |
| X.24 | Hexaconazole | 1:1.33 | 9:12 |
| X.24 | Hexaconazole | 1:20 | 3:60 |
| X.24 | Hexaconazole | 1:4 | 3:12 |
| X.01 | Prothioconazole | 1:60 | 5:300 |
| X.01 | Prothioconazole | 1:30 | 40:1200 |
| X.01 | Prothioconazole | 1:30 | 10:300 |
| X.01 | Prothioconazole | 1:15 | 20:300 |
| X.01 | Prothioconazole | 1:10 | 120:1200 |
| X.01 | Prothioconazole | 1:7.5 | 20:150 |
| X.01 | Prothioconazole | 1:6 | 40:240 |
| X.01 | Prothioconazole | 1:2 | 120:240 |
| X.14 | Prothioconazole | 1:60 | 5:300 |
| X.14 | Prothioconazole | 1:30 | 40:1200 |
| X.14 | Prothioconazole | 1:30 | 10:300 |
| X.14 | Prothioconazole | 1:15 | 10:150 |
| X.14 | Prothioconazole | 1:15 | 20:300 |
| X.14 | Prothioconazole | 1:10 | 120:1200 |
| X.14 | Prothioconazole | 1:7.5 | 20:150 |
| X.14 | Prothioconazole | 1:6 | 40:240 |
| X.14 | Prothioconazole | 1:2 | 120:240 |
| X.04 | Prothioconazole | 1:6.67 | 9:60 |
| X.04 | Prothioconazole | 1:1.33 | 9:12 |
| X.04 | Prothioconazole | 1:20 | 3:60 |
| X.04 | Prothioconazole | 1:4 | 3:12 |
| X.07 | Prothioconazole | 1:6.67 | 9:60 |
| X.07 | Prothioconazole | 1:1.33 | 9:12 |
| X.07 | Prothioconazole | 1:20 | 3:60 |
| X.07 | Prothioconazole | 1:4 | 3:12 |
| X.25 | Prothioconazole | 1:6.67 | 9:60 |
| X.25 | Prothioconazole | 1:1.33 | 9:12 |
| X.25 | Prothioconazole | 1:20 | 3:60 |
| X.25 | Prothioconazole | 1:4 | 3:12 |
| X.24 | Prothioconazole | 1:6.67 | 9:60 |
| X.24 | Prothioconazole | 1:1.33 | 9:12 |
| X.24 | Prothioconazole | 1:20 | 3:60 |
| X.01 | Azoxystrobin | 1:25 | 20:500 |
| X.01 | Azoxystrobin | 1:25 | 10:250 |
| X.01 | Azoxystrobin | 1:12.5 | 20:250 |
| X.14 | Azoxystrobin | 1:100 | 5:500 |
| X.14 | Azoxystrobin | 1:50 | 10:500 |
| X.14 | Azoxystrobin | 1:50 | 5:250 |
| X.14 | Azoxystrobin | 1:25 | 20:500 |
| X.14 | Azoxystrobin | 1:25 | 10:250 |
| X.14 | Azoxystrobin | 1:12.5 | 20:250 |
| X.04 | Azoxystrobin | 1:10 | 9:90 |
| X.04 | Azoxystrobin | 1:5 | 9:45 |

-continued

| Component A (Compound) | Component B | Ratio A:B | Conc. (ppm) (A:B) |
|---|---|---|---|
| X.04 | Azoxystrobin | 1:30 | 3:90 |
| X.04 | Azoxystrobin | 1:15 | 3:45 |
| X.07 | Azoxystrobin | 1:10 | 9:90 |
| X.07 | Azoxystrobin | 1:5 | 9:45 |
| X.07 | Azoxystrobin | 1:30 | 3:90 |
| X.07 | Azoxystrobin | 1:15 | 3:45 |
| X.25 | Azoxystrobin | 1:10 | 9:90 |
| X.25 | Azoxystrobin | 1:5 | 9:45 |
| X.25 | Azoxystrobin | 1:30 | 3:90 |
| X.25 | Azoxystrobin | 1:15 | 3:45 |
| X.24 | Azoxystrobin | 1:10 | 9:90 |
| X.24 | Azoxystrobin | 1:5 | 9:45 |
| X.24 | Azoxystrobin | 1:30 | 3:90 |
| X.24 | Azoxystrobin | 1:15 | 3:45 |
| X.01 | Trifloxystrobin | 1:100 | 5:500 |
| X.01 | Trifloxystrobin | 1:50 | 10:500 |
| X.01 | Trifloxystrobin | 1:25 | 20:500 |
| X.01 | Trifloxystrobin | 1:25 | 10:250 |
| X.14 | Trifloxystrobin | 1:200 | 2.5:500 |
| X.14 | Trifloxystrobin | 1:100 | 5:500 |
| X.14 | Trifloxystrobin | 1:50 | 5:250 |
| X.14 | Trifloxystrobin | 1:50 | 10:500 |
| X.14 | Trifloxystrobin | 1:25 | 10:250 |
| X.14 | Trifloxystrobin | 1:12.5 | 20:250 |
| X.14 | Trifloxystrobin | 1:12.5 | 10:125 |
| X.14 | Trifloxystrobin | 1:6.25 | 20:125 |
| X.04 | Trifloxystrobin | 1:10 | 9:90 |
| X.04 | Trifloxystrobin | 1:5 | 9:45 |
| X.04 | Trifloxystrobin | 1:30 | 3:90 |
| X.04 | Trifloxystrobin | 1:15 | 3:45 |
| X.07 | Trifloxystrobin | 1:10 | 9:90 |
| X.07 | Trifloxystrobin | 1:5 | 9:45 |
| X.07 | Trifloxystrobin | 1:30 | 3:90 |
| X.07 | Trifloxystrobin | 1:15 | 3:45 |
| X.25 | Trifloxystrobin | 1:10 | 9:90 |
| X.25 | Trifloxystrobin | 1:5 | 9:45 |
| X.25 | Trifloxystrobin | 1:30 | 3:90 |
| X.25 | Trifloxystrobin | 1:15 | 3:45 |
| X.24 | Trifloxystrobin | 1:10 | 9:90 |
| X.24 | Trifloxystrobin | 1:5 | 9:45 |
| X.24 | Trifloxystrobin | 1:30 | 3:90 |
| X.24 | Trifloxystrobin | 1:15 | 3:45 |
| X.01 | Picoxystrobin | 1:100 | 5:500 |
| X.01 | Picoxystrobin | 1:50 | 10:500 |
| X.01 | Picoxystrobin | 1:25 | 20:500 |
| X.01 | Picoxystrobin | 1:25 | 10:250 |
| X.01 | Picoxystrobin | 1:12.5 | 20:250 |
| X.04 | Picoxystrobin | 1:10 | 9:90 |
| X.04 | Picoxystrobin | 1:5 | 9:45 |
| X.04 | Picoxystrobin | 1:30 | 3:90 |
| X.04 | Picoxystrobin | 1:15 | 3:45 |
| X.07 | Picoxystrobin | 1:10 | 9:90 |
| X.07 | Picoxystrobin | 1:5 | 9:45 |
| X.07 | Picoxystrobin | 1:30 | 3:90 |
| X.07 | Picoxystrobin | 1:15 | 3:45 |
| X.25 | Picoxystrobin | 1:10 | 9:90 |
| X.25 | Picoxystrobin | 1:5 | 9:45 |
| X.25 | Picoxystrobin | 1:30 | 3:90 |
| X.25 | Picoxystrobin | 1:15 | 3:45 |
| X.24 | Picoxystrobin | 1:10 | 9:90 |
| X.24 | Picoxystrobin | 1:5 | 9:45 |
| X.24 | Picoxystrobin | 1:30 | 3:90 |
| X.24 | Picoxystrobin | 1:15 | 3:45 |
| X.04 | Pyraclostrobin | 1:10 | 9:90 |
| X.04 | Pyraclostrobin | 1:5 | 9:45 |
| X.04 | Pyraclostrobin | 1:30 | 3:90 |
| X.04 | Pyraclostrobin | 1:15 | 3:45 |
| X.07 | Pyraclostrobin | 1:10 | 9:90 |
| X.07 | Pyraclostrobin | 1:5 | 9:45 |
| X.07 | Pyraclostrobin | 1:30 | 3:90 |
| X.07 | Pyraclostrobin | 1:15 | 3:45 |
| X.25 | Pyraclostrobin | 1:10 | 9:90 |
| X.25 | Pyraclostrobin | 1:5 | 9:45 |
| X.25 | Pyraclostrobin | 1:30 | 3:90 |
| X.25 | Pyraclostrobin | 1:15 | 3:45 |
| X.24 | Pyraclostrobin | 1:10 | 9:90 |

-continued

| Component A (Compound) | Component B | Ratio A:B | Conc. (ppm) (A:B) |
|---|---|---|---|
| X.24 | Pyraclostrobin | 1:5 | 9:45 |
| X.24 | Pyraclostrobin | 1:30 | 3:90 |
| X.24 | Pyraclostrobin | 1:15 | 3:45 |
| X.01 | Metalaxyl-M | 1:150 | 40:6000 |
| X.01 | Metalaxyl-M | 1:50 | 120:6000 |
| X.01 | Metalaxyl-M | 1:50 | 40:2000 |
| X.01 | Metalaxyl-M | 1:16.7 | 120:2000 |
| X.14 | Metalaxyl-M | 1:150 | 40:6000 |
| X.14 | Metalaxyl-M | 1:100 | 20:2000 |
| X.14 | Metalaxyl-M | 1:100 | 10:1000 |
| X.14 | Metalaxyl-M | 1:50 | 20:1000 |
| X.14 | Metalaxyl-M | 1:50 | 120:6000 |
| X.14 | Metalaxyl-M | 1:50 | 40:2000 |
| X.14 | Metalaxyl-M | 1:16.7 | 120:2000 |
| X.04 | Metalaxyl-M | 1:33.33 | 9:300 |
| X.04 | Metalaxyl-M | 1:11.11 | 9:100 |
| X.04 | Metalaxyl-M | 1:100 | 3:300 |
| X.04 | Metalaxyl-M | 1:33.33 | 3:100 |
| X.07 | Metalaxyl-M | 1:33.33 | 9:300 |
| X.07 | Metalaxyl-M | 1:11.11 | 9:100 |
| X.07 | Metalaxyl-M | 1:100 | 3:300 |
| X.07 | Metalaxyl-M | 1:33.33 | 3:100 |
| X.25 | Metalaxyl-M | 1:33.33 | 9:300 |
| X.25 | Metalaxyl-M | 1:11.11 | 9:100 |
| X.25 | Metalaxyl-M | 1:100 | 3:300 |
| X.25 | Metalaxyl-M | 1:33.33 | 3:100 |
| X.24 | Metalaxyl-M | 1:33.33 | 9:300 |
| X.24 | Metalaxyl-M | 1:11.11 | 9:100 |
| X.24 | Metalaxyl-M | 1:100 | 3:300 |
| X.24 | Metalaxyl-M | 1:33.33 | 3:100 |
| X.01 | Fenpropidin | 1:400 | 5:2000 |
| X.01 | Fenpropidin | 1:100 | 20:2000 |
| X.01 | Fenpropidin | 1:100 | 10:1000 |
| X.01 | Fenpropidin | 1:50 | 20:1000 |
| X.14 | Fenpropidin | 1:200 | 10:2000 |
| X.14 | Fenpropidin | 1:200 | 5:1000 |
| X.14 | Fenpropidin | 1:100 | 20:2000 |
| X.14 | Fenpropidin | 1:100 | 10:1000 |
| X.14 | Fenpropidin | 1:50 | 20:1000 |
| X.04 | Fenpropidin | 1:33.33 | 9:300 |
| X.04 | Fenpropidin | 1:11.11 | 9:100 |
| X.04 | Fenpropidin | 1:100 | 3:300 |
| X.04 | Fenpropidin | 1:33.33 | 3:100 |
| X.07 | Fenpropidin | 1:33.33 | 9:300 |
| X.07 | Fenpropidin | 1:11.11 | 9:100 |
| X.07 | Fenpropidin | 1:100 | 3:300 |
| X.07 | Fenpropidin | 1:33.33 | 3:100 |
| X.25 | Fenpropidin | 1:33.33 | 9:300 |
| X.25 | Fenpropidin | 1:11.11 | 9:100 |
| X.25 | Fenpropidin | 1:100 | 3:300 |
| X.25 | Fenpropidin | 1:33.33 | 3:100 |
| X.24 | Fenpropidin | 1:33.33 | 9:300 |
| X.24 | Fenpropidin | 1:11.11 | 9:100 |
| X.24 | Fenpropidin | 1:100 | 3:300 |
| X.24 | Fenpropidin | 1:33.33 | 3:100 |
| X.01 | Fenpropimorph | 1:600 | 5:3000 |
| X.01 | Fenpropimorph | 1:300 | 10:3000 |
| X.01 | Fenpropimorph | 1:150 | 20:3000 |
| X.04 | Fenpropimorph | 1:33.33 | 9:300 |
| X.04 | Fenpropimorph | 1:11.11 | 9:100 |
| X.04 | Fenpropimorph | 1:100 | 3:300 |
| X.04 | Fenpropimorph | 1:33.33 | 3:100 |
| X.07 | Fenpropimorph | 1:33.33 | 9:300 |
| X.07 | Fenpropimorph | 1:11.11 | 9:100 |
| X.07 | Fenpropimorph | 1:100 | 3:300 |
| X.07 | Fenpropimorph | 1:33.33 | 3:100 |
| X.25 | Fenpropimorph | 1:33.33 | 9:300 |
| X.25 | Fenpropimorph | 1:11.11 | 9:100 |
| X.25 | Fenpropimorph | 1:100 | 3:300 |
| X.25 | Fenpropimorph | 1:33.33 | 3:100 |
| X.24 | Fenpropimorph | 1:33.33 | 9:300 |
| X.24 | Fenpropimorph | 1:11.11 | 9:100 |
| X.24 | Fenpropimorph | 1:100 | 3:300 |
| X.24 | Fenpropimorph | 1:33.33 | 3:100 |
| X.01 | Cyprodinil | 1:6000 | 5:30000 |
| X.01 | Cyprodinil | 1:3000 | 10:30000 |
| X.01 | Cyprodinil | 1:1500 | 10:15000 |
| X.01 | Cyprodinil | 1:750 | 20:15000 |
| X.14 | Cyprodinil | 1:6000 | 5:30000 |
| X.14 | Cyprodinil | 1:6000 | 2.5:15000 |
| X.14 | Cyprodinil | 1:3000 | 10:30000 |
| X.14 | Cyprodinil | 1:1500 | 10:15000 |
| X.04 | Cyprodinil | 1:100 | 9:900 |
| X.04 | Cyprodinil | 1:33.33 | 9:300 |
| X.04 | Cyprodinil | 1:300 | 3:900 |
| X.04 | Cyprodinil | 1:100 | 3:300 |
| X.07 | Cyprodinil | 1:100 | 9:900 |
| X.07 | Cyprodinil | 1:33.33 | 9:300 |
| X.07 | Cyprodinil | 1:300 | 3:900 |
| X.07 | Cyprodinil | 1:100 | 3:300 |
| X.25 | Cyprodinil | 1:100 | 9:900 |
| X.25 | Cyprodinil | 1:33.33 | 9:300 |
| X.25 | Cyprodinil | 1:300 | 3:900 |
| X.25 | Cyprodinil | 1:100 | 3:300 |
| X.24 | Cyprodinil | 1:100 | 9:900 |
| X.24 | Cyprodinil | 1:33.33 | 9:300 |
| X.24 | Cyprodinil | 1:300 | 3:900 |
| X.24 | Cyprodinil | 1:100 | 3:300 |
| X.04 | Fludioxinil | 1:200 | 9:1800 |
| X.04 | Fludioxinil | 1:66.67 | 9:600 |
| X.04 | Fludioxinil | 1:600 | 3:1800 |
| X.04 | Fludioxinil | 1:200 | 3:600 |
| X.07 | Fludioxinil | 1:200 | 9:1800 |
| X.07 | Fludioxinil | 1:66.67 | 9:600 |
| X.07 | Fludioxinil | 1:600 | 3:1800 |
| X.25 | Fludioxinil | 1:200 | 9:1800 |
| X.25 | Fludioxinil | 1:66.67 | 9:600 |
| X.25 | Fludioxinil | 1:600 | 3:1800 |
| X.25 | Fludioxinil | 1:200 | 3:600 |
| X.24 | Fludioxinil | 1:200 | 9:1800 |
| X.24 | Fludioxinil | 1:66.67 | 9:600 |
| X.01 | Spiroxamine | 1:1200 | 5:6000 |
| X.01 | Spiroxamine | 1:600 | 10:6000 |
| X.01 | Spiroxamine | 1:300 | 20:6000 |
| X.01 | Spiroxamine | 1:300 | 10:3000 |
| X.01 | Spiroxamine | 1:150 | 20:3000 |
| X.14 | Spiroxamine | 1:2400 | 2.5:6000 |
| X.14 | Spiroxamine | 1:1200 | 2.5:3000 |
| X.14 | Spiroxamine | 1:1200 | 5:6000 |
| X.14 | Spiroxamine | 1:600 | 10:6000 |
| X.14 | Spiroxamine | 1:600 | 5:3000 |
| X.14 | Spiroxamine | 1:300 | 10:3000 |
| X.04 | Spiroxamine | 1:33.33 | 9:300 |
| X.04 | Spiroxamine | 1:11.11 | 9:100 |
| X.04 | Spiroxamine | 1:100 | 3:300 |
| X.04 | Spiroxamine | 1:33.33 | 3:100 |
| X.07 | Spiroxamine | 1:33.33 | 9:300 |
| X.07 | Spiroxamine | 1:11.11 | 9:100 |
| X.07 | Spiroxamine | 1:100 | 3:300 |
| X.04 | Spiroxamine | 1:33.33 | 3:100 |
| X.25 | Spiroxamine | 1:33.33 | 9:300 |
| X.25 | Spiroxamine | 1:11.11 | 9:100 |
| X.25 | Spiroxamine | 1:100 | 3:300 |
| X.25 | Spiroxamine | 1:33.33 | 3:100 |
| X.24 | Spiroxamine | 1:33.33 | 9:300 |
| X.24 | Spiroxamine | 1:11.11 | 9:100 |
| X.24 | Spiroxamine | 1:100 | 3:300 |
| X.24 | Spiroxamine | 1:33.33 | 3:100 |
| X.01 | Mancozeb | 1:500 | 20:10000 |
| X.01 | Mancozeb | 1:250 | 20:5000 |
| X.01 | Mancozeb | 1:1000 | 5:5000 |
| X.14 | Mancozeb | 1:500 | 20:10000 |
| X.14 | Mancozeb | 1:500 | 10:5000 |
| X.14 | Mancozeb | 1:250 | 20:5000 |
| X.14 | Mancozeb | 1:1000 | 10:10000 |
| X.04 | Mancozeb | 1:100 | 9:900 |
| X.04 | Mancozeb | 1:33.33 | 9:300 |
| X.04 | Mancozeb | 1:300 | 3:900 |
| X.04 | Mancozeb | 1:100 | 3:300 |
| X.07 | Mancozeb | 1:100 | 9:900 |
| X.07 | Mancozeb | 1:33.33 | 9:300 |
| X.07 | Mancozeb | 1:300 | 3:900 |

| Component A (Compound) | Component B | Ratio A:B | Conc. (ppm) (A:B) |
|---|---|---|---|
| X.07 | Mancozeb | 1:100 | 3:300 |
| X.25 | Mancozeb | 1:100 | 9:900 |
| X.25 | Mancozeb | 1:33.33 | 9:300 |
| X.25 | Mancozeb | 1:300 | 3:900 |
| X.25 | Mancozeb | 1:100 | 3:300 |
| X.24 | Mancozeb | 1:100 | 9:900 |
| X.24 | Mancozeb | 1:33.33 | 9:300 |
| X.24 | Mancozeb | 1:300 | 3:900 |
| X.24 | Mancozeb | 1:100 | 3:300 |
| X.01 | Chlorothalonil | 1:1500 | 40:60000 |
| X.01 | Chlorothalonil | 1:500 | 120:60000 |
| X.01 | Chlorothalonil | 1:500 | 40:20000 |
| X.01 | Chlorothalonil | 1:166.7 | 120:20000 |
| X.14 | Chlorothalonil | 1:4000 | 10:40000 |
| X.14 | Chlorothalonil | 1:2000 | 20:40000 |
| X.14 | Chlorothalonil | 1:1500 | 40:60000 |
| X.14 | Chlorothalonil | 1:1000 | 20:20000 |
| X.14 | Chlorothalonil | 1:500 | 120:60000 |
| X.14 | Chlorothalonil | 1:500 | 40:20000 |
| X.14 | Chlorothalonil | 1:166.7 | 120:20000 |
| X.04 | Chlorothalonil | 1:200 | 9:1800 |
| X.04 | Chlorothalonil | 1:66.67 | 9:600 |
| X.04 | Chlorothalonil | 1:600 | 3:1800 |
| X.04 | Chlorothalonil | 1:200 | 3:600 |
| X.07 | Chlorothalonil | 1:200 | 9:1800 |
| X.07 | Chlorothalonil | 1:66.67 | 9:600 |
| X.07 | Chlorothalonil | 1:600 | 3:1800 |
| X.07 | Chlorothalonil | 1:200 | 3:600 |
| X.25 | Chlorothalonil | 1:200 | 9:1800 |
| X.25 | Chlorothalonil | 1:66.67 | 9:600 |
| X.25 | Chlorothalonil | 1:600 | 3:1800 |
| X.25 | Chlorothalonil | 1:200 | 3:600 |
| X.24 | Chlorothalonil | 1:200 | 9:1800 |
| X.24 | Chlorothalonil | 1:66.67 | 9:600 |
| X.24 | Chlorothalonil | 1:600 | 3:1800 |
| X.24 | Chlorothalonil | 1:200 | 3:600 |
| X.04 | Fenhexamid | 1:100 | 9:900 |
| X.04 | Fenhexamid | 1:33.33 | 9:300 |
| X.04 | Fenhexamid | 1:300 | 3:900 |
| X.04 | Fenhexamid | 1:100 | 3:300 |
| X.07 | Fenhexamid | 1:100 | 9:900 |
| X.07 | Fenhexamid | 1:33.33 | 9:300 |
| X.07 | Fenhexamid | 1:300 | 3:900 |
| X.07 | Fenhexamid | 1:100 | 3:300 |
| X.25 | Fenhexamid | 1:100 | 9:900 |
| X.25 | Fenhexamid | 1:33.33 | 9:300 |
| X.25 | Fenhexamid | 1:300 | 3:900 |
| X.25 | Fenhexamid | 1:100 | 3:300 |
| X.24 | Fenhexamid | 1:100 | 9:900 |
| X.24 | Fenhexamid | 1:33.33 | 9:300 |
| X.24 | Fenhexamid | 1:300 | 3:900 |
| X.24 | Fenhexamid | 1:100 | 3:300 |
| X.04 | Prochloraz | 1:100 | 9:900 |
| X.04 | Prochloraz | 1:33.33 | 9:300 |
| X.04 | Prochloraz | 1:300 | 3:900 |
| X.04 | Prochloraz | 1:100 | 3:300 |
| X.07 | Prochloraz | 1:100 | 9:900 |
| X.07 | Prochloraz | 1:33.33 | 9:300 |
| X.07 | Prochloraz | 1:100 | 3:300 |
| X.25 | Prochloraz | 1:100 | 9:900 |
| X.25 | Prochloraz | 1:33.33 | 9:300 |
| X.25 | Prochloraz | 1:300 | 3:900 |
| X.25 | Prochloraz | 1:100 | 3:300 |
| X.24 | Prochloraz | 1:100 | 9:900 |
| X.24 | Prochloraz | 1:33.33 | 9:300 |
| X.24 | Prochloraz | 1:300 | 3:900 |
| X.24 | Prochloraz | 1:100 | 3:300 |
| X.01 | Oxathiapiprolin | 1:5 | 120:600 |
| X.01 | Oxathiapiprolin | 1:1.7 | 120:200 |
| X.14 | Oxathiapiprolin | 1:15 | 40:600 |
| X.14 | Oxathiapiprolin | 1:5 | 120:600 |
| X.14 | Oxathiapiprolin | 1:5 | 40:200 |
| X.14 | Oxathiapiprolin | 1:1.7 | 120:200 |
| X.04 | Oxathiapiprolin | 1:3.33 | 9:30 |
| X.04 | Oxathiapiprolin | 1:1.11 | 9:10 |
| X.04 | Oxathiapiprolin | 1:10 | 3:30 |
| X.04 | Oxathiapiprolin | 1:3.33 | 3:10 |
| X.07 | Oxathiapiprolin | 1:3.33 | 9:30 |
| X.07 | Oxathiapiprolin | 1:1.11 | 9:10 |
| X.07 | Oxathiapiprolin | 1:10 | 3:30 |
| X.07 | Oxathiapiprolin | 1:3.33 | 3:10 |
| X.25 | Oxathiapiprolin | 1:3.33 | 9:30 |
| X.25 | Oxathiapiprolin | 1:1.11 | 9:10 |
| X.25 | Oxathiapiprolin | 1:10 | 3:30 |
| X.25 | Oxathiapiprolin | 1:3.33 | 3:10 |
| X.24 | Oxathiapiprolin | 1:3.33 | 9:30 |
| X.24 | Oxathiapiprolin | 1:1.11 | 9:10 |
| X.24 | Oxathiapiprolin | 1:10 | 3:30 |
| X.24 | Oxathiapiprolin | 1:3.33 | 3:10 |
| X.01 | Mandipropamid | 120:6000 | 120:6000 |
| X.01 | Mandipropamid | 120:2000 | 120:2000 |
| X.14 | Mandipropamid | 1:150 | 40:6000 |
| X.14 | Mandipropamid | 1:50 | 120:6000 |
| X.14 | Mandipropamid | 1:50 | 40:2000 |
| X.14 | Mandipropamid | 1:16.7 | 120:2000 |
| X.04 | Mandipropamid | 1:33.33 | 9:300 |
| X.04 | Mandipropamid | 1:11.11 | 9:100 |
| X.04 | Mandipropamid | 1:100 | 3:300 |
| X.04 | Mandipropamid | 1:33.33 | 3:100 |
| X.07 | Mandipropamid | 1:33.33 | 9:300 |
| X.07 | Mandipropamid | 1:11.11 | 9:100 |
| X.07 | Mandipropamid | 1:100 | 3:300 |
| X.07 | Mandipropamid | 1:33.33 | 3:100 |
| X.25 | Mandipropamid | 1:33.33 | 9:300 |
| X.25 | Mandipropamid | 1:11.11 | 9:100 |
| X.25 | Mandipropamid | 1:100 | 3:300 |
| X.25 | Mandipropamid | 1:33.33 | 3:100 |
| X.24 | Mandipropamid | 1:33.33 | 9:300 |
| X.24 | Mandipropamid | 1:11.11 | 9:100 |
| X.24 | Mandipropamid | 1:100 | 3:300 |
| X.24 | Mandipropamid | 1:33.33 | 3:100 |
| X.01 | Fluazinam | 1:375 | 40:15000 |
| X.01 | Fluazinam | 1:125 | 120:15000 |
| X.01 | Fluazinam | 1:41.7 | 120:5000 |
| X.14 | Fluazinam | 1:375 | 40:15000 |
| X.14 | Fluazinam | 1:125 | 40:5000 |
| X.14 | Fluazinam | 1:125 | 120:15000 |
| X.14 | Fluazinam | 1:41.7 | 120:5000 |
| X.04 | Fluazinam | 1:90 | 9:810 |
| X.04 | Fluazinam | 1:30 | 9:270 |
| X.04 | Fluazinam | 1:270 | 3:810 |
| X.04 | Fluazinam | 1:90 | 3:270 |
| X.07 | Fluazinam | 1:90 | 9:810 |
| X.07 | Fluazinam | 1:30 | 9:270 |
| X.07 | Fluazinam | 1:270 | 3:810 |
| X.07 | Fluazinam | 1:90 | 3:270 |
| X.25 | Fluazinam | 1:90 | 9:810 |
| X.25 | Fluazinam | 1:30 | 9:270 |
| X.25 | Fluazinam | 1:270 | 3:810 |
| X.25 | Fluazinam | 1:90 | 3:270 |
| X.24 | Fluazinam | 1:90 | 9:810 |
| X.24 | Fluazinam | 1:30 | 9:270 |
| X.24 | Fluazinam | 1:270 | 3:810 |
| X.24 | Fluazinam | 1:90 | 3:270 |
| X.01 | (N'-[5-bromo-2-methyl-6-(1-methyl-2-propoxy-ethoxy)-3-pyridyl]-N-ethyl-N-methyl-formamidine) | 1:3 | 40:120 |
| X.01 | (N'-[5-bromo-2-methyl-6-(1-methyl-2-propoxy-ethoxy)-3-pyridyl]-N-ethyl-N-methyl-formamidine) | 1:1 | 120:120 |
| X.01 | (N'-[5-bromo-2-methyl-6-(1-methyl-2-propoxy-ethoxy)-3-pyridyl]-N-ethyl-N-methyl-formamidine) | 1:1 | 40:40 |

| Component A (Compound) | Component B | Ratio A:B | Conc. (ppm) (A:B) |
|---|---|---|---|
| X.01 | (N'-[5-bromo-2-methyl-6-(1-methyl-2-propoxy-ethoxy)-3-pyridyl]-N-ethyl-N-methyl-formamidine) | 3:1 | 120:40 |
| X.14 | (N'-[5-bromo-2-methyl-6-(1-methyl-2-propoxy-ethoxy)-3-pyridyl]-N-ethyl-N-methyl-formamidine) | 1:3 | 40:120 |
| X.14 | (N'-[5-bromo-2-methyl-6-(1-methyl-2-propoxy-ethoxy)-3-pyridyl]-N-ethyl-N-methyl-formamidine) | 1:1 | 120:120 |
| X.14 | (N'-[5-bromo-2-methyl-6-(1-methyl-2-propoxy-ethoxy)-3-pyridyl]-N-ethyl-N-methyl-formamidine) | 1:1 | 40:40 |
| X.14 | (N'-[5-bromo-2-methyl-6-(1-methyl-2-propoxy-ethoxy)-3-pyridyl]-N-ethyl-N-methyl-formamidine) | 3:1 | 120:40 |
| X.04 | (N'-[5-bromo-2-methyl-6-(1-methyl-2-propoxy-ethoxy)-3-pyridyl]-N-ethyl-N-methyl-formamidine) | 1.5:1 | 9:6 |
| X.04 | (N'-[5-bromo-2-methyl-6-(1-methyl-2-propoxy-ethoxy)-3-pyridyl]-N-ethyl-N-methyl-formamidine) | 3:1 | 9:3 |
| X.04 | (N'-[5-bromo-2-methyl-6-(1-methyl-2-propoxy-ethoxy)-3-pyridyl]-N-ethyl-N-methyl-formamidine) | 1:2 | 3:6 |
| X.04 | (N'-[5-bromo-2-methyl-6-(1-methyl-2-propoxy-ethoxy)-3-pyridyl]-N-ethyl-N-methyl-formamidine) | 1:1 | 3:3 |
| X.07 | (N'-[5-bromo-2-methyl-6-(1-methyl-2-propoxy-ethoxy)-3-pyridyl]-N-ethyl-N-methyl-formamidine) | 1.5:1 | 9:6 |
| X.07 | (N'-[5-bromo-2-methyl-6-(1-methyl-2-propoxy-ethoxy)-3-pyridyl]-N-ethyl-N-methyl-formamidine) | 3:1 | 9:3 |
| X.07 | (N'-[5-bromo-2-methyl-6-(1-methyl-2-propoxy-ethoxy)-3-pyridyl]-N-ethyl-N-methyl-formamidine) | 1:2 | 3:6 |
| X.07 | (N'-[5-bromo-2-methyl-6-(1-methyl-2-propoxy-ethoxy)-3-pyridyl]-N-ethyl-N-methyl-formamidine) | 1:1 | 3:3 |
| X.25 | (N'-[5-bromo-2-methyl-6-(1-methyl-2-propoxy-ethoxy)-3-pyridyl]-N-ethyl-N-methyl-formamidine) | 1.5:1 | 9:6 |
| X.25 | (N'-[5-bromo-2-methyl-6-(1-methyl-2-propoxy-ethoxy)-3-pyridyl]-N-ethyl-N-methyl-formamidine) | 3:1 | 9:3 |
| X.25 | (N'-[5-bromo-2-methyl-6-(1-methyl-2-propoxy-ethoxy)-3-pyridyl]-N-ethyl-N-methyl-formamidine) | 1:2 | 3:6 |
| X.25 | (N'-[5-bromo-2-methyl-6-(1-methyl-2-propoxy-ethoxy)-3-pyridyl]-N-ethyl-N-methyl-formamidine) | 1:1 | 3:3 |
| X.24 | (N'-[5-bromo-2-methyl-6-(1-methyl-2-propoxy-ethoxy)-3-pyridyl]-N-ethyl-N-methyl-formamidine) | 1.5:1 | 9:6 |
| X.24 | (N'-[5-bromo-2-methyl-6-(1-methyl-2-propoxy-ethoxy)-3-pyridyl]-N-ethyl-N-methyl-formamidine) | 3:1 | 9:3 |
| X.24 | (N'-[5-bromo-2-methyl-6-(1-methyl-2-propoxy-ethoxy)-3-pyridyl]-N-ethyl-N-methyl-formamidine) | 1:2 | 3:6 |
| X.24 | (N'-[5-bromo-2-methyl-6-(1-methyl-2-propoxy-ethoxy)-3-pyridyl]-N-ethyl-N-methyl-formamidine) | 1:1 | 3:3 |
| X.01 | fosetyl-aluminium | 1:1500 | 40:60000 |
| X.01 | fosetyl-aluminium | 1:500 | 120:60000 |
| X.01 | fosetyl-aluminium | 1:500 | 40:20000 |
| X.01 | fosetyl-aluminium | 3:167 | 120:20000 |
| X.14 | fosetyl-aluminium | 1:1500 | 40:60000 |
| X.14 | fosetyl-aluminium | 1:500 | 120:60000 |
| X.14 | fosetyl-aluminium | 1:500 | 40:20000 |
| X.14 | fosetyl-aluminium | 3:167 | 120:20000 |
| X.04 | fosetyl-aluminium | 1:666.67 | 9:6000 |
| X.04 | fosetyl-aluminium | 1:333.33 | 9:3000 |
| X.04 | fosetyl-aluminium | 1:2000 | 3:6000 |
| X.04 | fosetyl-aluminium | 1:1000 | 3:3000 |
| X.07 | fosetyl-aluminium | 1:666.67 | 9:6000 |
| X.07 | fosetyl-aluminium | 1:333.33 | 9:3000 |
| X.07 | fosetyl-aluminium | 1:2000 | 3:6000 |
| X.07 | fosetyl-aluminium | 1:1000 | 3:3000 |
| X.25 | fosetyl-aluminium | 1:333.33 | 9:3000 |
| X.25 | fosetyl-aluminium | 1:166.67 | 9:1500 |
| X.25 | fosetyl-aluminium | 1:1000 | 3:3000 |
| X.25 | fosetyl-aluminium | 1:500 | 3:1500 |
| X.24 | fosetyl-aluminium | 1:333.33 | 9:3000 |
| X.24 | fosetyl-aluminium | 1:166.67 | 9:1500 |
| X.24 | fosetyl-aluminium | 1:1000 | 3:3000 |
| X.24 | fosetyl-aluminium | 1:500 | 3:1500 |
| X.01 | Trinexapac-ethyl | 1:250 | 20:5000 |
| X.01 | Trinexapac-ethyl | 1:150 | 40:6000 |
| X.01 | Trinexapac-ethyl | 1:125 | 20:2500 |
| X.01 | Trinexapac-ethyl | 1:50 | 120:6000 |
| X.01 | Trinexapac-ethyl | 1:50 | 40:2000 |
| X.01 | Trinexapac-ethyl | 1:16.7 | 120:2000 |
| X.14 | Trinexapac-ethyl | 1:500 | 10:5000 |
| X.14 | Trinexapac-ethyl | 1:150 | 40:6000 |
| X.14 | Trinexapac-ethyl | 1:50 | 120:6000 |
| X.14 | Trinexapac-ethyl | 1:50 | 40:2000 |
| X.14 | Trinexapac-ethyl | 1:16.7 | 120:2000 |
| X.04 | Trinexapac-ethyl | 1:33.33 | 9:300 |
| X.04 | Trinexapac-ethyl | 1:16.67 | 9:150 |
| X.04 | Trinexapac-ethyl | 1:100 | 3:300 |
| X.04 | Trinexapac-ethyl | 1:50 | 3:150 |
| X.07 | Trinexapac-ethyl | 1:33.33 | 9:300 |
| X.07 | Trinexapac-ethyl | 1:16.67 | 9:150 |
| X.07 | Trinexapac-ethyl | 1:100 | 3:300 |
| X.07 | Trinexapac-ethyl | 1:50 | 3:150 |
| X.25 | Trinexapac-ethyl | 1:33.33 | 9:300 |
| X.25 | Trinexapac-ethyl | 1:16.67 | 9:150 |
| X.25 | Trinexapac-ethyl | 1:100 | 3:300 |

-continued

| Component A (Compound) | Component B | Ratio A:B | Conc. (ppm) (A:B) |
|---|---|---|---|
| X.25 | Trinexapac-ethyl | 1:50 | 3:150 |
| X.24 | Trinexapac-ethyl | 1:33.33 | 9:300 |
| X.24 | Trinexapac-ethyl | 1:16.67 | 9:150 |
| X.24 | Trinexapac-ethyl | 1:100 | 3:300 |
| X.24 | Trinexapac-ethyl | 1:50 | 3:150 |
| X.01 | Acibenzolar-S-methyl | 1:15 | 40:600 |
| X.01 | Acibenzolar-S-methyl | 1:5 | 120:600 |
| X.01 | Acibenzolar-S-methyl | 1:5 | 40:200 |
| X.01 | Acibenzolar-S-methyl | 1:1.7 | 120:200 |
| X.14 | Acibenzolar-S-methyl | 1:15 | 40:600 |
| X.14 | Acibenzolar-S-methyl | 1:5 | 120:600 |
| X.14 | Acibenzolar-S-methyl | 1:5 | 40:200 |
| X.14 | Acibenzolar-S-methyl | 1:1.7 | 120:200 |
| X.04 | Acibenzolar-S-methyl | 1:10 | 9:90 |
| X.04 | Acibenzolar-S-methyl | 1:30 | 3:90 |
| X.07 | Acibenzolar-S-methyl | 1:10 | 9:90 |
| X.07 | Acibenzolar-S-methyl | 1:5 | 9:45 |
| X.07 | Acibenzolar-S-methyl | 1:30 | 3:90 |
| X.07 | Acibenzolar-S-methyl | 1:15 | 3:45 |
| X.25 | Acibenzolar-S-methyl | 1:10 | 9:90 |
| X.25 | Acibenzolar-S-methyl | 1:5 | 9:45 |
| X.25 | Acibenzolar-S-methyl | 1:30 | 3:90 |
| X.25 | Acibenzolar-S-methyl | 1:15 | 3:45 |
| X.24 | Acibenzolar-S-methyl | 1:10 | 9:90 |
| X.24 | Acibenzolar-S-methyl | 1:5 | 9:45 |
| X.24 | Acibenzolar-S-methyl | 1:30 | 3:90 |
| X.24 | Acibenzolar-S-methyl | 1:15 | 3:45 |
| X.01 | Glyphosate | 1:2400 | 5:12000 |
| X.01 | Glyphosate | 1:1200 | 10:12000 |
| X.01 | Glyphosate | 1:600 | 20:12000 |
| X.01 | Glyphosate | 1:300 | 20:6000 |
| X.14 | Glyphosate | 1:2400 | 5:12000 |
| X.14 | Glyphosate | 1:1200 | 10:12000 |
| X.14 | Glyphosate | 1:1200 | 5:6000 |
| X.14 | Glyphosate | 1:600 | 10:6000 |
| X.04 | Glyphosate | 1:20 | 9:180 |
| X.04 | Glyphosate | 1:6.67 | 9:60 |
| X.04 | Glyphosate | 1:60 | 3:180 |
| X.04 | Glyphosate | 1:20 | 3:60 |
| X.07 | Glyphosate | 1:20 | 9:180 |
| X.07 | Glyphosate | 1:6.67 | 9:60 |
| X.07 | Glyphosate | 1:60 | 3:180 |
| X.07 | Glyphosate | 1:20 | 3:60 |
| X.25 | Glyphosate | 1:20 | 9:180 |
| X.25 | Glyphosate | 1:6.67 | 9:60 |
| X.25 | Glyphosate | 1:60 | 3:180 |
| X.25 | Glyphosate | 1:20 | 3:60 |
| X.24 | Glyphosate | 1:20 | 9:180 |
| X.24 | Glyphosate | 1:6.67 | 9:60 |
| X.24 | Glyphosate | 1:60 | 3:180 |
| X.24 | Glyphosate | 1:20 | 3:60 |
| X.04 | 2,4-D | 1:20 | 9:180 |
| X.04 | 2,4-D | 1:6.67 | 9:60 |
| X.04 | 2,4-D | 1:60 | 3:180 |
| X.04 | 2,4-D | 1:20 | 3:60 |
| X.07 | 2,4-D | 1:20 | 9:180 |
| X.07 | 2,4-D | 1:6.67 | 9:60 |
| X.07 | 2,4-D | 1:60 | 3:180 |
| X.07 | 2,4-D | 1:20 | 3:60 |
| X.25 | 2,4-D | 1:20 | 9:180 |
| X.25 | 2,4-D | 1:6.67 | 9:60 |
| X.25 | 2,4-D | 1:60 | 3:180 |
| X.25 | 2,4-D | 1:20 | 3:60 |
| X.24 | 2,4-D | 1:20 | 9:180 |
| X.01 | Timorex Gold ™ | 1:4500 | 40:180000 |
| X.01 | Timorex Gold ™ | 1:1500 | 120:180000 |
| X.01 | Timorex Gold ™ | 1:1500 | 40:60000 |
| X.01 | Timorex Gold ™ | 1:500 | 120:60000 |
| X.14 | Timorex Gold ™ | 1:4500 | 40:180000 |
| X.14 | Timorex Gold ™ | 1:1500 | 120:180000 |
| X.14 | Timorex Gold ™ | 1:1500 | 40:60000 |
| X.14 | Timorex Gold ™ | 1:500 | 120:60000 |
| X.04 | Timorex Gold ™ | 1:1000 | 9:9000 |
| X.04 | Timorex Gold ™ | 1:500 | 9:4500 |
| X.04 | Timorex Gold ™ | 1:3000 | 3:9000 |
| X.04 | Timorex Gold ™ | 1:1500 | 3:4500 |
| X.07 | Timorex Gold ™ | 1:1000 | 9:9000 |
| X.07 | Timorex Gold ™ | 1:500 | 9:4500 |
| X.07 | Timorex Gold ™ | 1:3000 | 3:9000 |
| X.07 | Timorex Gold ™ | 1:1500 | 3:4500 |
| X.25 | Timorex Gold ™ | 1:1000 | 9:9000 |
| X.25 | Timorex Gold ™ | 1:500 | 9:4500 |
| X.25 | Timorex Gold ™ | 1:3000 | 3:9000 |
| X.25 | Timorex Gold ™ | 1:1500 | 3:4500 |
| X.24 | Timorex Gold ™ | 1:1000 | 9:9000 |
| X.24 | Timorex Gold ™ | 1:500 | 9:4500 |
| X.24 | Timorex Gold ™ | 1:3000 | 3:9000 |
| X.24 | Timorex Gold ™ | 1:1500 | 3:4500 |
| X.14 | Thiamethoxam | 1:250 | 10:2500 |
| X.04 | Thiamethoxam | 1:33.33 | 9:300 |
| X.04 | Thiamethoxam | 1:16.67 | 9:150 |
| X.04 | Thiamethoxam | 1:100 | 3:300 |
| X.04 | Thiamethoxam | 1:50 | 3:150 |
| X.07 | Thiamethoxam | 1:33.33 | 9:300 |
| X.07 | Thiamethoxam | 1:16.67 | 9:150 |
| X.07 | Thiamethoxam | 1:100 | 3:300 |
| X.07 | Thiamethoxam | 1:50 | 3:150 |
| X.25 | Thiamethoxam | 1:33.33 | 9:300 |
| X.25 | Thiamethoxam | 1:16.67 | 9:150 |
| X.25 | Thiamethoxam | 1:100 | 3:300 |
| X.25 | Thiamethoxam | 1:50 | 3:150 |
| X.24 | Thiamethoxam | 1:33.33 | 9:300 |
| X.24 | Thiamethoxam | 1:16.67 | 9:150 |
| X.24 | Thiamethoxam | 1:100 | 3:300 |
| X.24 | Thiamethoxam | 1:50 | 3:150 |

Example B2: *Uncinula Necator*/Grape/Preventive (Powdery Mildew on Grape)→UNCIVIT/fo-pr-P 5-week old grape seedlings cv. Gutedel were treated with the formulated test compounds in a spray chamber. One day after application grape plants were inoculated by shaking plants infected with grape powdery mildew above the test plants. After an incubation period of 7 days at 24/22° C. and 70% r. h. under a light regime of 14/10 h (light/dark) the percentage leaf area covered by disease was assessed.

The following mixture compositions (A:B) at the reported concentration (in ppm) gave at least 80% disease control in this test.

| Component A (Compound) | Component B | Ratio A:B | Conc. (ppm) (A:B) |
|---|---|---|---|
| X.01 | Benzovindiflupyr | 1000:1 | 60:0.06 |
| X.01 | Benzovindiflupyr | 3000:1 | 60:0.02 |
| X.14 | Benzovindiflupyr | 1000:1 | 60:0.06 |
| X.14 | Benzovindiflupyr | 3000:1 | 60:0.02 |
| X.14 | Benzovindiflupyr | 333:1 | 20:0.06 |
| X.14 | Benzovindiflupyr | 1000:1 | 20:0.02 |
| X.04 | Benzovindiflupyr | 1000:1 | 60:0.06 |
| X.04 | Benzovindiflupyr | 3000:1 | 60:0.02 |
| X.04 | Benzovindiflupyr | 333.33:1 | 20:0.06 |
| X.04 | Benzovindiflupyr | 1000:1 | 20:0.02 |
| X.07 | Benzovindiflupyr | 1000:1 | 60:0.06 |
| X.07 | Benzovindiflupyr | 3000:1 | 60:0.02 |
| X.07 | Benzovindiflupyr | 333.33:1 | 20:0.06 |
| X.07 | Benzovindiflupyr | 1000:1 | 20:0.02 |
| X.25 | Benzovindiflupyr | 3:1 | 60:20 |
| X.25 | Benzovindiflupyr | 10:1 | 60:6 |
| X.25 | Benzovindiflupyr | 1:1 | 20:20 |
| X.25 | Benzovindiflupyr | 3.3:1 | 20:6 |
| X.24 | Benzovindiflupyr | 3:1 | 60:20 |
| X.24 | Benzovindiflupyr | 10:1 | 60:6 |
| X.24 | Benzovindiflupyr | 1:1 | 20:20 |
| X.24 | Benzovindiflupyr | 3.3:1 | 20:6 |
| X.01 | Isopyrazam | 10:1 | 60:6 |

| Component A (Compound) | Component B | Ratio A:B | Conc. (ppm) (A:B) |
|---|---|---|---|
| X.01 | Isopyrazam | 30:1 | 60:2 |
| X.01 | Isopyrazam | 3.3:1 | 20:6 |
| X.01 | Isopyrazam | 10:1 | 20:2 |
| X.14 | Isopyrazam | 1:1 | 6:6 |
| X.14 | Isopyrazam | 3:1 | 6:2 |
| X.14 | Isopyrazam | 1:3 | 2:6 |
| X.14 | Isopyrazam | 1:1 | 2:2 |
| X.01 | Penthiopyrad | 10:1 | 60:6 |
| X.01 | Penthiopyrad | 30:1 | 60:2 |
| X.01 | Penthiopyrad | 3.3:1 | 20:6 |
| X.14 | Penthiopyrad | 1:1 | 6:6 |
| X.14 | Penthiopyrad | 3:1 | 6:2 |
| X.14 | Penthiopyrad | 1:3 | 2:6 |
| X.01 | Pydiflumetofen | 10:1 | 60:6 |
| X.01 | Pydiflumetofen | 30:1 | 60:2 |
| X.01 | Pydiflumetofen | 3.3:1 | 20:6 |
| X.01 | Pydiflumetofen | 10:1 | 20:2 |
| X.14 | Pydiflumetofen | 10:1 | 60:6 |
| X.14 | Pydiflumetofen | 30:1 | 60:2 |
| X.14 | Pydiflumetofen | 3.3:1 | 20:6 |
| X.14 | Pydiflumetofen | 10:1 | 20:2 |
| X.04 | Pydiflumetofen | 10:1 | 60:6 |
| X.04 | Pydiflumetofen | 30:1 | 60:2 |
| X.04 | Pydiflumetofen | 3.33:1 | 20:6 |
| X.04 | Pydiflumetofen | 10:1 | 20:2 |
| X.07 | Pydiflumetofen | 10:1 | 60:6 |
| X.07 | Pydiflumetofen | 30:1 | 60:2 |
| X.07 | Pydiflumetofen | 3.33:1 | 20:6 |
| X.07 | Pydiflumetofen | 10:1 | 20:2 |
| X.25 | Pydiflumetofen | 3:1 | 60:20 |
| X.25 | Pydiflumetofen | 10:1 | 60:6 |
| X.25 | Pydiflumetofen | 1:1 | 20:20 |
| X.25 | Pydiflumetofen | 3.3:1 | 20:6 |
| X.24 | Pydiflumetofen | 3:1 | 60:20 |
| X.24 | Pydiflumetofen | 10:1 | 60:6 |
| X.24 | Pydiflumetofen | 1:1 | 20:20 |
| X.24 | Pydiflumetofen | 3.3:1 | 20:6 |
| X.01 | Fluopyram | 10:1 | 60:6 |
| X.01 | Fluopyram | 30:1 | 60:2 |
| X.14 | Fluopyram | 10:1 | 60:6 |
| X.14 | Fluopyram | 30:1 | 60:2 |
| X.14 | Fluopyram | 3.3:1 | 20:6 |
| X.14 | Fluopyram | 10:1 | 20:2 |
| X.04 | Fluopyram | 10:1 | 60:6 |
| X.04 | Fluopyram | 30:1 | 60:2 |
| X.04 | Fluopyram | 3.33:1 | 20:6 |
| X.04 | Fluopyram | 10:1 | 20:2 |
| X.07 | Fluopyram | 10:1 | 60:6 |
| X.07 | Fluopyram | 30:1 | 60:2 |
| X.07 | Fluopyram | 3.33:1 | 20:6 |
| X.07 | Fluopyram | 10:1 | 20:2 |
| X.25 | Fluopyram | 3:1 | 60:20 |
| X.25 | Fluopyram | 10:1 | 60:6 |
| X.25 | Fluopyram | 1:1 | 20:20 |
| X.25 | Fluopyram | 3.3:1 | 20:6 |
| X.24 | Fluopyram | 3:1 | 60:20 |
| X.24 | Fluopyram | 10:1 | 60:6 |
| X.24 | Fluopyram | 1:1 | 20:20 |
| X.24 | Fluopyram | 3.3:1 | 20:6 |
| X.01 | Azoxystrobin | 1000:1 | 60:0.06 |
| X.01 | Azoxystrobin | 3000:1 | 60:0.02 |
| X.01 | Azoxystrobin | 333:1 | 20:0.06 |
| X.14 | Azoxystrobin | 1000:1 | 60:0.06 |
| X.14 | Azoxystrobin | 3000:1 | 60:0.02 |
| X.14 | Azoxystrobin | 333:1 | 20:0.06 |
| X.14 | Azoxystrobin | 1000:1 | 20:0.02 |
| X.04 | Azoxystrobin | 1000:1 | 60:0.06 |
| X.04 | Azoxystrobin | 3000:1 | 60:0.02 |
| X.04 | Azoxystrobin | 333.33:1 | 20:0.06 |
| X.04 | Azoxystrobin | 1000:1 | 20:0.02 |
| X.07 | Azoxystrobin | 1000:1 | 60:0.06 |
| X.07 | Azoxystrobin | 3000:1 | 60:0.02 |
| X.07 | Azoxystrobin | 333.33:1 | 20:0.06 |
| X.07 | Azoxystrobin | 1000:1 | 20:0.02 |
| X.25 | Azoxystrobin | 100:1 | 60:0.6 |
| X.25 | Azoxystrobin | 300:1 | 60:0.2 |
| X.25 | Azoxystrobin | 33.33:1 | 20:0.6 |
| X.25 | Azoxystrobin | 100:1 | 20:0.2 |
| X.24 | Azoxystrobin | 100:1 | 60:0.6 |
| X.24 | Azoxystrobin | 300:1 | 60:0.2 |
| X.24 | Azoxystrobin | 33.33:1 | 20:0.6 |
| X.24 | Azoxystrobin | 100:1 | 20:0.2 |
| X.01 | Trifloxystrobin | 1000:1 | 60:0.06 |
| X.01 | Trifloxystrobin | 3000:1 | 60:0.02 |
| X.01 | Trifloxystrobin | 333:1 | 20:0.06 |
| X.01 | Trifloxystrobin | 1000:1 | 20:0.02 |
| X.14 | Trifloxystrobin | 1000:1 | 60:0.06 |
| X.14 | Trifloxystrobin | 3000:1 | 60:0.02 |
| X.14 | Trifloxystrobin | 333:1 | 20:0.06 |
| X.14 | Trifloxystrobin | 1000:1 | 20:0.02 |
| X.04 | Trifloxystrobin | 1000:1 | 60:0.06 |
| X.04 | Trifloxystrobin | 3000:1 | 60:0.02 |
| X.04 | Trifloxystrobin | 333.33:1 | 20:0.06 |
| X.04 | Trifloxystrobin | 1000:1 | 20:0.02 |
| X.07 | Trifloxystrobin | 1000:1 | 60:0.06 |
| X.07 | Trifloxystrobin | 3000:1 | 60:0.02 |
| X.07 | Trifloxystrobin | 333.33:1 | 20:0.06 |
| X.07 | Trifloxystrobin | 1000:1 | 20:0.02 |
| X.25 | Trifloxystrobin | 100:1 | 60:0.6 |
| X.25 | Trifloxystrobin | 300:1 | 60:0.2 |
| X.25 | Trifloxystrobin | 33.33:1 | 20:0.6 |
| X.25 | Trifloxystrobin | 100:1 | 20:0.2 |
| X.24 | Trifloxystrobin | 100:1 | 60:0.6 |
| X.24 | Trifloxystrobin | 300:1 | 60:0.2 |
| X.24 | Trifloxystrobin | 33.33:1 | 20:0.6 |
| X.24 | Trifloxystrobin | 100:1 | 20:0.2 |
| X.01 | Pyraclostrobin | 100:1 | 60:0.6 |
| X.01 | Pyraclostrobin | 300:1 | 60:0.2 |
| X.01 | Pyraclostrobin | 33:1 | 20:0.6 |
| X.01 | Pyraclostrobin | 100:1 | 20:0.2 |
| X.14 | Pyraclostrobin | 10:1 | 6:0.6 |
| X.14 | Pyraclostrobin | 30:1 | 6:0.2 |
| X.14 | Pyraclostrobin | 3.3:1 | 2:0.6 |
| X.14 | Pyraclostrobin | 10:1 | 2:0.2 |
| X.04 | Pyraclostrobin | 100:1 | 60:0.6 |
| X.04 | Pyraclostrobin | 300:1 | 60:0.2 |
| X.04 | Pyraclostrobin | 33.33:1 | 20:0.6 |
| X.04 | Pyraclostrobin | 100:1 | 20:0.2 |
| X.07 | Pyraclostrobin | 100:1 | 60:0.6 |
| X.07 | Pyraclostrobin | 300:1 | 60:0.2 |
| X.07 | Pyraclostrobin | 33.33:1 | 20:0.6 |
| X.07 | Pyraclostrobin | 100:1 | 20:0.2 |
| X.25 | Pyraclostrobin | 100:1 | 60:0.6 |
| X.25 | Pyraclostrobin | 300:1 | 60:0.2 |
| X.25 | Pyraclostrobin | 33.33:1 | 20:0.6 |
| X.25 | Pyraclostrobin | 100:1 | 20:0.2 |
| X.24 | Pyraclostrobin | 100:1 | 60:0.6 |
| X.24 | Pyraclostrobin | 300:1 | 60:0.2 |
| X.24 | Pyraclostrobin | 33.33:1 | 20:0.6 |
| X.24 | Pyraclostrobin | 100:1 | 20:0.2 |
| X.01 | Cyproconazole | 100:1 | 60:0.6 |
| X.01 | Cyproconazole | 300:1 | 60:0.2 |
| X.01 | Cyproconazole | 33.3:1 | 20:0.6 |
| X.14 | Cyproconazole | 100:1 | 60:0.6 |
| X.14 | Cyproconazole | 300:1 | 60:0.2 |
| X.14 | Cyproconazole | 33.3:1 | 20:0.6 |
| X.14 | Cyproconazole | 100:1 | 20:0.2 |
| X.04 | Cyproconazole | 100:1 | 60:0.6 |
| X.04 | Cyproconazole | 300:1 | 60:0.2 |
| X.04 | Cyproconazole | 33.33:1 | 20:0.6 |
| X.04 | Cyproconazole | 100:1 | 20:0.2 |
| X.07 | Cyproconazole | 100:1 | 60:0.6 |
| X.07 | Cyproconazole | 300:1 | 60:0.2 |
| X.07 | Cyproconazole | 33.33:1 | 20:0.6 |
| X.07 | Cyproconazole | 100:1 | 20:0.2 |
| X.25 | Cyproconazole | 10:1 | 60:6 |
| X.25 | Cyproconazole | 30:1 | 60:2 |
| X.25 | Cyproconazole | 3.33:1 | 20:6 |
| X.25 | Cyproconazole | 10:1 | 20:2 |
| X.24 | Cyproconazole | 10:1 | 60:6 |
| X.24 | Cyproconazole | 30:1 | 60:2 |
| X.24 | Cyproconazole | 3.33:1 | 20:6 |

| Component A (Compound) | Component B | Ratio A:B | Conc. (ppm) (A:B) |
|---|---|---|---|
| X.24 | Cyproconazole | 10:1 | 20:2 |
| X.01 | Difenoconazole | 10:1 | 60:6 |
| X.01 | Difenoconazole | 30:1 | 60:2 |
| X.01 | Difenoconazole | 3.3:1 | 20:6 |
| X.01 | Difenoconazole | 10:1 | 20:2 |
| X.14 | Difenoconazole | 1:1 | 6:6 |
| X.14 | Difenoconazole | 3:1 | 6:2 |
| X.14 | Difenoconazole | 1:3 | 2:6 |
| X.14 | Difenoconazole | 1:1 | 2:2 |
| X.04 | Difenoconazole | 10:1 | 60:6 |
| X.04 | Difenoconazole | 30:1 | 60:2 |
| X.04 | Difenoconazole | 3.33:1 | 20:6 |
| X.04 | Difenoconazole | 10:1 | 20:2 |
| X.07 | Difenoconazole | 10:1 | 60:6 |
| X.07 | Difenoconazole | 30:1 | 60:2 |
| X.07 | Difenoconazole | 3.33:1 | 20:6 |
| X.07 | Difenoconazole | 10:1 | 20:2 |
| X.25 | Difenoconazole | 10:1 | 60:6 |
| X.25 | Difenoconazole | 30:1 | 60:2 |
| X.25 | Difenoconazole | 3.33:1 | 20:6 |
| X.25 | Difenoconazole | 10:1 | 20:2 |
| X.24 | Difenoconazole | 10:1 | 60:6 |
| X.24 | Difenoconazole | 30:1 | 60:2 |
| X.24 | Difenoconazole | 3.33:1 | 20:6 |
| X.24 | Difenoconazole | 10:1 | 20:2 |
| X.01 | Hexaconazole | 10:1 | 60:6 |
| X.01 | Hexaconazole | 30:1 | 60:2 |
| X.01 | Hexaconazole | 3.3:1 | 20:6 |
| X.01 | Hexaconazole | 10:1 | 20:2 |
| X.14 | Hexaconazole | 1:1 | 6:6 |
| X.14 | Hexaconazole | 3:1 | 6:2 |
| X.14 | Hexaconazole | 1:3 | 2:6 |
| X.14 | Hexaconazole | 1:1 | 2:2 |
| X.04 | Hexaconazole | 10:1 | 60:6 |
| X.04 | Hexaconazole | 30:1 | 60:2 |
| X.04 | Hexaconazole | 3.33:1 | 20:6 |
| X.04 | Hexaconazole | 10:1 | 20:2 |
| X.07 | Hexaconazole | 10:1 | 60:6 |
| X.07 | Hexaconazole | 30:1 | 60:2 |
| X.07 | Hexaconazole | 3.33:1 | 20:6 |
| X.07 | Hexaconazole | 10:1 | 20:2 |
| X.25 | Hexaconazole | 10:1 | 60:6 |
| X.25 | Hexaconazole | 30:1 | 60:2 |
| X.25 | Hexaconazole | 3.33:1 | 20:6 |
| X.25 | Hexaconazole | 10:1 | 20:2 |
| X.24 | Hexaconazole | 10:1 | 60:6 |
| X.24 | Hexaconazole | 30:1 | 60:2 |
| X.24 | Hexaconazole | 3.33:1 | 20:6 |
| X.24 | Hexaconazole | 10:1 | 20:2 |
| X.01 | Propiconazole | 10:1 | 60:6 |
| X.01 | Propiconazole | 30:1 | 60:2 |
| X.01 | Propiconazole | 3.3:1 | 20:6 |
| X.01 | Propiconazole | 10:1 | 20:2 |
| X.14 | Propiconazole | 1:1 | 6:6 |
| X.14 | Propiconazole | 3:1 | 6:2 |
| X.14 | Propiconazole | 1:3 | 2:6 |
| X.14 | Propiconazole | 1:1 | 2:2 |
| X.01 | Mefentrifluconazole | 10:1 | 60:6 |
| X.01 | Mefentrifluconazole | 30:1 | 60:2 |
| X.01 | Mefentrifluconazole | 3.3:1 | 20:6 |
| X.01 | Mefentrifluconazole | 10:1 | 20:2 |
| X.14 | Mefentrifluconazole | 1:1 | 6:6 |
| X.14 | Mefentrifluconazole | 3:1 | 6:2 |
| X.14 | Mefentrifluconazole | 1:3 | 2:6 |
| X.14 | Mefentrifluconazole | 1:1 | 2:2 |
| X.04 | Mefentrifluconazole | 10:1 | 60:6 |
| X.04 | Mefentrifluconazole | 30:1 | 60:2 |
| X.04 | Mefentrifluconazole | 3.33:1 | 20:6 |
| X.04 | Mefentrifluconazole | 10:1 | 20:2 |
| X.07 | Mefentrifluconazole | 10:1 | 60:6 |
| X.07 | Mefentrifluconazole | 30:1 | 60:2 |
| X.07 | Mefentrifluconazole | 3.33:1 | 20:6 |
| X.07 | Mefentrifluconazole | 10:1 | 20:2 |
| X.25 | Mefentrifluconazole | 10:1 | 60:6 |
| X.25 | Mefentrifluconazole | 30:1 | 60:2 |
| X.25 | Mefentrifluconazole | 3.33:1 | 20:6 |
| X.25 | Mefentrifluconazole | 10:1 | 20:2 |
| X.24 | Mefentrifluconazole | 10:1 | 60:6 |
| X.24 | Mefentrifluconazole | 30:1 | 60:2 |
| X.24 | Mefentrifluconazole | 3.33:1 | 20:6 |
| X.24 | Mefentrifluconazole | 10:1 | 20:2 |
| X.01 | Prothioconazole | 10:1 | 60:6 |
| X.01 | Prothioconazole | 30:1 | 60:2 |
| X.01 | Prothioconazole | 3.3:1 | 20:6 |
| X.14 | Prothioconazole | 10:1 | 60:6 |
| X.14 | Prothioconazole | 30:1 | 60:2 |
| X.14 | Prothioconazole | 3.3:1 | 20:6 |
| X.14 | Prothioconazole | 10:1 | 20:2 |
| X.04 | Prothioconazole | 10:1 | 60:6 |
| X.04 | Prothioconazole | 30:1 | 60:2 |
| X.04 | Prothioconazole | 3.33:1 | 20:6 |
| X.04 | Prothioconazole | 10:1 | 20:2 |
| X.07 | Prothioconazole | 10:1 | 60:6 |
| X.07 | Prothioconazole | 30:1 | 60:2 |
| X.07 | Prothioconazole | 3.33:1 | 20:6 |
| X.07 | Prothioconazole | 10:1 | 20:2 |
| X.25 | Prothioconazole | 10:1 | 60:6 |
| X.25 | Prothioconazole | 30:1 | 60:2 |
| X.25 | Prothioconazole | 3.33:1 | 20:6 |
| X.25 | Prothioconazole | 10:1 | 20:2 |
| X.24 | Prothioconazole | 10:1 | 60:6 |
| X.24 | Prothioconazole | 30:1 | 60:2 |
| X.24 | Prothioconazole | 3.33:1 | 20:6 |
| X.24 | Prothioconazole | 10:1 | 20:2 |
| X.01 | Chlorothalonil | 1:1 | 60:60 |
| X.01 | Chlorothalonil | 3:1 | 60:20 |
| X.01 | Chlorothalonil | 1:3 | 20:60 |
| X.01 | Chlorothalonil | 1:1 | 20:20 |
| X.14 | Chlorothalonil | 1:1 | 60:60 |
| X.14 | Chlorothalonil | 3:1 | 60:20 |
| X.14 | Chlorothalonil | 1:3 | 20:60 |
| X.14 | Chlorothalonil | 1:1 | 20:20 |
| X.04 | Chlorothalonil | 1:1 | 60:60 |
| X.04 | Chlorothalonil | 3:1 | 60:20 |
| X.04 | Chlorothalonil | 1:3 | 20:60 |
| X.07 | Chlorothalonil | 1:1 | 60:60 |
| X.07 | Chlorothalonil | 3:1 | 60:20 |
| X.07 | Chlorothalonil | 1:3 | 20:60 |
| X.07 | Chlorothalonil | 1:1 | 20:20 |
| X.25 | Chlorothalonil | 1:1 | 60:60 |
| X.25 | Chlorothalonil | 3:1 | 60:20 |
| X.25 | Chlorothalonil | 1:3 | 20:60 |
| X.25 | Chlorothalonil | 1:1 | 20:20 |
| X.24 | Chlorothalonil | 1:1 | 60:60 |
| X.24 | Chlorothalonil | 3:1 | 60:20 |
| X.24 | Chlorothalonil | 1:3 | 20:60 |
| X.24 | Chlorothalonil | 1:1 | 20:20 |
| X.01 | Mancozeb | 1:1 | 60:60 |
| X.01 | Mancozeb | 3:1 | 60:20 |
| X.14 | Mancozeb | 1:1 | 60:60 |
| X.14 | Mancozeb | 3:1 | 60:20 |
| X.14 | Mancozeb | 1:3 | 20:60 |
| X.14 | Mancozeb | 1:1 | 20:20 |
| X.04 | Mancozeb | 1:1 | 60:60 |
| X.04 | Mancozeb | 3:1 | 60:20 |
| X.04 | Mancozeb | 1:3 | 20:60 |
| X.04 | Mancozeb | 1:1 | 20:20 |
| X.07 | Mancozeb | 1:1 | 60:60 |
| X.07 | Mancozeb | 3:1 | 60:20 |
| X.07 | Mancozeb | 1:3 | 20:60 |
| X.07 | Mancozeb | 1:1 | 20:20 |
| X.25 | Mancozeb | 1:1 | 60:60 |
| X.25 | Mancozeb | 3:1 | 60:20 |
| X.25 | Mancozeb | 1:3 | 20:60 |
| X.25 | Mancozeb | 1:1 | 20:20 |
| X.24 | Mancozeb | 1:1 | 60:60 |
| X.24 | Mancozeb | 3:1 | 60:20 |
| X.24 | Mancozeb | 1:3 | 20:60 |
| X.24 | Mancozeb | 1:1 | 20:20 |
| X.01 | fosetyl-aluminium | 1:3.3 | 60:200 |
| X.01 | fosetyl-aluminium | 1:1 | 60:60 |
| X.14 | fosetyl-aluminium | 1:33 | 6:200 |

| Component A (Compound) | Component B | Ratio A:B | Conc. (ppm) (A:B) |
|---|---|---|---|
| X.14 | fosetyl-aluminium | 1:10 | 6:60 |
| X.01 | Acibenzolar-S-methyl | 1:3.3 | 60:200 |
| X.01 | Acibenzolar-S-methyl | 1:1 | 60:60 |
| X.01 | Acibenzolar-S-methyl | 1:10 | 20:200 |
| X.14 | Acibenzolar-S-methyl | 1:33.3 | 6:200 |
| X.14 | Acibenzolar-S-methyl | 1:10 | 6:60 |
| X.14 | Acibenzolar-S-methyl | 1:100 | 2:200 |
| X.14 | Acibenzolar-S-methyl | 1:30 | 2:60 |
| X.04 | Acibenzolar-S-methyl | 1:3.3 | 60:200 |
| X.04 | Acibenzolar-S-methyl | 1:1 | 60:60 |
| X.04 | Acibenzolar-S-methyl | 1:3.3 | 20:60 |
| X.07 | Acibenzolar-S-methyl | 1:3.3 | 60:200 |
| X.07 | Acibenzolar-S-methyl | 1:1 | 60:60 |
| X.07 | Acibenzolar-S-methyl | 1:10 | 20:200 |
| X.07 | Acibenzolar-S-methyl | 1:3.3 | 20:60 |
| X.25 | Acibenzolar-S-methyl | 1:3.3 | 60:200 |
| X.25 | Acibenzolar-S-methyl | 1:1 | 60:60 |
| X.25 | Acibenzolar-S-methyl | 1:10 | 20:200 |
| X.25 | Acibenzolar-S-methyl | 1:3.3 | 20:60 |
| X.24 | Acibenzolar-S-methyl | 1:3.3 | 60:200 |
| X.24 | Acibenzolar-S-methyl | 1:1 | 60:60 |
| X.24 | Acibenzolar-S-methyl | 1:10 | 20:200 |
| X.24 | Acibenzolar-S-methyl | 1:3.3 | 20:60 |

Example B3: *Glomerella Lagenarium* (*Colletotrichum Lagenarium*)/Cucumber/Preventive→COLL-CUM/fo-pr-S 1-week old cucumber plants cv. Wisconsin were treated with the formulated test compounds in a spray chamber. One day after application wheat plants were inoculated by spraying a spore suspension (1×10$^5$ spores/ml) on the test plants. After an incubation period of 30 h in darkness at 23° C. and 100% r. h. plants were kept for 6 days 23° C./21° C. (day/night) and 70% r.h. in a greenhouse. The percentage leaf area covered by disease was assessed 7 days after inoculation.

The following mixture compositions (A:B) at the reported concentration (in ppm) gave at least 80% disease control in this test.

| Component A (Compound) | Component B | Ratio A:B | Conc. (ppm) (A:B) |
|---|---|---|---|
| X.01 | Benzovindiflupyr | 1000:1 | 60:0.06 |
| X.01 | Benzovindiflupyr | 3000:1 | 60:0.02 |
| X.14 | Benzovindiflupyr | 1000:1 | 60:0.06 |
| X.14 | Benzovindiflupyr | 3000:1 | 60:0.02 |
| X.25 | Benzovindiflupyr | 3:1 | 60:20 |
| X.25 | Benzovindiflupyr | 10:1 | 60:6 |
| X.25 | Benzovindiflupyr | 1:1 | 20:20 |
| X.24 | Benzovindiflupyr | 3:1 | 60:20 |
| X.24 | Benzovindiflupyr | 10:1 | 60:6 |
| X.24 | Benzovindiflupyr | 1:1 | 20:20 |
| X.24 | Benzovindiflupyr | 3.3:1 | 20:6 |
| X.01 | Isopyrazam | 10:1 | 60:6 |
| X.01 | Isopyrazam | 30:1 | 60:2 |
| X.14 | Isopyrazam | 1:1 | 6:6 |
| X.14 | Isopyrazam | 3:1 | 6:2 |
| X.14 | Isopyrazam | 1:3 | 2:6 |
| X.01 | Penthiopyrad | 10:1 | 60:6 |
| X.01 | Penthiopyrad | 30:1 | 60:2 |
| X.14 | Penthiopyrad | 1:1 | 6:6 |
| X.14 | Penthiopyrad | 3:1 | 6:2 |
| X.14 | Penthiopyrad | 1:3 | 2:6 |
| X.01 | Pydiflumetofen | 10:1 | 60:6 |
| X.01 | Pydiflumetofen | 30:1 | 60:2 |
| X.14 | Pydiflumetofen | 10:1 | 60:6 |
| X.25 | Pydiflumetofen | 10:1 | 60:6 |
| X.24 | Pydiflumetofen | 3:1 | 60:20 |
| X.24 | Pydiflumetofen | 10:1 | 60:6 |
| X.01 | Fluopyram | 10:1 | 60:6 |
| X.01 | Fluopyram | 30:1 | 60:2 |
| X.14 | Fluopyram | 10:1 | 60:6 |
| X.14 | Fluopyram | 30:1 | 60:2 |
| X.25 | Fluopyram | 3:1 | 60:20 |
| X.25 | Fluopyram | 10:1 | 60:6 |
| X.24 | Fluopyram | 3:1 | 60:20 |
| X.24 | Fluopyram | 10:1 | 60:6 |
| X.24 | Fluopyram | 1:1 | 20:20 |
| X.01 | Azoxystrobin | 1000:1 | 60:0.06 |
| X.14 | Azoxystrobin | 1000:1 | 60:0.06 |
| X.07 | Azoxystrobin | 1000:1 | 60:0.06 |
| X.25 | Azoxystrobin | 100:1 | 60:0.6 |
| X.25 | Azoxystrobin | 300:1 | 60:0.2 |
| X.25 | Azoxystrobin | 33.33:1 | 20:0.6 |
| X.25 | Azoxystrobin | 100:1 | 20:0.2 |
| X.24 | Azoxystrobin | 100:1 | 60:0.6 |
| X.24 | Azoxystrobin | 300:1 | 60:0.2 |
| X.24 | Azoxystrobin | 33.33:1 | 20:0.6 |
| X.24 | Azoxystrobin | 100:1 | 20:0.2 |
| X.01 | Trifloxystrobin | 1000:1 | 60:0.06 |
| X.14 | Trifloxystrobin | 1000:1 | 60:0.06 |
| X.14 | Trifloxystrobin | 3000:1 | 60:0.02 |
| X.25 | Trifloxystrobin | 100:1 | 60:0.6 |
| X.24 | Trifloxystrobin | 300:1 | 60:0.2 |
| X.24 | Trifloxystrobin | 100:1 | 60:0.6 |
| X.01 | Pyraclostrobin | 100:1 | 60:0.6 |
| X.01 | Pyraclostrobin | 300:1 | 60:0.2 |
| X.01 | Pyraclostrobin | 33:1 | 20:0.6 |
| X.01 | Pyraclostrobin | 100:1 | 20:0.2 |
| X.14 | Pyraclostrobin | 10:1 | 6:0.6 |
| X.14 | Pyraclostrobin | 30:1 | 6:0.2 |
| X.14 | Pyraclostrobin | 3.3:1 | 2:0.6 |
| X.14 | Pyraclostrobin | 10:1 | 2:0.2 |
| X.25 | Pyraclostrobin | 100:1 | 60:0.6 |
| X.25 | Pyraclostrobin | 300:1 | 60:0.2 |
| X.24 | Pyraclostrobin | 100:1 | 60:0.6 |
| X.24 | Pyraclostrobin | 300:1 | 60:0.2 |
| X.01 | Cyproconazole | 100:1 | 60:0.6 |
| X.01 | Cyproconazole | 300:1 | 60:0.2 |
| X.14 | Cyproconazole | 100:1 | 60:0.6 |
| X.14 | Cyproconazole | 300:1 | 60:0.2 |
| X.25 | Cyproconazole | 100:1 | 60:0.6 |
| X.25 | Cyproconazole | 300:1 | 60:0.2 |
| X.24 | Cyproconazole | 100:1 | 60:0.6 |
| X.24 | Cyproconazole | 300:1 | 60:0.2 |
| X.01 | Difenoconazole | 10:1 | 60:6 |
| X.01 | Difenoconazole | 30:1 | 60:2 |
| X.01 | Difenoconazole | 3.3:1 | 20:6 |
| X.14 | Difenoconazole | 1:1 | 6:6 |
| X.24 | Difenoconazole | 10:1 | 60:6 |
| X.24 | Difenoconazole | 30:1 | 60:2 |
| X.01 | Hexaconazole | 10:1 | 60:6 |
| X.01 | Hexaconazole | 30:1 | 60:2 |
| X.01 | Hexaconazole | 3.3:1 | 20:6 |
| X.25 | Hexaconazole | 10:1 | 60:6 |
| X.24 | Hexaconazole | 10:1 | 60:6 |
| X.24 | Hexaconazole | 30:1 | 60:2 |
| X.01 | Propiconazole | 10:1 | 60:6 |
| X.01 | Propiconazole | 30:1 | 60:2 |
| X.25 | Mefentrifluconazole | 30:1 | 60:2 |
| X.24 | Mefentrifluconazole | 10:1 | 60:6 |
| X.24 | Mefentrifluconazole | 30:1 | 60:2 |
| X.14 | Prothioconazole | 10:1 | 60:6 |
| X.14 | Prothioconazole | 30:1 | 60:2 |
| X.14 | Prothioconazole | 3.3:1 | 20:6 |
| X.25 | Prothioconazole | 30:1 | 60:2 |
| X.24 | Prothioconazole | 10:1 | 60:6 |
| X.24 | Prothioconazole | 30:1 | 60:2 |
| X.01 | Chlorothalonil | 1:1 | 60:60 |
| X.01 | Chlorothalonil | 3:1 | 60:20 |
| X.01 | Chlorothalonil | 1:3 | 20:60 |
| X.01 | Chlorothalonil | 1:1 | 20:20 |
| X.14 | Chlorothalonil | 1:1 | 60:60 |

-continued

| Component A (Compound) | Component B | Ratio A:B | Conc. (ppm) (A:B) |
|---|---|---|---|
| X.14 | Chlorothalonil | 3:1 | 60:20 |
| X.14 | Chlorothalonil | 1:3 | 20:60 |
| X.04 | Chlorothalonil | 60:60 | 60:60 |
| X.04 | Chlorothalonil | 60:20 | 60:20 |
| X.07 | Chlorothalonil | 60:60 | 60:60 |
| X.25 | Chlorothalonil | 1:1 | 60:60 |
| X.25 | Chlorothalonil | 3:1 | 60:20 |
| X.25 | Chlorothalonil | 1:3 | 20:60 |
| X.24 | Chlorothalonil | 1:1 | 60:60 |
| X.24 | Chlorothalonil | 3:1 | 60:20 |
| X.24 | Chlorothalonil | 1:3 | 20:60 |
| X.24 | Chlorothalonil | 1:1 | 20:20 |
| X.01 | Mancozeb | 1:1 | 60:60 |
| X.01 | Mancozeb | 3:1 | 60:20 |
| X.01 | Mancozeb | 1:3 | 20:60 |
| X.01 | Mancozeb | 1:1 | 20:20 |
| X.14 | Mancozeb | 1:1 | 60:60 |
| X.14 | Mancozeb | 3:1 | 60:20 |
| X.14 | Mancozeb | 1:3 | 20:60 |
| X.14 | Mancozeb | 1:1 | 20:20 |
| X.04 | Mancozeb | 1:1 | 60:60 |
| X.04 | Mancozeb | 3:1 | 60:20 |
| X.04 | Mancozeb | 1:3 | 20:60 |
| X.04 | Mancozeb | 1:1 | 20:20 |
| X.07 | Mancozeb | 1:1 | 60:60 |
| X.07 | Mancozeb | 3:1 | 60:20 |
| X.07 | Mancozeb | 1:3 | 20:60 |
| X.07 | Mancozeb | 1:1 | 20:20 |
| X.25 | Mancozeb | 1:1 | 60:60 |
| X.25 | Mancozeb | 3:1 | 60:20 |
| X.25 | Mancozeb | 1:3 | 20:60 |
| X.25 | Mancozeb | 1:1 | 20:20 |
| X.24 | Mancozeb | 1:1 | 60:60 |
| X.24 | Mancozeb | 3:1 | 60:20 |
| X.24 | Mancozeb | 1:3 | 20:60 |
| X.24 | Mancozeb | 1:1 | 20:20 |
| X.01 | fosetyl-aluminium | 1:3.3 | 60:200 |
| X.01 | fosetyl-aluminium | 1:1 | 60:60 |
| X.01 | fosetyl-aluminium | 1:10 | 20:200 |
| X.14 | fosetyl-aluminium | 1:3.3 | 60:200 |
| X.14 | fosetyl-aluminium | 1:1 | 60:60 |
| X.14 | fosetyl-aluminium | 1:10 | 20:200 |
| X.01 | Acibenzolar-S-methyl | 1:3.3 | 60:200 |
| X.01 | Acibenzolar-S-methyl | 1:1 | 60:60 |
| X.01 | Acibenzolar-S-methyl | 1:10 | 20:200 |
| X.01 | Acibenzolar-s-methyl | 1:3 | 20:60 |
| X.14 | Acibenzolar-S-methyl | 1:33.3 | 6:200 |
| X.14 | Acibenzolar-S-methyl | 1:10 | 6:60 |
| X.14 | Acibenzolar-S-methyl | 1:100 | 2:200 |
| X.14 | Acibenzolar-S-methyl | 1:30 | 2:60 |
| X.04 | Acibenzolar-S-methyl | 1:3.3 | 60:200 |
| X.04 | Acibenzolar-S-methyl | 1:1 | 60:60 |
| X.04 | Acibenzolar-S-methyl | 1:10 | 20:200 |
| X.04 | Acibenzolar-s-methyl | 1:3.3 | 20:60 |
| X.07 | Acibenzolar-S-methyl | 1:3.3 | 60:200 |
| X.07 | Acibenzolar-S-methyl | 1:1 | 60:60 |
| X.07 | Acibenzolar-S-methyl | 1:10 | 20:200 |
| X.07 | Acibenzolar-S-methyl | 1:3.3 | 20:60 |
| X.25 | Acibenzolar-S-methyl | 1:3.3 | 60:200 |
| X.25 | Acibenzolar-S-methyl | 1:1 | 60:60 |
| X.25 | Acibenzolar-S-methyl | 1:10 | 20:200 |
| X.25 | Acibenzolar-S-methyl | 1:3.3 | 20:60 |
| X.24 | Acibenzolar-S-methyl | 1:3.3 | 60:200 |
| X.24 | Acibenzolar-S-methyl | 1:1 | 60:60 |
| X.24 | Acibenzolar-S-methyl | 1:10 | 20:200 |
| X.24 | Acibenzolar-S-methyl | 1:3.3 | 20:60 |

Example B4: *Puccinia recondita*/Wheat/Preventive (Brown Rust on Wheat)→PUCCTRZ/fo-pr-P+PUCCTRZ/fo-pr-S 13-day old wheat plants cv. Arina were treated with the formulated test compounds in a spray chamber. One day after application wheat plants were inoculated by spraying a spore suspension ($1\times10^5$ uredospores/ml) on the test plants. After an incubation period of 1 day at 20° C. and 95% r. h. plants were kept for 10 days 20° C./18° C. (day/night) and 60% r.h. in a greenhouse. The percentage leaf area covered by disease was assessed 11 days after inoculation.

The following mixture compositions (A:B) at the reported concentration (in ppm) gave at least 80% disease control in this test.

| Component A (Compound) | Component B | Ratio A:B | Conc. (ppm) (A:B) |
|---|---|---|---|
| X.01 | Benzovindiflupyr | 1000:1 | 60:0.06 |
| X.01 | Benzovindiflupyr | 3000:1 | 60:0.02 |
| X.14 | Benzovindiflupyr | 1000:1 | 60:0.06 |
| X.14 | Benzovindiflupyr | 3000:1 | 60:0.02 |
| X.04 | Benzovindiflupyr | 1000:1 | 60:0.06 |
| X.25 | Benzovindiflupyr | 3:1 | 60:20 |
| X.25 | Benzovindiflupyr | 10:1 | 60:6 |
| X.25 | Benzovindiflupyr | 1:1 | 20:20 |
| X.24 | Benzovindiflupyr | 3:1 | 60:20 |
| X.24 | Benzovindiflupyr | 10:1 | 60:6 |
| X.24 | Benzovindiflupyr | 1:1 | 20:20 |
| X.24 | Benzovindiflupyr | 3.3:1 | 20:6 |
| X.01 | Isopyrazam | 10:1 | 60:6 |
| X.01 | Isopyrazam | 30:1 | 60:2 |
| X.01 | Isopyrazam | 3.3:1 | 20:6 |
| X.01 | Isopyrazam | 10:1 | 20:2 |
| X.14 | Isopyrazam | 1:1 | 6:6 |
| X.14 | Isopyrazam | 3:1 | 6:2 |
| X.14 | Isopyrazam | 1:3 | 2:6 |
| X.14 | Isopyrazam | 1:1 | 2:2 |
| X.01 | Penthiopyrad | 10:1 | 60:6 |
| X.01 | Penthiopyrad | 30:1 | 60:2 |
| X.01 | Penthiopyrad | 3.3:1 | 20:6 |
| X.01 | Penthiopyrad | 10:1 | 20:2 |
| X.14 | Penthiopyrad | 1:1 | 6:6 |
| X.14 | Penthiopyrad | 3:1 | 6:2 |
| X.14 | Penthiopyrad | 1:3 | 2:6 |
| X.14 | Penthiopyrad | 1:1 | 2:2 |
| X.01 | Pydiflumetofen | 10:1 | 60:6 |
| X.01 | Pydiflumetofen | 30:1 | 60:2 |
| X.14 | Pydiflumetofen | 10:1 | 60:6 |
| X.04 | Pydiflumetofen | 1000:1 | 60:0.06 |
| X.25 | Pydiflumetofen | 10:1 | 60:6 |
| X.24 | Pydiflumetofen | 3:1 | 60:20 |
| X.24 | Pydiflumetofen | 10:1 | 60:6 |
| X.24 | Pydiflumetofen | 1:1 | 20:20 |
| X.24 | Pydiflumetofen | 3.3:1 | 20:6 |
| X.01 | Fluopyram | 10:1 | 60:6 |
| X.01 | Fluopyram | 30:1 | 60:2 |
| X.14 | Fluopyram | 10:1 | 60:6 |
| X.14 | Fluopyram | 30:1 | 60:2 |
| X.25 | Fluopyram | 3:1 | 60:20 |
| X.25 | Fluopyram | 10:1 | 60:6 |
| X.24 | Fluopyram | 3:1 | 60:20 |
| X.24 | Fluopyram | 10:1 | 60:6 |
| X.24 | Fluopyram | 1:1 | 20:20 |
| X.24 | Fluopyram | 3.3:1 | 20:6 |
| X.01 | Azoxystrobin | 1000:1 | 60:0.06 |
| X.14 | Azoxystrobin | 1000:1 | 60:0.06 |
| X.04 | Azoxystrobin | 1000:1 | 60:0.06 |
| X.04 | Azoxystrobin | 3000:1 | 60:0.02 |
| X.07 | Azoxystrobin | 1000:1 | 60:0.06 |
| X.07 | Azoxystrobin | 333.33:1 | 20:0.06 |
| X.25 | Azoxystrobin | 100:1 | 60:0.6 |
| X.25 | Azoxystrobin | 300:1 | 60:0.2 |
| X.25 | Azoxystrobin | 33.33:1 | 20:0.6 |
| X.25 | Azoxystrobin | 100:1 | 20:0.2 |
| X.24 | Azoxystrobin | 100:1 | 60:0.6 |
| X.24 | Azoxystrobin | 300:1 | 60:0.2 |
| X.24 | Azoxystrobin | 33.33:1 | 20:0.6 |
| X.24 | Azoxystrobin | 100:1 | 20:0.2 |
| X.01 | Trifloxystrobin | 1000:1 | 60:0.06 |
| X.14 | Trifloxystrobin | 1000:1 | 60:0.06 |
| X.14 | Trifloxystrobin | 3000:1 | 60:0.02 |
| X.04 | Trifloxystrobin | 3000:1 | 60:0.02 |
| X.25 | Trifloxystrobin | 100:1 | 60:0.6 |
| X.25 | Trifloxystrobin | 300:1 | 60:0.2 |

-continued

| Component A (Compound) | Component B | Ratio A:B | Conc. (ppm) (A:B) |
|---|---|---|---|
| X.24 | Trifloxystrobin | 100:1 | 60:0.6 |
| X.24 | Trifloxystrobin | 300:1 | 60:0.2 |
| X.24 | Trifloxystrobin | 33.33:1 | 20:0.6 |
| X.24 | Trifloxystrobin | 100:1 | 20:0.2 |
| X.01 | Pyraclostrobin | 100:1 | 60:0.6 |
| X.01 | Pyraclostrobin | 300:1 | 60:0.2 |
| X.01 | Pyraclostrobin | 33:1 | 20:0.6 |
| X.07 | Pyraclostrobin | 60:0.6 | 60:0.6 |
| X.07 | Pyraclostrobin | 60:0.2 | 60:0.2 |
| X.25 | Pyraclostrobin | 100:1 | 60:0.6 |
| X.25 | Pyraclostrobin | 300:1 | 60:0.2 |
| X.24 | Pyraclostrobin | 100:1 | 60:0.6 |
| X.24 | Pyraclostrobin | 300:1 | 60:0.2 |
| X.24 | Pyraclostrobin | 33.33:1 | 20:0.6 |
| X.24 | Pyraclostrobin | 100:1 | 20:0.2 |
| X.01 | Cyproconazole | 100:1 | 60:0.6 |
| X.01 | Cyproconazole | 300:1 | 60:0.2 |
| X.14 | Cyproconazole | 100:1 | 60:0.6 |
| X.14 | Cyproconazole | 300:1 | 60:0.2 |
| X.04 | Cyproconazole | 60:0.6 | 60:0.6 |
| X.04 | Cyproconazole | 60:0.2 | 60:0.2 |
| X.07 | Cyproconazole | 100:1 | 60:0.6 |
| X.07 | Cyproconazole | 300:1 | 60:0.2 |
| X.07 | Cyproconazole | 33.33:1 | 20:0.6 |
| X.07 | Cyproconazole | 100:1 | 20:0.2 |
| X.25 | Cyproconazole | 10:1 | 60:6 |
| X.25 | Cyproconazole | 30:1 | 60:2 |
| X.24 | Cyproconazole | 10:1 | 60:6 |
| X.24 | Cyproconazole | 30:1 | 60:2 |
| X.24 | Cyproconazole | 3.33:1 | 20:6 |
| X.24 | Cyproconazole | 10:1 | 20:2 |
| X.01 | Difenoconazole | 10:1 | 60:6 |
| X.01 | Difenoconazole | 30:1 | 60:2 |
| X.01 | Difenoconazole | 3.3:1 | 20:6 |
| X.01 | Difenoconazole | 10:1 | 20:2 |
| X.14 | Difenoconazole | 1:1 | 6:6 |
| X.14 | Difenoconazole | 3:1 | 6:2 |
| X.14 | Difenoconazole | 1:3 | 2:6 |
| X.14 | Difenoconazole | 1:1 | 2:2 |
| X.04 | Difenoconazole | 10:1 | 60:6 |
| X.04 | Difenoconazole | 30:1 | 60:2 |
| X.04 | Difenoconazole | 3.33:1 | 20:6 |
| X.04 | Difenoconazole | 10:1 | 20:2 |
| X.07 | Difenoconazole | 10:1 | 60:6 |
| X.07 | Difenoconazole | 30:1 | 60:2 |
| X.07 | Difenoconazole | 3.33:1 | 20:6 |
| X.07 | Difenoconazole | 10:1 | 20:2 |
| X.25 | Difenoconazole | 10:1 | 60:6 |
| X.25 | Difenoconazole | 30:1 | 60:2 |
| X.25 | Difenoconazole | 3.33:1 | 20:6 |
| X.25 | Difenoconazole | 10:1 | 20:2 |
| X.24 | Difenoconazole | 10:1 | 60:6 |
| X.24 | Difenoconazole | 30:1 | 60:2 |
| X.24 | Difenoconazole | 3.33:1 | 20:6 |
| X.24 | Difenoconazole | 10:1 | 20:2 |
| X.01 | Hexaconazole | 10:1 | 60:6 |
| X.01 | Hexaconazole | 30:1 | 60:2 |
| X.01 | Hexaconazole | 3.3:1 | 20:6 |
| X.14 | Hexaconazole | 1:1 | 6:6 |
| X.04 | Hexaconazole | 10:1 | 60:6 |
| X.04 | Hexaconazole | 30:1 | 60:2 |
| X.04 | Hexaconazole | 3.33:1 | 20:6 |
| X.07 | Hexaconazole | 10:1 | 60:6 |
| X.07 | Hexaconazole | 30:1 | 60:2 |
| X.07 | Hexaconazole | 3.33:1 | 20:6 |
| X.25 | Hexaconazole | 10:1 | 60:6 |
| X.25 | Hexaconazole | 30:1 | 60:2 |
| X.25 | Hexaconazole | 3.33:1 | 20:6 |
| X.24 | Hexaconazole | 10:1 | 60:6 |
| X.24 | Hexaconazole | 30:1 | 60:2 |
| X.24 | Hexaconazole | 3.33:1 | 20:6 |
| X.24 | Hexaconazole | 10:1 | 20:2 |
| X.01 | Propiconazole | 30:1 | 60:2 |
| X.01 | Mefentrifluconazole | 10:1 | 60:6 |
| X.01 | Mefentrifluconazole | 30:1 | 60:2 |
| X.01 | Mefentrifluconazole | 3.3:1 | 20:6 |
| X.01 | Mefentrifluconazole | 10:1 | 20:2 |
| X.14 | Mefentrifluconazole | 1:1 | 6:6 |
| X.14 | Mefentrifluconazole | 3:1 | 6:2 |
| X.14 | Mefentrifluconazole | 1:3 | 2:6 |
| X.14 | Mefentrifluconazole | 1:1 | 2:2 |
| X.04 | Mefentrifluconazole | 10:1 | 60:6 |
| X.04 | Mefentrifluconazole | 30:1 | 60:2 |
| X.04 | Mefentrifluconazole | 3.33:1 | 20:6 |
| X.04 | Mefentrifluconazole | 10:1 | 20:2 |
| X.07 | Mefentrifluconazole | 10:1 | 60:6 |
| X.07 | Mefentrifluconazole | 30:1 | 60:2 |
| X.07 | Mefentrifluconazole | 3.33:1 | 20:6 |
| X.07 | Mefentrifluconazole | 10:1 | 20:2 |
| X.25 | Mefentrifluconazole | 10:1 | 60:6 |
| X.25 | Mefentrifluconazole | 30:1 | 60:2 |
| X.24 | Mefentrifluconazole | 10:1 | 60:6 |
| X.24 | Mefentrifluconazole | 30:1 | 60:2 |
| X.24 | Mefentrifluconazole | 3.33:1 | 20:6 |
| X.24 | Mefentrifluconazole | 10:1 | 20:2 |
| X.01 | Prothioconazole | 10:1 | 60:6 |
| X.01 | Prothioconazole | 30:1 | 60:2 |
| X.01 | Prothioconazole | 3.3:1 | 20:6 |
| X.14 | Prothioconazole | 10:1 | 60:6 |
| X.14 | Prothioconazole | 30:1 | 60:2 |
| X.14 | Prothioconazole | 3.3:1 | 20:6 |
| X.25 | Prothioconazole | 10:1 | 60:6 |
| X.25 | Prothioconazole | 30:1 | 60:2 |
| X.24 | Prothioconazole | 10:1 | 60:6 |
| X.24 | Prothioconazole | 30:1 | 60:2 |
| X.24 | Prothioconazole | 3.33:1 | 20:6 |
| X.24 | Prothioconazole | 10:1 | 20:2 |
| X.01 | Chlorothalonil | 1:1 | 60:60 |
| X.01 | Chlorothalonil | 3:1 | 60:20 |
| X.01 | Chlorothalonil | 1:3 | 20:60 |
| X.01 | Chlorothalonil | 1:1 | 20:20 |
| X.14 | Chlorothalonil | 1:1 | 60:60 |
| X.14 | Chlorothalonil | 3:1 | 60:20 |
| X.14 | Chlorothalonil | 1:3 | 20:60 |
| X.25 | Chlorothalonil | 1:1 | 60:60 |
| X.25 | Chlorothalonil | 3:1 | 60:20 |
| X.25 | Chlorothalonil | 1:3 | 20:60 |
| X.24 | Chlorothalonil | 1:1 | 60:60 |
| X.24 | Chlorothalonil | 3:1 | 60:20 |
| X.24 | Chlorothalonil | 1:3 | 20:60 |
| X.24 | Chlorothalonil | 1:1 | 20:20 |
| X.01 | Mancozeb | 1:1 | 60:60 |
| X.01 | Mancozeb | 3:1 | 60:20 |
| X.01 | Mancozeb | 1:3 | 20:60 |
| X.01 | Mancozeb | 1:1 | 20:20 |
| X.14 | Mancozeb | 1:1 | 60:60 |
| X.14 | Mancozeb | 3:1 | 60:20 |
| X.14 | Mancozeb | 1:3 | 20:60 |
| X.14 | Mancozeb | 1:1 | 20:20 |
| X.25 | Mancozeb | 3:1 | 60:20 |
| X.24 | Mancozeb | 1:1 | 60:60 |
| X.24 | Mancozeb | 3:1 | 60:20 |
| X.24 | Mancozeb | 1:3 | 20:60 |
| X.24 | Mancozeb | 1:1 | 20:20 |
| X.01 | fosetyl-aluminium | 1:3.3 | 60:200 |
| X.01 | fosetyl-aluminium | 1:1 | 60:60 |
| X.24 | Acibenzolar-S-methyl | 1:3.3 | 60:200 |
| X.24 | Acibenzolar-S-methyl | 1:1 | 60:60 |
| X.24 | Acibenzolar-S-methyl | 1:10 | 20:200 |
| X.24 | Acibenzolar-S-methyl | 1:3.3 | 20:60 |

What is claimed is:

1. A fungicidal composition comprising a mixture of components (A) and (B) as active ingredients, wherein component (A) is a compound selected from the group consisting of:
N-methoxy-N-[[4-[5-(trifluoromethyl)-1,2,4-oxadiazol-3-yl]phenyl]methyl]cyclopropanecarboxamide,
N,2-dimethoxy-N-[[4-[5-(trifluoromethyl)-1,2,4-oxadi-azol-3-yl]phenyl]methyl]propenamide, N-ethyl-2-methyl-N-[[4-[5-(trifluoromethyl)-1,2,4-oxa-diazol-3-yl]phenyl]methyl]propenamide,
1-methoxy-3-methyl-1-[[4-[5-(trifluoromethyl)-1,2,4-oxadiazol-3-yl] phenyl] methyl]urea,
and
1,3-dimethoxy-1-[[4-[5-(trifluoromethyl)-1,2,4-oxadiazol-3-yl]phenyl]methyl]urea;
or a salt, enantiomer, tautomer or N-oxide thereof;
and
component (B) is a compound selected from the group consisting of:
benzovindiflupyr, fluxapyroxad, pydiflumetofen, isopyrazam, fluopyram, penthiopyrad, sedaxane, bixafen, difenoconazole, cyproconazole, tebuconazole, hexaconazole, prothioconazole, propiconazole, epoxiconazole, flutriafol, mefentrifluconazole, ipconazole, paclobutrazol, azoxystrobin, trifloxystrobin, picoxystrobin, pyraclostrobin, metalaxyl-M, fenpropidin, fenpropimorph, cyprodinil, spiroxamine, mancozeb, chlorothalonil, oxathiapiprolin, mandipropamid, fluazinam, fludioxinil, fosetyl-aluminium, acibenzolar-S-methyl, procymidone, carbendazim, fenhexamid, prochloraz, prohexadione-calcium, plant extract comprising tea tree oil, N'-[5-bromo-2-methyl-6-(1-methyl-2-propoxy-ethoxy)-3-pyridyl]-N-ethyl-N-methyl-formamidine), N'-[5-bromo-2-methyl-6-[(1S)-1-methyl-2-propoxy-ethoxy]-3-pyridyl]-N-ethyl-N-methyl-formamidine, N'-[5-bromo-2-methyl-6-[(1R)-1-methyl-2-propoxy-ethoxy]-3-pyridyl]-N-ethyl-N-methyl-formamidine, N'-[5-bromo-2-methyl-6-(1-methyl-2 propoxy-ethoxy)-3-pyridyl]-N-isopropyl-N-methyl-formamidine, N'-[5-chloro-2-methyl-6-(1-methyl-2-propoxy-ethoxy)-3-pyridyl]-N-ethyl-N-methyl-formamidine, calcium phosphonate, cis-jasmone, trinexapac-ethyl, glyphosate, 2,4-D (2,4-dichlorophenoxyacetic acid) and thiamethoxam.

2. The fungicidal composition according to claim 1, wherein component (A) is:
N-methoxy-N-[[-4-[5-(trifluoromethyl)-1,2,4-oxadiazol-3-yl]phenyl]methyl]cyclopropanecarboxamide,
N,2-dimethoxy-N-[[4-[5-(trifluoromethyl)-1,2,4-oxadiazol-3-yl]phenyl]methyl]propenamide, or 1-methoxy-3-methyl-1-[[4-[5-(trifluoromethyl)-1,2,4-oxadiazol-3-yl]phenyl]methyl]urea or
a salt, enantiomer, tautomer or N-oxide thereof.

3. The fungicidal composition according to claim 1, wherein component (B) is a compound selected from the group consisting of benzovindiflupyr, fluxapyroxad, pydiflumetofen, isopyrazam, fluopyram, penthiopyrad, difenoconazole, cyproconazole, tebuconazole, hexaconazole, prothioconazole, mefentrifluconazole, azoxystrobin, trifloxystrobin, picoxystrobin, pyraclostrobin, fenpropidin, fenpropimorph, mancozeb, chlorothalonil, and N'-[5-bromo-2-methyl-6-(1-methyl-2-propoxy-ethoxy)-3-pyridyl]-N-ethyl-N-methyl-formamidine.

4. The fungicidal composition according to claim 1, wherein component (B) is a compound selected from the group consisting of benzovindiflupyr, pydiflumetofen, difenoconazole, cyproconazole, hexaconazole, prothioconazole, azoxystrobin, fenpropidin, and N'-[5-b rom o-2-methyl-6-(1-methyl-2-prop oxy-ethoxy)-3-pyridyl]-N-ethyl-N-methyl-formamidine.

5. The fungicidal composition according to claim 1, wherein the weight ratio of component (A) to component (B) is from 100:1 to 1:100.

6. The fungicidal composition according to claim 1, wherein the weight ratio of component (A) to component (B) is from 20:1 to 1:40.

7. The fungicidal composition according to claim 1, wherein the weight ratio of component (A) to component (B) is from 12:1 to 1:25.

8. The fungicidal composition according to claim 1, wherein the weight ratio of component (A) to component (B) is from 5:1 to 1:15.

9. The fungicidal composition according to claim 1, wherein the weight ratio of component (A) to component (B) is from 2:1 to 1:5.

10. The fungicidal composition according to claim 1, wherein the composition further comprises one or more additional pesticides selected from the group consisting of: a fungicide, selected from etridiazole, fluazinam, benzovindiflupyr, pydiflumetofen, benalaxyl, benalaxyl-M (kiralaxyl), furalaxyl, metalaxyl, metalaxyl-M (mefenoxam), dodicin, N'-(2,5-Dimethyl-4-phenoxy-phenyl)-N-ethyl-N-methyl-formamidine, N'-[4-(4,5-Dichloro-thiazol-2-yl oxy)-2,5-dimethyl-phenyl]-N-ethyl-N-methyl-formamidine, N'-[4-[[3-[(4-chlorophenyl)methyl]-1,2,4-thiadiazol-5-yl]oxy]-2,5-dimethyl-phenyl]-N-ethyl-N-methyl-formamidine, ethirimol, 3'-chloro-2-methoxy-N-[(3RS)-tetrahydro-2-oxo-furan-3-yl]acet-2',6'-xylidide (clozylacon), cyprodinil, mepanipyrim, pyrimethanil, dithianon, aureofungin, blasticidin-S, biphenyl, chloroneb, dicloran, hexachlorobenzene, quintozene, tecnazene, tecnazene (TCNB), tolclofos-methyl, metrafenone, 2,6-dichloro-N-(4-trifluoromethyl-benzyl)-benzamide, fluopicolide (flupicolide), tioxymid, flusulfamide, benomyl, carbendazim, carbendazim chlorhydrate, chlorfenazole, fuberidazole, thiabendazole, thiophanate-methyl, benthiavalicarb, chlobenthiazone, probenazole, acibenzolar, bethoxazin, pyriofenone (IKF-309), acibenzolar-S-methyl, pyribencarb (KIF-7767), butylamine, 3-iodo-2-propinyl n-butylcarbamate (IPBC), picarbutrazox, polycarbamate, propamocarb, tolprocarb, 3-(difluoromethyl)-N-(7-fluoro-1,1,3,3-tetramethyl-indan-4-yl)-1-methyl-pyrazole 4-carboxamide, diclocymet, N-[(5-chloro-2-isopropyl-phenyl)methyl]-N-cyclopropyl-3-(difluoromethyl)-5-fluoro-1-methyl-pyrazole-4-carboxamide, N-cyclopropyl-3-(difluoromethyl)-5-fluoro-N-[(2-isopropylphenyl)methyl]-1-methyl-pyrazole-4-carboxamide, carpropamid, chlorothalonil, flumorph, oxine-copper, cymoxanil, phenamacril, cyazofamid, flutianil, thicyofen, chlozolinate, iprodione, procymidone, vinclozolin, bupirimate, dinocton, dinopenton, dinobuton, dinocap, meptyldinocap, diphenylamine, phosdiphen, 2,6-dimethyl-[1,4]dithiino[2,3-c:5,6-c']dipyrrole-1,3,5,7(2H,6H)-tetra-one, azithiram, etem, ferbam, mancozeb, maneb, metam, metiram, metiram-zinc, nabam, propineb, thiram, metam sodium, zineb, ziram, dithioether, isoprothiolane, ethaboxam, fosetyl, fosetyl-aluminium (fosetyl-al), methyl bromide, methyl iodide, methyl isothiocyanate, cyclafuramid, fenfuram, validamycin, streptomycin, (2RS)-2-bromo-2-(bromomethyl)glutaronitrile (bromothalonil), dodine, doguadine, guazatine, iminoctadine, iminoctadine triacetate, 2,4-D, 4-(2,4-dichlorophenoxy)butyric acid (2,4-DB), kasugamycin, dimethirimol, fenhexamid, hymexazole, hydroxyisoxazole imazalil, imazalil sulphate, oxpoconazole, pefurazoate, prochloraz, triflumizole, fenamidone, Bordeaux mixture, calcium polysulfide, copper acetate, copper carbonate, copper hydroxide, copper naphthenate, copper oleate, copper oxychloride, copper oxyquinolate, copper silicate, copper sulphate, copper tallate, cuprous oxide, sulphur, carbaryl, phthalide (fthalide), pyrisoxazole (dingjunezuo, Jun Si Qi), oxathiapiprolin, fluoroimide, mandipropamid, KSF-1002, benzamorf, dimethomorph, fenpropimorph, tridemorph, dodemorph, diethofencarb, fentin acetate, fentin hydroxide, carboxin, oxycarboxin, drazoxolon, famoxadone, m-phenylphenol, p-phenylphenol, tribromophenol (TBP), 2-[2-[(7,8-difluoro-2-methyl-3-quinolyl)oxy]-6-fluoro-phenyl]propan-2-ol, 2-[2-fluoro-6-[(8-fluoro-2-methyl-3-quinolyl)oxy]phenyl]propan-2-ol, cyflufenamid, ofurace, oxadixyl, flutolanil, mepronil, isofetamid, fenpiclonil, fludioxonil, pencycuron, edifenphos, iprobenfos, pyrazophos, phosphorus acids, tecloftalam, captafol, captan, ditalimfos, triforine, fenpropidin, piperalin, osthol, 1-methylcyclopropene, 4-chlorophenoxyacetic acid (4-CPA), chlormequat, clofencet, dichlorprop, dimethipin, endothal, ethephon, flumetralin, forchlorfenuron, gibberellic acid, gibberellins, hymexazol, maleic hydrazide, mepiquat, naphthalene acetamide, paclobutrazol, probexadione, prohexadione-calcium, thidiazuron, tribufos (tributyl phosphorotrithioate), trinexapac, uniconazole, a-naphthalene acetic acid, polyoxin D (polyoxrim), Banda de *Lupinus Albus* Doce (BLAD), chitosan, fenoxanil, folpet, 3-(difluoromethyl)-N-methoxy-1-methyl-N-[1-methyl-2-(2,4, 6-trichlorophenyl)ethyl]pyrazol e-4-carboxamide, bixafen, fluxapyroxad, furametpyr, isopyrazam, penflufen, penthiopyrad, sedaxane, fenpyrazamine, diclomezine, pyrifenox, boscalid, fluopyram, diflumetorim, fenarimol, 5-fluoro-2-(p-tolylmethoxy) pyrimidin-4-amine ferimzone, dimetachlone, pyroquilon, proquinazid, ethoxyquin, quinoxyfen, 4,4,5-trifluoro-3,3-dimethyl-1-(3-quinolyl)isoquinoline, 4,4-difluoro-3,3-dimethyl-1-(3-quinolyl)isoquinoline, 5-fluoro-3,3,4,4-tetramethyl-1-(3-quinolyl)isoquinoline, 9-fluoro-2,2-dimethyl-5-(3-quinolyl)-3H-1,4-benzoxazepine, tebufloquin, oxolinic acid, chinomethionate (oxythioquinox, quinoxymethionate), spiroxamine, (E)-N-methyl-2-[2-(2,5-dimethylphenoxymethyl) phenyl]-2-methoxy-iminoacetamide, azoxystrobin, coumoxystrobin, dimoxystrobin, enestroburin, pyriotrobin, fenamistrobin, flufenoxystrobin, fluoxastrobin, kresoximmethyl, mandestrobin, metaminostrobin, metominostrobin, orysastrobin, picoxystrobin, pyraclostrobin, pyrametostrobin, pyraoxystrobin, triclopyricarb, trifloxystrobin, amisulbrom, dichlofluanid, tolylfluanid, but-3-ynyl N-[6-[[(Z)-[(1-methyltetrazol-5-yl)-phenyl-methylene]amino]oxymethyl]-2-pyridyl]carbamate, dazomet, isotianil, tiadinil, thifluzamide, benthiazole (TCMTB), silthiofam, zoxamide, anilazine, tricyclazole, (+/−)-cis-1-(4-chlorophenyl)-2-(1H-1,2, 4-triazol-1-yl)-cycloheptanol (huanjunzuo), 1-(5-bromo-2-pyridyl)-2-(2,4-difluorophenyl)-1, 1-difluoro-3-(1,2,4-triazol-1-yl)propan-2-ol 2-(1-tert-butyl)-1-(2-chlorophenyl)-3-(1,2,4-triazol-1-yl)-propan-2-ol (TCDP), (N'-[5-bromo-2-methyl-6-(1-methyl-2-propoxy-ethoxy)-3-pyridyl]-N-ethyl-N-methyl-formamidine), azaconazole, bitertanol, bromuconazole, climbazole, cyproconazole, difenoconazole, dimetconazole, diniconazole, diniconazole-M, epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, mefentrifluconazole, simeconazole, tebuconazole, tetraconazole, triadimefon, triadimenol, triazoxide, triticonazole, 2-[[(1R, 5 S)-5-[(4-fluorophenyl)methyl]-1-hydroxy-2,2-dimethyl-cyclopentyl]methyl]-4H-1,2,4-triazole-3-thione, 2-[[3-(2-chlorophenyl)-2-(2,4-difluorophenyl)oxiran-2-yl]methyl]-4H-1,2,4-triazole-3-thione, ametoctradin, iprovalicarb, valifenalate, 2-benzyl-4-chlorophenol (Chlorophene), allyl alcohol, azafenidin, benzalkonium chloride, chloropicrin, cresol, daracide, dichlorophen (dichlorophene), difenzoquat, dipyrithione, N-(2-p-chlorobenzoylethyl)-hexaminium chloride, NNF-0721, octhilinone, oxasulfuron, plant extract comprising tea tree oil, propamidine and propionic acid; or an insecticide selected from abamectin, acephate, acetamiprid, amidoflumet (S-1955), avermectin, azadirachtin, azinphos-methyl, bifenthrin, bifenazate, buprofezin, carbofuran, cartap, chlorantraniliprole (DPX-E2Y45), chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; or a bactericides selected from streptomycin; or an acaricide selected from amitraz, chinomethionat, chlorobenzilate, cyenopyrafen, cyhexatin, dicofol, dienochlor, etoxazole, fenazaquin, fenbutatin oxide, fenpropathrin, fenpyroximate, hexythiazox, propargite, pyridaben and tebufenpyrad; or a biological agent selected from *Bacillus thuringiensis*, *Bacillus thuringiensis* delta endotoxin, baculovirus, and entomopathogenic bacteria, entomopathogenic virus and entomopathogenic fungi.

11. The fungicidal composition according to claim 1, wherein the composition further comprises an agriculturally acceptable carrier and, optionally, a surfactant and/or formulation adjuvants.

12. A method, comprising: applying to useful plants, the locus thereof or propagation material thereof a fungicidal composition as defined in claim 1.

13. The method according to claim 12, wherein the composition components (A) and (B) are applied in a sequential manner.

\* \* \* \* \*